United States Patent
Lu et al.

(10) Patent No.: US 10,443,069 B2
(45) Date of Patent: Oct. 15, 2019

(54) PLANTS AND METHODS TO IMPROVE AGRONOMIC CHARACTERISTICS UNDER ABIOTICSTRESS CONDITIONS

(71) Applicant: PIONEER OVERSEAS CORPORATION, Johnston, IA (US)

(72) Inventors: Guihua Lu, Beijing (CN); Yang Gao, Beijing (CN); Min Liu, Beijing (CN); Junhua Liu, Beijing (CN); Guanfan Mao, Beijing (CN); Changgui Wang, Beijing (CN); Wei Wang, Beijing (CN); Xiping Wang, Beijing (CN)

(73) Assignee: PIONEER OVERSEAS CORPORATION

( * ) Notice: Subject to any disclaimer, the term of this patent is extended or adjusted under 35 U.S.C. 154(b) by 39 days.

(21) Appl. No.: 15/309,647

(22) PCT Filed: Jul. 2, 2015

(86) PCT No.: PCT/CN2015/083235
§ 371 (c)(1),
(2) Date: Nov. 8, 2016

(87) PCT Pub. No.: WO2016/000645
PCT Pub. Date: Jan. 7, 2016

(65) Prior Publication Data
US 2017/0268017 A1    Sep. 21, 2017

(30) Foreign Application Priority Data
Jul. 3, 2014    (WO) ................ PCT/CN2014/081601

(51) Int. Cl.
C12N 15/82    (2006.01)
C07K 14/415    (2006.01)

(52) U.S. Cl.
CPC ........ *C12N 15/8273* (2013.01); *C07K 14/415* (2013.01)

(58) Field of Classification Search
None
See application file for complete search history.

(56) References Cited

U.S. PATENT DOCUMENTS

| 6,096,504 A | 8/2000 | McGonigle et al. | |
| 2006/0123505 A1* | 6/2006 | Kikuchi | C07K 14/415 800/278 |
| 2007/0039076 A1* | 2/2007 | Boukharov | C07K 14/415 800/320.2 |

FOREIGN PATENT DOCUMENTS

| CN | 103614385 | 3/2014 | |
| WO | WO2003008540 A2 * | 1/2003 | ............ C12N 15/82 |
| WO | 2011053897 A1 | 5/2011 | |

OTHER PUBLICATIONS

Tripathi et al. Transformed yeast (*Schizosaccharomyces pombe*) overexpressing rice Tau class glutathione S-transferase (OsGSTU30 and OsGSTU41) shows enhanced resistance to hexavalent chromium. Metallomics. 2014. 6: 1549-1557.*
Ji et al. Over-expression of a glutathione S-transferase gene, GsGST, from wild soybean (*Glycine soja*) enhances drought and salt tolerance in transgenic tolerance. Biotechnology Letters. 2010. 32: 1173-1179.*
Zhao et al. Response of antioxidant system to drought and heat stress in transgenic rice roots carrying GST and CAT1. Acta Botanica Boreali-Occidentalia Sinica . 2009. 29(10): 1980-1987. Abstract attached pp. 1-2.*
Pyngrope et al. Reactive oxygen species, ascorbate-glutathione pool, and enzymes of their metabolism in drought-sensitive and tolerant indica rice ( *Oryza sativa* L.) seedlings subjected to progressing levels of water deficit. Protoplasma. 2013. 250: 585-600.*
International Search Report from PCT/CN2015/083235 dated Sep. 23, 2015.
McGonigle, B et al., "gluthathione S-transerase GST 28, partial (*Zea Mays*) retrieved from NCBI Database accession No. AAG34836. 1" Database GenBank, Nov. 28, 2000 (Nov. 28, 2000).
Tanaka, T. et al., "*Oryza sativa* Japonica Group Os01g950000(Os01g0950000)mRNA, complete cds retrieved from NCBI Database accession No. NM_001051939.1" Database GenBank, Nov. 28, 2000 (Nov. 28, 2001).
Fain et al. "Comprehensive expression analysis suggests overlapping and specific roles of rice glutathione S-transferase genes during development and stress responses" BMC Genomics 2010, 11:73 (biomedcentral.com/1471-2164/11/73).

* cited by examiner

*Primary Examiner* — Ashley K Buran

(57) ABSTRACT

Isolated polynucleotides and polypeptides, and recombinant DNA constructs useful for conferring improved drought tolerance; compositions (such as plants or seeds) comprising these recombinant DNA constructs; and methods utilizing these recombinant DNA constructs are disclosed. The recombinant DNA constructs comprise a polynucleotide operably linked to a promoter that is functional in a plant, wherein said polynucleotides encode drought tolerance polypeptides.

6 Claims, 12 Drawing Sheets
Specification includes a Sequence Listing.

PLANTS AND METHODS TO IMPROVE AGRONOMIC CHARACTERISTICS UNDER ABIOTIC STRESS CONDITIONS

FIELD

The field relates to plant breeding and genetics and, in particular, relates to recombinant DNA constructs useful in plants for improving tolerance to abiotic stress, such as drought stress.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses of more than 50% for major crops (Boyer, J. S. (1982) *Science* 218:443-448; Bray, E. A. et al. (2000) In Biochemistry and Molecular Biology of Plants, edited by Buchannan, B. B. et al., Amer. Soc. Plant Biol., pp. 1158-1249). Plants are sessile and have to adjust to the prevailing environmental conditions of their surroundings. This has led to their development of a great plasticity in gene regulation, morphogenesis, and metabolism. Adaption and defense strategies involve the activation of genes encoding proteins important in the acclimation or defense towards the different stresses.

Drought (insufficient available water) is one of the major abiotic stresses that limit crop productivity worldwide, and exposure of plants to a water-limiting environment during various developmental stages appears to activate various physiological and developmental changes. Although many reviews on molecular mechanisms of abiotic stress responses and genetic regulatory networks of drought stress tolerance have been published (Valliyodan, B., and Nguyen, H. T. (2006) *Curr. Opin. Plant Biol.* 9:189-195; Wang, W., et al. (2003) *Planta* 218:1-14; Vinocur, B., and Altman, A. (2005) *Curr. Opin. Biotechnol.* 16: 123-132; Chaves, M. M., and Oliveira, M. M. (2004) *J. Exp. Bot.* 55: 2365-2384; Shinozaki, K., et al. (2003) *Curr. Opin. Plant Biol.* 6:410-417; Yamaguchi-Shinozaki, K., and Shinozaki, K. (2005) *Trends Plant Sci.* 10:88-94), it remains a major challenge in biology to understand the basic biochemical and molecular mechanisms of drought stress perception, signal transduction and tolerance. Genetic research has shown that drought tolerance is a quantitative trait, controlled by many genes. Molecular marker-assisted breeding has led to improved drought tolerance in crops. However, marker accuracy and breeding efficiency remain problematic (Ashraf M. (2010) *Biotechnol. Adv.* 28:169-183). The transgenic approaches to engineering drought tolerance in crops have made great progress (Vinocur B. and Altman A. (2005) *Curr. Opin. Biotechnol.* 16:123-132; Lawlor D W. (2013) *J. Exp. Bot.* 64:83-108).

Earlier work on molecular aspects of abiotic stress responses was accomplished by differential and/or subtractive analysis (Bray, E. A. (1993) *Plant Physiol.* 103:1035-1040; Shinozaki, K., and Yamaguchi-Shinozaki, K. (1997) *Plant Physiol.* 115:327-334; Zhu, J.-K. et al. (1997) *Crit. Rev. Plant Sci.* 16:253-277; Thomashow, M. F. (1999) *Annu. Rev. Plant Physiol. Plant Mol. Biol.* 50:571-599); and other methods which include selection of candidate genes and analysis of expression of such a gene or its active product under stresses, or by functional complementation in a stressor system that is well defined (Xiong, L. and Zhu, J.-K. (2001) *Physiologia Plantarum* 112:152-166). Additionally, forward and reverse genetic studies involving the identification and isolation of mutations in regulatory genes have been used to provide evidence for observed changes in gene expression under stress (Xiong, L. and Zhu, J.-K. (2001) *Physiologia Plantarum* 112:152-166).

Activation tagging can be utilized to identify genes with the ability to affect a trait, and this approach has been used in *Arabidopsis thaliana* (the model plant species) (Weigel, D., et al. (2000) *Plant Physiol.* 122:1003-1013). Insertions of transcriptional enhancer elements can dominantly activate and/or elevate the expression of nearby endogenous genes, so it can be used to select genes involved in agronomically important phenotypes, including abiotic stress tolerance such as improved drought tolerance.

SUMMARY

The following embodiments are among those encompassed by the disclosure:

In one embodiment, the present disclosure includes an isolated polynucleotide, comprising: (a) a polynucleotide with nucleotide sequence of at least 85% sequence identity to SEQ ID NO: 3, 6, 9, 12, 15 or 18; (b) a polynucleotide with nucleotide sequence of at least 85% sequence identity to SEQ ID NO: 4, 7, 10, 13, 16 or 19; (c) a polynucleotide encoding a polypeptide with amino acid sequence of at least 90% sequence identity to SEQ ID NO: 5, 8, 11, 14, 17 or 20; or (d) the full complement of the nucleotide sequence of (a), (b) or (c), wherein over-expression of the polynucleotide in a plant enhances drought tolerance; the isolated polynucleotide comprises the nucleotide sequence of SEQ ID NO: 3, 4, 6, 7, 9, 10, 12, 13, 15, 16, 18 or 19; and the said polypeptide comprises the amino acid sequence of SEQ ID NO: 5, 8, 11, 14, 17 or 20.

In another embodiment, the present disclosure includes a recombinant DNA construct comprising the isolated polynucleotide operably linked to at least one heterologous regulatory sequence, wherein the polynucleotide comprises (a) a polynucleotide with nucleotide sequence of at least 85% sequence identity to SEQ ID NO: 3, 4, 6, 7, 9, 10, 12, 13, 15, 16, 18 or 19; (b) a polynucleotide encoding a polypeptide with amino acid sequence of at least 90% sequence identity to SEQ ID NO: 5, 8, 11, 14, 17 or 20; or (c) the full complement of the nucleotide sequence of (a) or (b).

In another embodiment, the present disclosure includes a transgenic plant or seed comprising a recombinant DNA construct, wherein the recombinant DNA construct comprises the polynucleotide operably linked to at least one regulatory sequence, wherein the polynucleotide comprises (a) a polynucleotide with nucleotide sequence of at least 85% sequence identity to SEQ ID NO: 3, 4, 6, 7, 9, 10, 12, 13, 15, 16, 18 or 19; (b) a polynucleotide encoding a polypeptide with amino acid sequence of at least 90% sequence identity to SEQ ID NO: 5, 8, 11, 14, 17 or 20; or (c) the full complement of the nucleotide sequence of (a) or (b).

In another embodiment, the present disclosure includes a transgenic plant comprising in its genome a recombinant DNA construct comprising a polynucleotide operably linked to at least one regulatory element, wherein the polynucleotide comprises (a) a polynucleotide with nucleotide sequence of at least 85% sequence identity to SEQ ID NO: 3, 4, 6, 7, 9, 10, 12, 13, 15, 16, 18 or 19; (b) a polynucleotide encoding a polypeptide with amino acid sequence of at least 90% sequence identity to SEQ ID NO: 5, 8, 11, 14, 17 or 20; or (c) the full complement of the nucleotide sequence of (a) or (b); the said plant exhibits improved drought tolerance when compared to a control plant.

In another embodiment, the present disclosure includes any of the plants of the disclosure, wherein the plant is selected from the group consisting of rice, maize, soybean, sunflower, sorghum, canola, wheat, alfalfa, cotton, barley, millet, sugar cane and switchgrass.

In another embodiment, methods are provided for increasing drought tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, when compared to SEQ ID NO: 5, 8, 11, 14, 17 or 20; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased drought tolerance when compared to a control plant not comprising the recombinant DNA construct.

In another embodiment, methods are provided for evaluating drought tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, when compared to SEQ ID NO: 5, 8, 11, 14, 17 or 20; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for drought tolerance compared to a control plant not comprising the recombinant DNA construct.

In another embodiment, the present disclosure concerns a recombinant DNA construct comprising any of the isolated polynucleotides of the present disclosure operably linked to at least one regulatory sequence, and a cell, a plant, or a seed comprising the recombinant DNA construct. The cell may be eukaryotic, e.g., a yeast, insect or plant cell; or prokaryotic, e.g., a bacterial cell.

BRIEF DESCRIPTION OF THE DRAWINGS AND SEQUENCE LISTING

The disclosure can be more fully understood from the following detailed description and the accompanying drawings and sequence listing which form a part of this application.

Figure 3:
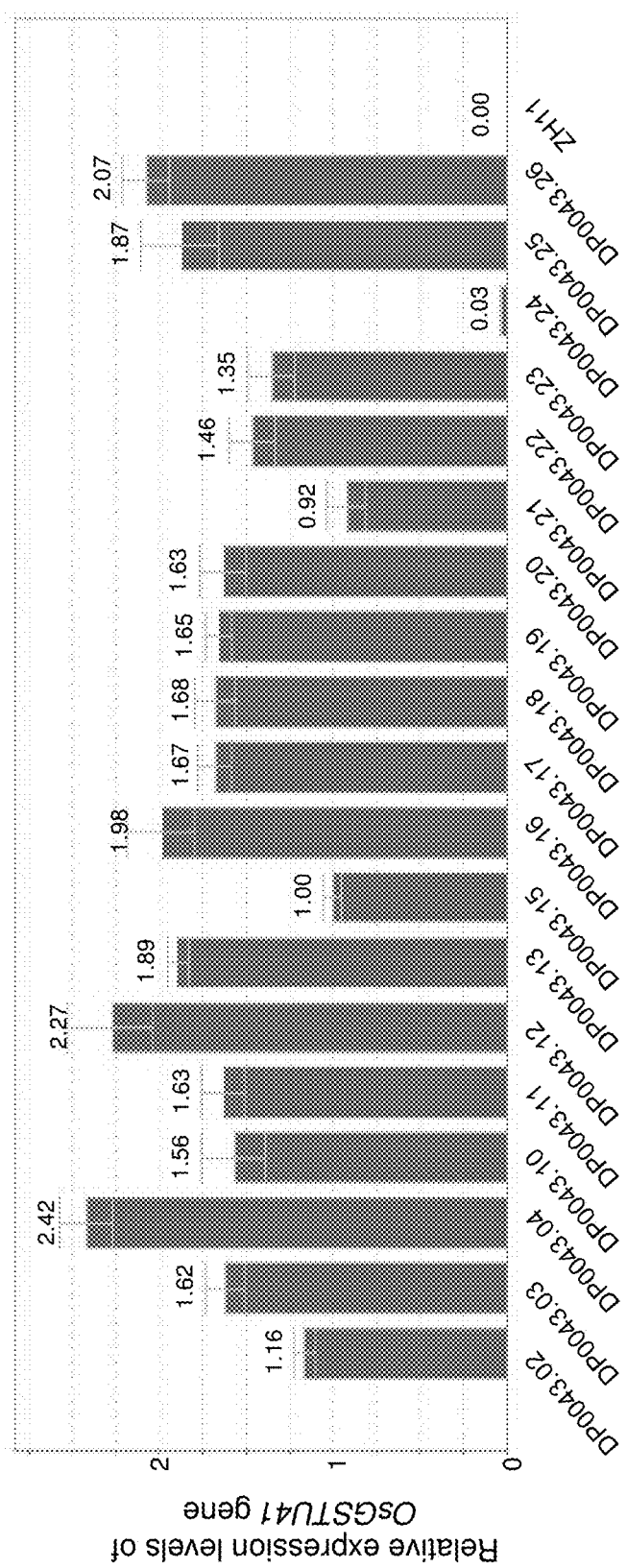

FIG. 3 shows the relative expression levels of OsGSTU41 gene in leaves of different transgenic rice lines by real-time PCR analyses. The base expression level in DP0043.15 is set at 1.00, the numbers on the top of the columns are fold-changes compared to DP0043.15 rice. ZH11 is wild type rice.

Figure 4:
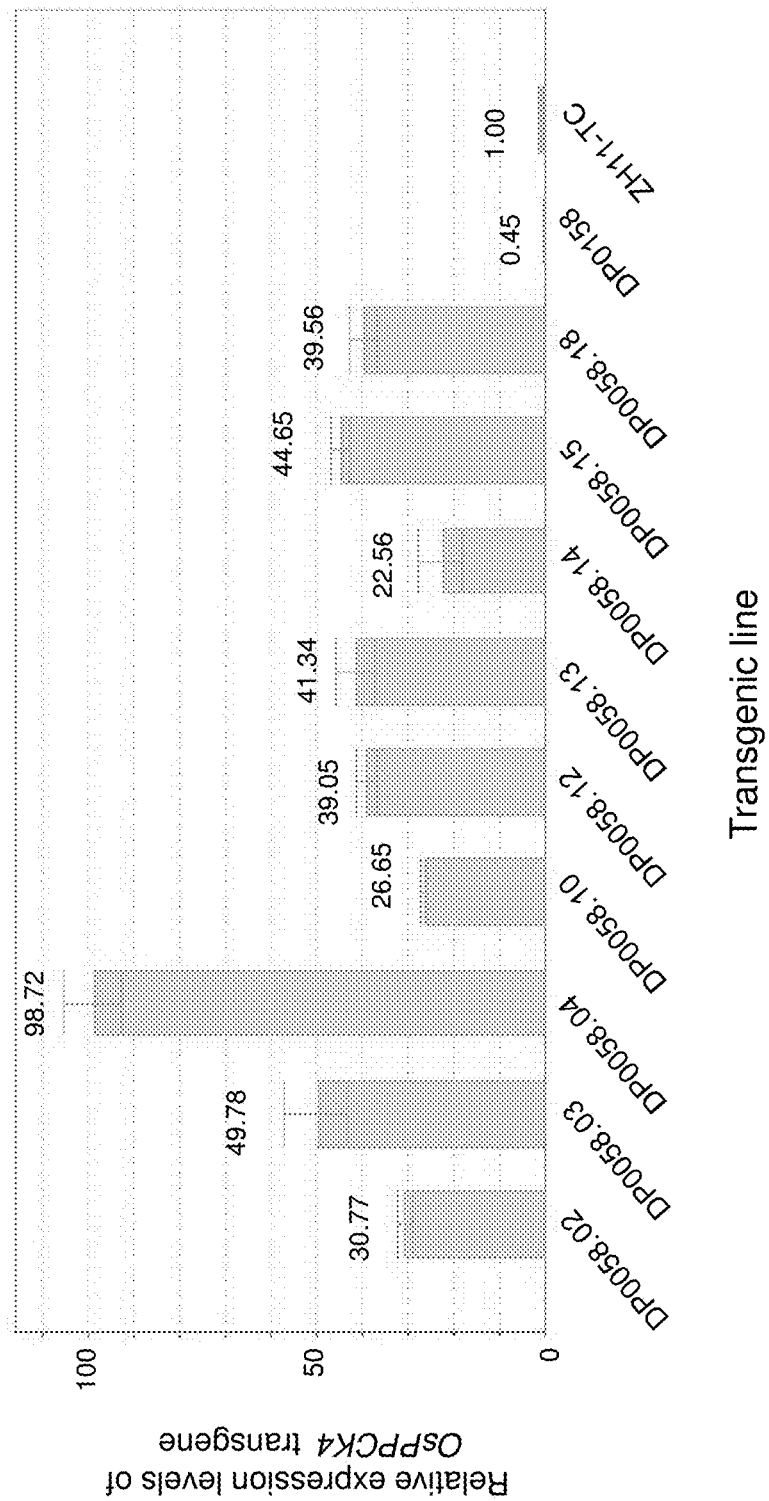

FIG. 4 shows the relative expression levels of OsPPCK4 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11 rice and DP0158 is empty vector transformed ZH11 rice plants.

Figure 5:
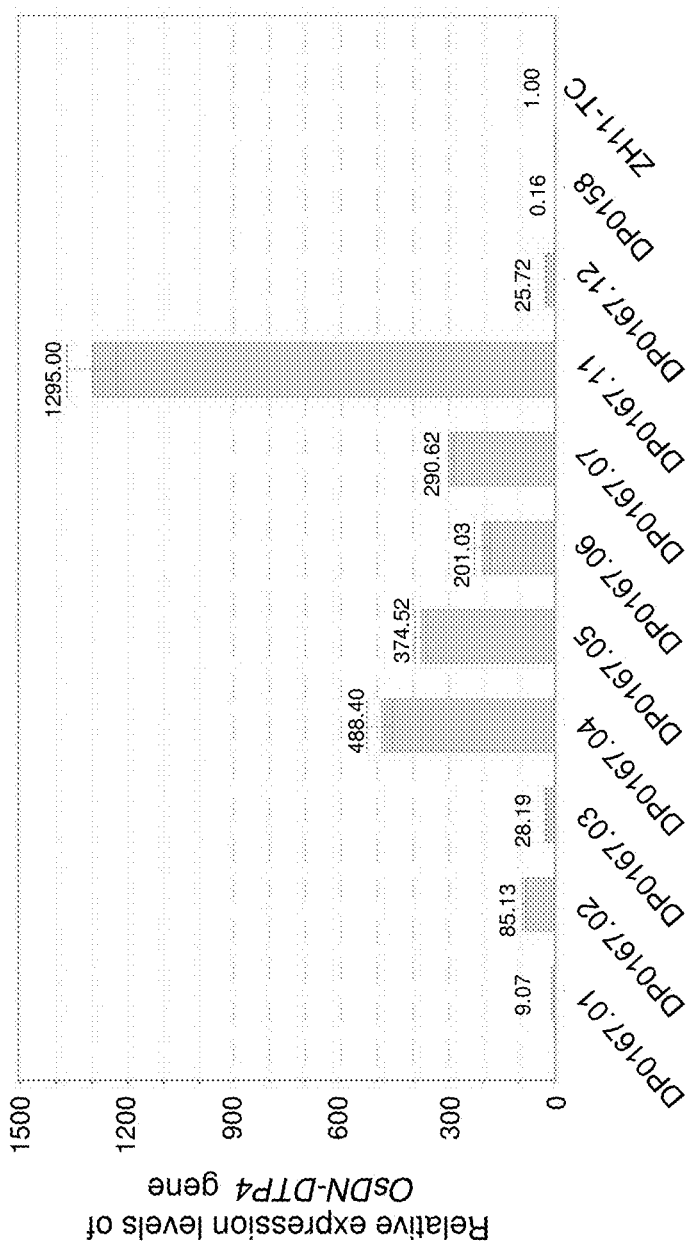

FIG. 5 shows the relative expression levels of OsDN-DTP4 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11 rice and DP0158 is empty vector transformed ZH11 rice plants.

Figure 6:
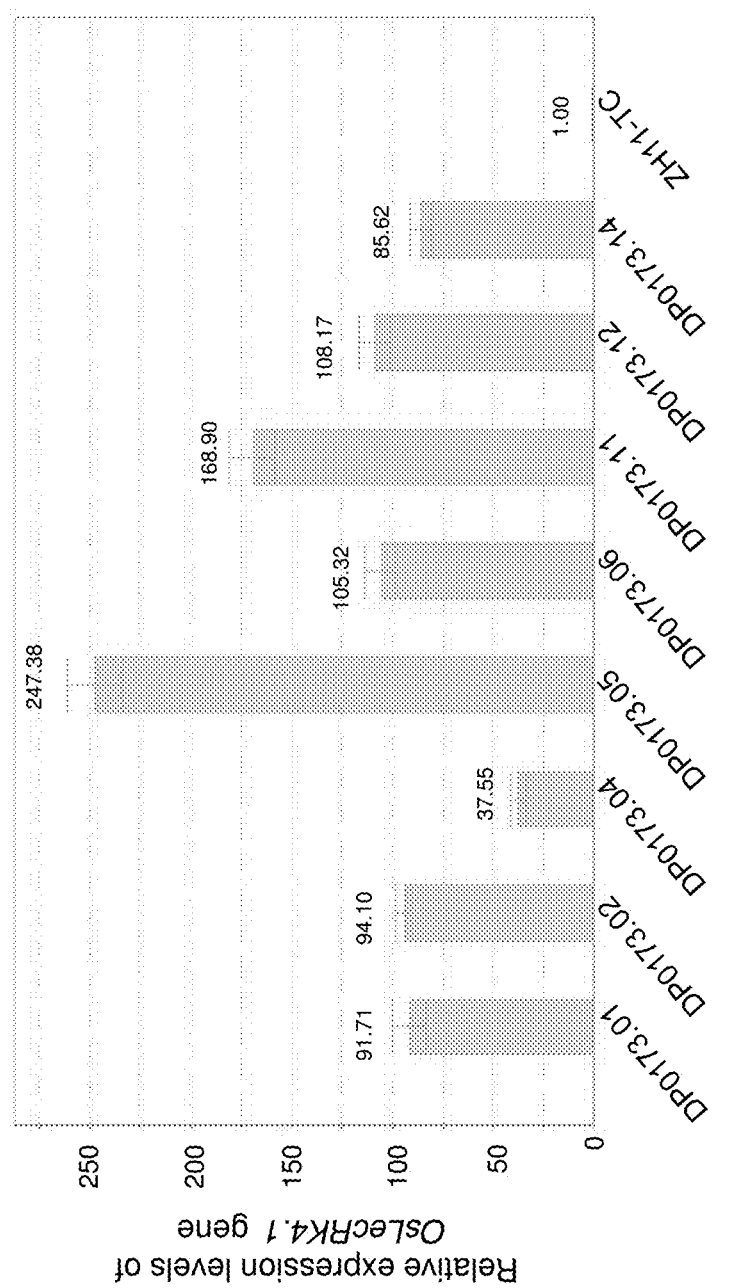

FIG. 6 shows the relative expression levels of OsLecRK4.1 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11 rice plants.

Figure 7:
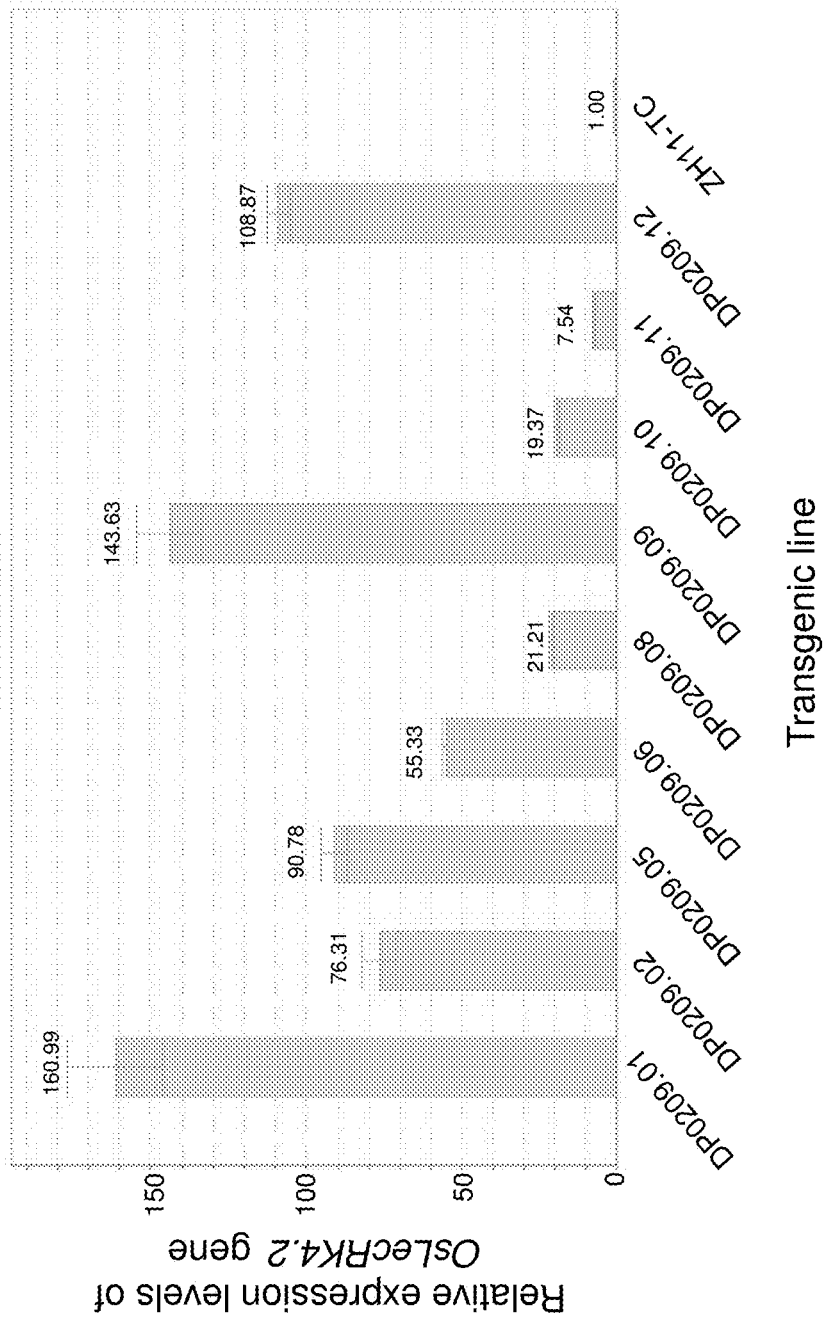

FIG. 7 shows the relative expression levels of OsLecRK4.2 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11 rice plants.

Figure 8:
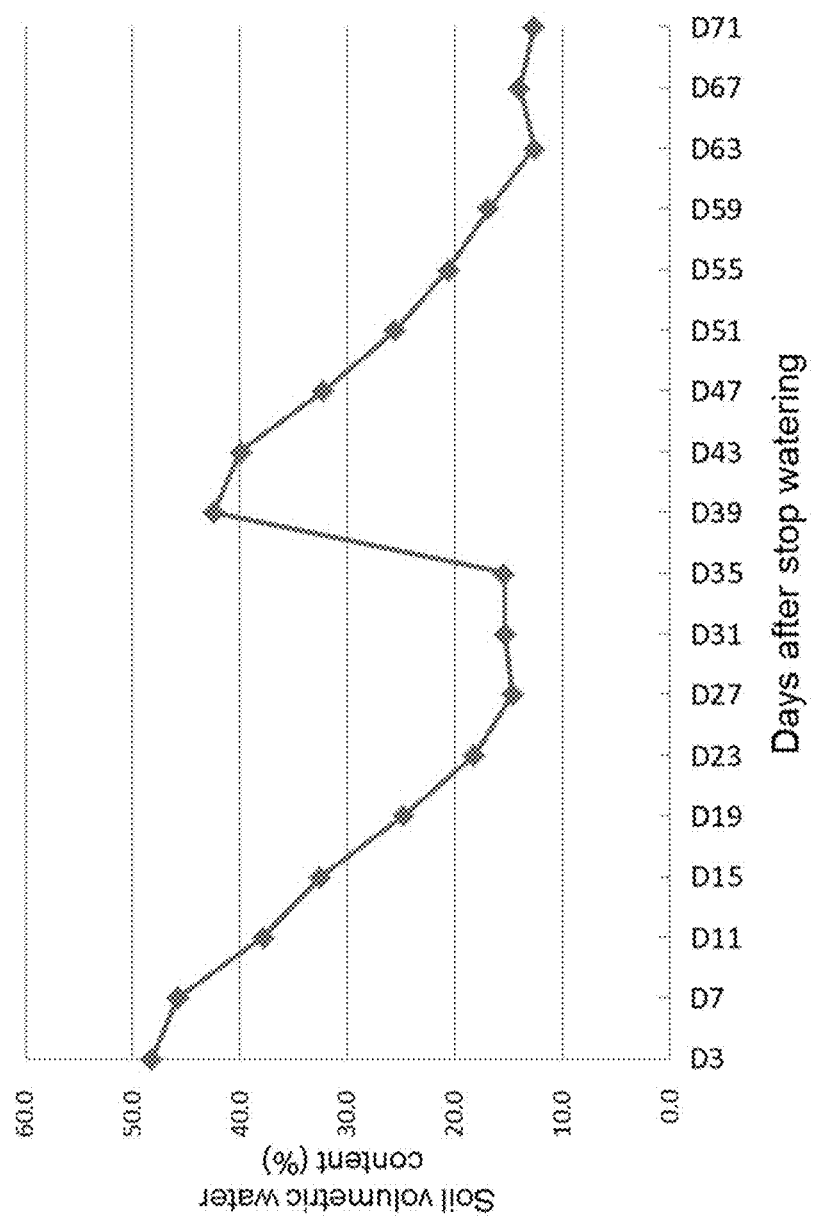

FIG. 8 shows changes of soil volumetric water content at different developmental stage for drought testing OsPPCK4 transgenic rice.

Figure 9:
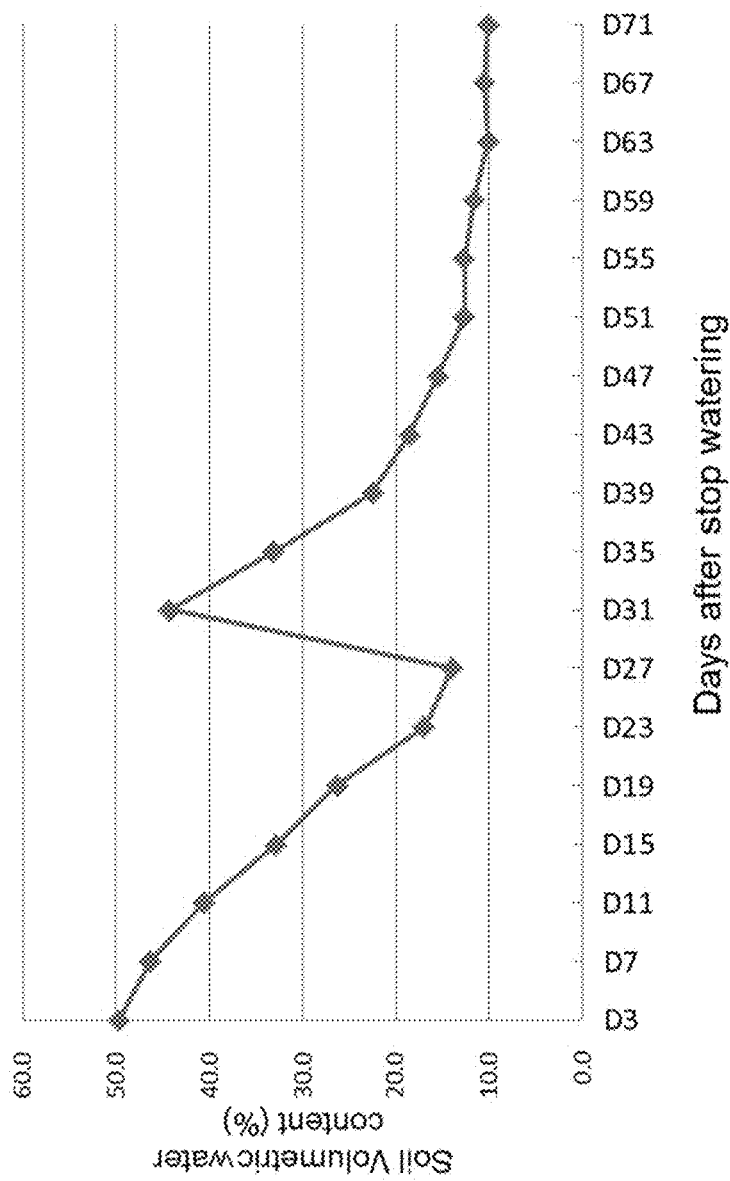

FIG. 9 shows changes of soil volumetric water content at different developmental stage for drought testing OsCAM2 transgenic rice in the first experiment. The OsCAM2 transgenic rice started heading at 31 days after stopping watering.

Figure 10:
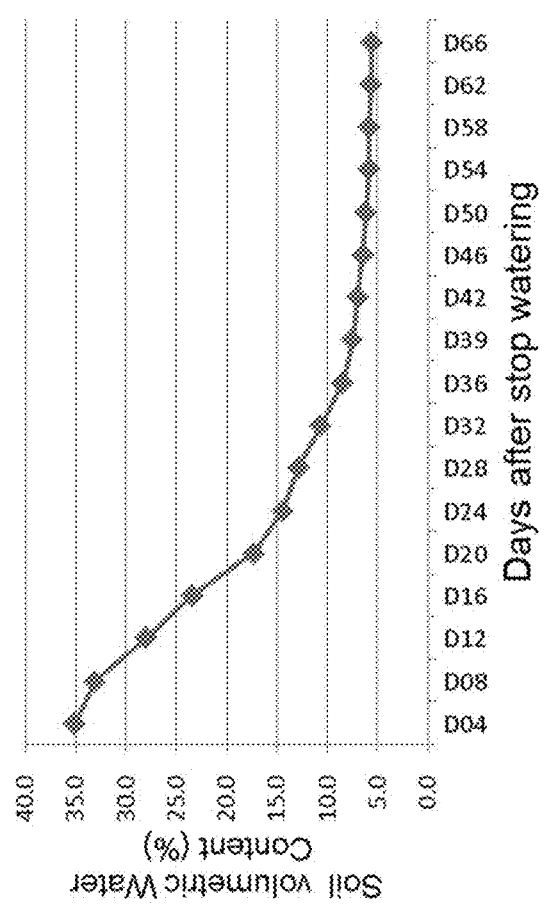

FIG. 10 shows changes of soil volumetric water content at different developmental stage for drought testing OsCAM2 transgenic rice in the second experiment. The OsCAM2 transgenic rice started heading at 24 days after stopping watering.

Figure 11:
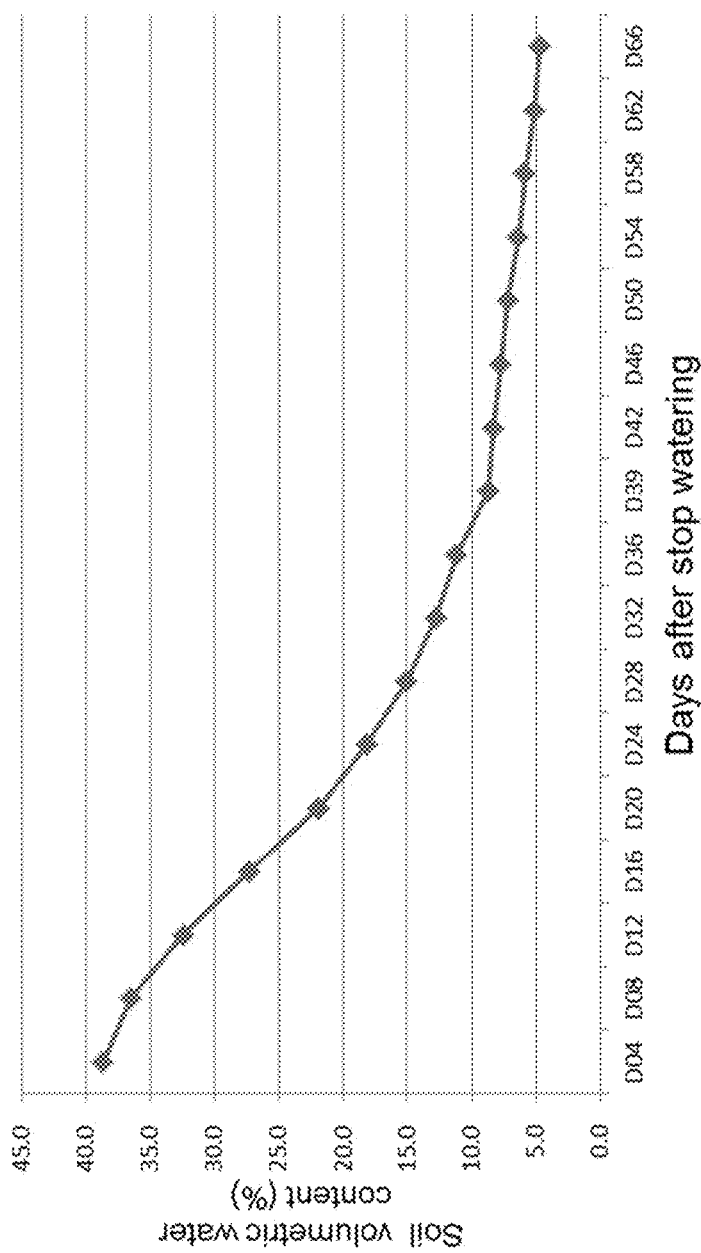

FIG. 11 shows changes of soil volumetric water content at different developmental stage for drought testing OsLecRK4.1 transgenic rice. The OsLecRK4.1 transgenic rice started heading at 22 days after stopping watering.

Figure 12:
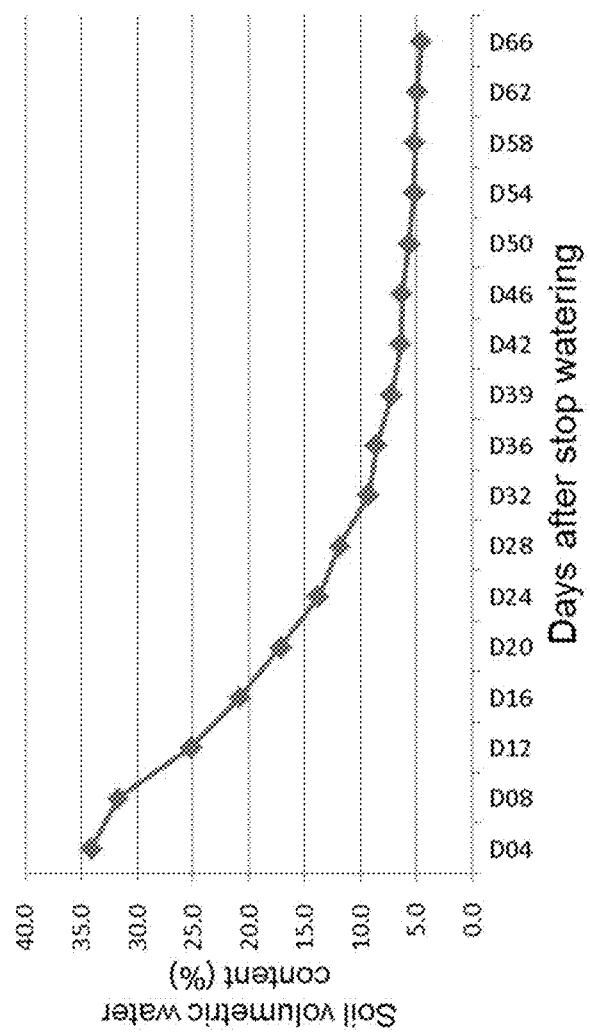

FIG. 12 shows changes of soil volumetric water content at different developmental stage for drought testing OsLecRK4.2 transgenic rice. The OsLecRK4.2 transgenic rice started heading at 25 days after stopping watering.

Table 1. SEQ ID NOs for nucleotide and amino acid sequences provided in the sequence listing Table 2. Rice gene names, Gene IDs (from TIGR) and Construct IDs Table 3. Primers for cloning rice drought tolerance genes Table 4. PCR reaction mixture for cloning drought tolerance genes Table 5. PCR cycle conditions Table 6. Enhanced drought tolerance of OsGSTU41 transgenic rice plants under greenhouse conditions ($1^{st}$ experiment)

Table 7. Enhanced drought tolerance of OsGSTU41 transgenic rice plants under greenhouse conditions at construct level (2nd experiment)

Table 8. Enhanced drought tolerance of OsGSTU41 transgenic rice plants under greenhouse conditions at line level (2nd experiment)

Table 9. Enhanced drought tolerance of OsPPCK4 transgenic rice plants under greenhouse conditions (1st experiment)

Table 10. Enhanced drought tolerance of OsPPCK4 transgenic rice plants under greenhouse conditions at construct level (2nd experiment)

Table 11. Enhanced drought tolerance of OsPPCK4 transgenic rice plants under greenhouse conditions at transgenic line level (2nd experiment)

Table 12. Enhanced drought tolerance of OsCAM2 transgenic rice plants under greenhouse conditions (1st experiment)

Table 13. Enhanced drought tolerance of OsCAM2 transgenic rice plants under greenhouse conditions at construct level (2nd experiment)

Table 14. Enhanced drought tolerance of OsCAM2 transgenic rice plants under greenhouse conditions at line level (2nd experiment)

Table 15. Enhanced drought tolerance of OsCAM2 transgenic rice plants under greenhouse conditions at line level (3rd experiment)

Table 16. Enhanced drought tolerance of OsCAM2 transgenic rice plants under greenhouse conditions at line level (3rd experiment)

Table 17. Drought tolerance assay of OsDN-DTP4 transgenic rice plants under greenhouse conditions (1st experiment)

Table 18. Drought tolerance assay of OsDN-DTP4 transgenic rice plants under greenhouse conditions at construct level (2nd experiment)

Table 19. Drought tolerance assay of OsDN-DTP4 transgenic rice plants under greenhouse conditions at line level (2nd experiment)

Table 20. Drought tolerance assay of OsDN-DTP4 transgenic rice plants under greenhouse conditions at construct level (3rd experiment)

Table 21. Drought tolerance assay of OsDN-DTP4 transgenic rice plants under greenhouse conditions at line level (3rd experiment)

Table 22. Grain yield analysis of OsGSTU41 transgenic rice plants under field drought conditions (1st experiment)

Table 23. Grain yield analysis of OsGSTU41 transgenic rice plants under field drought conditions (2nd experiment)

Table 24. Grain yield analysis of OsPPCK4 transgenic rice plants under field drought conditions Table 25. Grain yield assay of OsCAM2 transgenic rice plants under field drought conditions (1st experiment)

Table 26. Grain yield assay of OsCAM2 transgenic rice plants under field drought conditions (2nd experiment)

Table 27. Grain yield analysis of OsLecRK4.1 transgenic rice plants under field drought conditions Table 28. Grain yield analysis of OsLecRK4.2 transgenic rice plants under field drought conditions Table 29. Paraquat tolerance assay of OsGSTU41 transgenic rice plants at transgenic line level (1st experiment)

Table 30. Paraquat tolerance assay of OsGSTU41 transgenic rice plants at transgenic line level (2nd experiment)

Table 31. Paraquat tolerance assay of OsPPCK4 transgenic rice plants at transgenic line level (1st experiment)

Table 32. Paraquat tolerance assay of OsPPCK4 transgenic rice plants at transgenic line level (2nd experiment)

Table 33. Paraquat tolerance assay of OsPPCK4 transgenic rice plants at transgenic line level (3rd experiment)

Table 34. Paraquat tolerance assay of OsCAM2 transgenic rice plants at transgenic line level (1st experiment)

Table 35. Paraquat tolerance assay of OsCAM2 transgenic rice plants at transgenic line level (2nd experiment)

Table 36. Paraquat tolerance assay of OsDN-DTP4-transgenic rice plant at transgenic line level (1st experiment)

Table 37. Paraquat tolerance assay of OsDN-DTP4 transgenic rice plant at transgenic line level (2nd experiment)

Table 38. Paraquat tolerance assay of OsLecRK4.1 transgenic rice plant at transgenic line level (1st experiment)

Table 39. Paraquat tolerance assay of OsLecRK4.1 transgenic rice plant at transgenic line level (2nd experiment)

Table 40. Paraquat tolerance assay of OsLecRK4.2 transgenic rice plant at transgenic line level (1st experiment)

Table 41. Paraquat tolerance assay of OsLecRK4.2 transgenic rice plant at transgenic line level (2nd experiment)

TABLE 1

SEQ ID NOs for nucleotide and amino acid sequences provided in the sequence listing

| Source Species | Clone Designation | SEQ ID NO: (Nucleotide) | SEQ ID NO: (Amino Acid) |
|---|---|---|---|
| Artificial | DP0005 vector | 1 | n/a |
| Artificial | DsRed expression | 2 | n/a |
| Oryza sativa | OsGSTU41 | 3, 4 | 5 |
| Oryza sativa | OsPPCK4 | 6, 7 | 8 |
| Oryza sativa | OsCAM2 | 9, 10 | 11 |
| Oryza sativa | OsDN-DTP4 | 12, 13 | 14 |
| Oryza sativa | OsLecRK4.1 | 15, 16 | 17 |
| Oryza sativa | OsLecRK4.2 | 18, 19 | 20 |
| Artificial | Primers | 21-42 | n/a |

The Sequence Listing contains the one-letter code for nucleotide sequences and the three-letter code for amino acid sequences as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R.§ 1.822.

SEQ ID NO: 1 is the nucleotide sequence of vector DP0005.

SEQ ID NO: 2 is the nucleotide sequence of DsRed expression cassette.

SEQ ID NO: 3 is the nucleotide sequence of cDNA of OsGSTU41 gene.

SEQ ID NO: 4 is the nucleotide sequence of CDS of OsGSTU41 gene.

SEQ ID NO: 5 is the amino acid sequence of OsGSTU41.

SEQ ID NO: 6 is the nucleotide sequence of cDNA of OsPPCK4 gene.

SEQ ID NO: 7 is the nucleotide sequence of CDS of OsPPCK4 gene.

SEQ ID NO: 8 is the amino acid sequence of OsPPCK4.

SEQ ID NO: 9 is the nucleotide sequence of cDNA of OsCAM2 gene.

SEQ ID NO: 10 is the nucleotide sequence of CDS of OsCAM2 gene.

SEQ ID NO: 11 is the amino acid sequence of OsCAM2.

SEQ ID NO: 12 is the nucleotide sequence of gDNA of OsDN-DTP4 gene.

SEQ ID NO: 13 is the nucleotide sequence of CDS of OsDN-DTP4 gene.

SEQ ID NO: 14 is the amino acid sequence of OsDN-DTP4.

SEQ ID NO: 15 is the nucleotide sequence of gDNA of OsLecRK4.1 gene.

SEQ ID NO: 16 is the nucleotide sequence of CDS of OsLecRK4.1 gene.

SEQ ID NO: 17 is the amino acid sequence of OsLecRK4.1.

SEQ ID NO: 18 is the nucleotide sequence of gDNA of OsLecRK4.2 gene.

SEQ ID NO: 19 is the nucleotide sequence of CDS of OsLecRK4.2 gene.

SEQ ID NO: 20 is the amino acid sequence of OsLecRK4.2.

SEQ ID NO: 21 is forward primer for cloning cDNA of OsGSTU41 gene.

SEQ ID NO: 22 is reverse primer for cloning cDNA of OsGSTU41 gene.

SEQ ID NO: 23 is forward primer for cloning cDNA of OsPPCK4 gene.

SEQ ID NO: 24 is reverse primer for cloning cDNA of OsPPCK4 gene.

SEQ ID NO: 25 is forward primer for cloning cDNA of OsCAM2 gene.

SEQ ID NO: 26 is reverse primer for cloning cDNA of OsCAM2 gene.

SEQ ID NO: 27 is forward primer for cloning gDNA of OsDN-DTP4 gene.

SEQ ID NO: 28 is reverse primer for cloning gDNA of OsDN-DTP4 gene.

SEQ ID NO: 29 is forward primer for cloning gDNA of OsLecRK4.1 gene.

SEQ ID NO: 30 is reverse primer for cloning gDNA of OsLecRK4.1 gene.

SEQ ID NO: 31 is forward primer for cloning gDNA of OsLecRK4.2 gene.

SEQ ID NO: 32 is reverse primer for cloning gDNA of OsLecRK4.2 gene.

SEQ ID NO: 33 is forward primer for real-time RT-PCR analysis of OsGSTU41 gene.

SEQ ID NO: 34 is reverse primer for real-time RT-PCR analysis of OsGSTU41 gene.

SEQ ID NO: 35 is forward primer for real-time RT-PCR analysis of OsPPCK4 gene.

SEQ ID NO: 36 is reverse primer for real-time RT-PCR analysis of OsPPCK4 gene.

SEQ ID NO: 37 is forward primer for real-time RT-PCR analysis of OsDN-DTP4 gene.

SEQ ID NO: 38 is reverse primer for real-time RT-PCR analysis of OsDN-DTP4 gene.

SEQ ID NO: 39 is forward primer for real-time RT-PCR analysis of OsLecRK4.1 gene.

SEQ ID NO: 40 is reverse primer for real-time RT-PCR analysis of OsLecRK4.1 gene.

SEQ ID NO: 41 is forward primer for real-time RT-PCR analysis of OsLecRK4.2 gene.

SEQ ID NO: 42 is reverse primer for real-time RT-PCR analysis of OsLecRK4.2 gene.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

As used herein:

The term "OsGSTU41 (glutathione S-transferase TAU41)" refers to a rice polypeptide that confers drought tolerance and paraquat tolerance phenotype and is encoded by the rice gene locus LOC_Os01g72160.1. "GSTU41 polypeptide" refers herein to the OsGSTU41 polypeptide and its homologs from other organisms.

The OsGSTU41 polypeptide (SEQ ID NO: 5) is encoded by the coding sequence (CDS) (SEQ ID NO: 4) or nucleotide sequence (SEQ ID NO: 3) at rice gene locus LOC_Os01g72160.1. This polypeptide is annotated as "glutathione S-transferase, putative, expressed" in TIGR.

The term "OsPPCK4 (phosphoenolpyruvate carboxylase kinase 4)" refers to a rice polypeptide that confers drought tolerance and paraquat tolerance phenotype and is encoded by the rice gene locus LOC_Os02g56310.1. "PPCK4 polypeptide" refers herein to the OsPPCK4 polypeptide and its homologs from other organisms.

The OsPPCK4 polypeptide (SEQ ID NO: 8) is encoded by the coding sequence (CDS) (SEQ ID NO: 7) or nucleotide sequence (SEQ ID NO: 6) at rice gene locus LOC_Os02g56310.1. This polypeptide is annotated as "calcium-dependent protein kinase isoform AK1, putative, expressed" in TIGR and "putative phosphoenolpyruvate carboxylase kinase" in NCBI (on the world web at ncbi.nlm.nih.gov).

The term "OsCAM2 (Calmodulin 2)" refers to a rice polypeptide that confers drought tolerance and paraquat tolerance and is encoded by the rice gene locus LOC_Os05g41210.1. "CAM2 polypeptide" refers herein to the OsCAM2 polypeptide and its homologs from other organisms.

The OsCAM2 polypeptide (SEQ ID NO: 11) is encoded by the coding sequence (CDS) (SEQ ID NO: 10) or nucleotide sequence (SEQ ID NO: 9) at rice gene locus LOC_Os05g41210.1. This polypeptide is annotated as "Oscam2-Calmodulin, expressed" in TIGR.

The term "OsDN-DTP4 (drought tolerance protein 4)" refers to a rice polypeptide that confers drought tolerance and pataquat tolerance phenotype and is encoded by the rice gene locus LOC_Os07g04720.1. "DN-DTP4 polypeptide" refers herein to the OsDN-DTP4 polypeptide and its homologs from other organisms.

The OsDN-DTP4 polypeptide (SEQ ID NO: 14) is encoded by the coding sequence (CDS) (SEQ ID NO: 13) or nucleotide sequence (SEQ ID NO: 12) at rice gene locus LOC_Os07g04720.1. This polypeptide is annotated as "expressed protein" in TIGR.

The term "OsLecRK4.1 (lectin-like receptor kinase 4.1)" refers to a rice polypeptide that confers drought tolerance and paraquat tolerance and is encoded by the rice gene locus LOC_Os04g44900.1. "LecRK4.1 polypeptide" refers herein to the OsLecRK4.1 polypeptide and its homologs from other organisms.

The OsLecRK4.1 polypeptide (SEQ ID NO: 17) is encoded by the coding sequence (CDS) (SEQ ID NO: 16) or nucleotide sequence (SEQ ID NO: 15) at rice gene locus LOC_Os04g44900.1. This polypeptide is annotated as "lectin-like receptor kinase, putative, expressed" in TIGR.

The term "OsLecRK4.2 (lectin-like receptor kinase 4.2)" refers to a rice polypeptide that confers drought and paraquat tolerance and is encoded by the rice gene locus LOC_Os04g44910.1. "LecRK4.2 polypeptide" refers herein to the OsLecRK4.2 polypeptide and its homologs from other organisms.

The OsLecRK4.2 polypeptide (SEQ ID NO: 20) is encoded by the coding sequence (CDS) (SEQ ID NO: 19) or nucleotide sequence (SEQ ID NO: 18) at rice gene locus LOC_Os04g44910.1. This polypeptide is annotated as "receptor like protein kinase, putative, expressed" in TIGR.

The terms "monocot" and "monocotyledonous plant" are used interchangeably herein. A monocot of the current disclosure includes plants of the Gramineae family.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore represents a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

The term "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar or nitrogen concentrations, or by the observation of the expression level of a gene or genes, or by agricultural observations such as osmotic stress tolerance or yield.

"Agronomic characteristic" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

Increased biomass can be measured, for example, as an increase in plant height, plant total leaf area, plant fresh weight, plant dry weight or plant seed yield, as compared with control plants.

The ability to increase the biomass or size of a plant would have several important commercial applications. Crop cultivars may be developed to produce higher yield of the vegetative portion of the plant, to be used in food, feed, fiber, and/or biofuel.

Increased leaf size may be of particular interest. Increased leaf biomass can be used to increase production of plant-derived pharmaceutical or industrial products. Increased tiller number may be of particular interest and can be used to increase yield. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including drought or nutrient deprivation, because larger roots may better reach or take up water or nutrients.

For some ornamental plants, the ability to provide larger varieties would be highly desirable. For many plants, including fruit-bearing trees, trees that are used for lumber production, or trees and shrubs that serve as view or wind screens, increased stature provides improved benefits, such as in the forms of greater yield or improved screening.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed.

"Genome" as it applies to plant cells encompasses not only chromosomal DNA found within the nucleus, but also organelle DNA found within subcellular components (e.g., mitochondria, plastid) of the cell.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide.

For example, the heterologous polynucleotide is stably integrated within the genome such that the polynucleotide is passed on to successive generations. The heterologous polynucleotide may be integrated into the genome alone or as part of a recombinant DNA construct. A $T_0$ plant is directly recovered from the transformation and regeneration process. Progeny of $T_0$ plants are referred to as $T_1$ (first progeny generation), $T_2$ (second progeny generation), etc.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases. Nucleotides (usually found in their 5'-monophosphate form) are referred to by their single-letter designation as follows: "A" for adenylate or deoxyadenylate, "C" for cytidylate or deoxycytidylate, and "G" for guanylate or deoxyguanylate for RNA or DNA, respectively; "U" for uridylate; "T" for deoxythymidylate; "R" for purines (A or G); "Y" for pyrimidines (C or T); "K" for G or T; "H" for A or C or T; "I" for inosine; and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, and sulfation, gamma-carboxylation of glutamic acid residues, hydroxylation and ADP-ribosylation.

"Messenger RNA (mRNA)" refers to the RNA which has no intron and can be translated into protein by the cell.

"cDNA" refers to a DNA that is complementary to and synthesized from an mRNA template using reverse transcriptase. The cDNA can be single-stranded or converted into the double-stranded form using the Klenow fragment of DNA polymerase I.

"Mature" protein refers to a post-translation processed polypeptide; i.e., any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterogonous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and influencing the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription of genes in plant cells whether or not its origin is from a plant cell.

"Tissue-specific promoter" and "tissue-preferred promoter" may refer to a promoter that is expressed predominantly but not necessarily exclusively in one tissue or organ, but that may also be expressed in one specific cell or cell type.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristic or characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

An "allele" is one of two or more alternative forms of a gene occupying a given locus on a chromosome. When the alleles present at a given locus on a pair of homologous chromosomes in a diploid plant are the same, that plant is homozygous at that locus. If the alleles present at a given locus on a pair of homologous chromosomes in a diploid plant differ, that plant is heterozygous at that locus. If a transgene is present on one of a pair of homologous chromosomes in a diploid plant, that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels. (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel. (1992) *Plant Phys.* 100:1627-1632). A "mitochondrial signal peptide" is an amino acid sequence which directs a precursor protein into the mitochondria (Zhang and Glaser. (2002) *Trends Plant Sci* 7:14-21).

Methods to determine the relationship of various polynucleotide and polypeptide sequences are known. As used herein, "reference sequence" is a defined sequence used as a basis for sequence comparison. A reference sequence may be a subset or the entirety of a specified sequence, such as a segment of a full-length cDNA or gene sequence, or may be the complete cDNA or gene sequence. As used herein, "comparison window" makes reference to a contiguous and specified segment of a polynucleotide or polypeptide sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100 or longer. Those of skill in the art understand that to avoid a high similarity to a reference sequence due to inclusion of gaps in the sequence, a gap penalty is typically introduced and is subtracted from the number of matches.

The determination of percent sequence identity between any two sequences can be accomplished using a mathematical algorithm. Examples of such mathematical algorithms for sequence comparison include the algorithm of Myers and Miller. (1988) *CABIOS* 4:11-17; the local alignment algorithm of Smith, et al. (1981) *Adv. Appl. Math.* 2:482; the global alignment algorithm of Needleman and Wunsch. (1970) *J. Mol. Biol.* 48:443-453; the search-for-local alignment method of Pearson and Lipman. (1988) *Proc. Natl. Acad. Sci.* 85:2444-2448; the algorithm of Karlin and Altschul. (1990) *Proc. Natl. Acad. Sci. USA* 872264, modified as in Karlin and Altschul. (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package, Version 10 (available from Accelrys Inc., 9685 Scranton Road, San Diego, Calif., USA); and the Megalign® program of the LASERGENE® bioinformatics computing suite (DNASTAR® Inc., Madison, Wis.).

Alignments using these programs can be performed using the default parameters. The CLUSTAL program is well described by Higgins, et al. (1988) *Gene* 73:237-244; Higgins, et al. (1989) *CABIOS* 5:151-153; Corpet, et al. (1988) *Nucleic Acids Res.* 16:10881-10890; Huang, et al. (1992) *CABIOS* 8:155-165 and Pearson, et al. (1994) *Meth. Mol. Biol.* 24:307-331. The ALIGN program is based on the algorithm of Myers and Miller, (1988) supra. A PAM120 weight residue table, a gap length penalty of 12 and a gap penalty of 4 can be used with the ALIGN program when comparing amino acid sequences. The BLAST programs of Altschul, et al. (1990) *J. Mol. Biol.* 215:403 are based on the algorithm of Karlin and Altschul. (1990) supra. BLAST nucleotide searches can be performed with the BLASTN program, score=100, wordlength=12, to obtain nucleotide sequences homologous to a nucleotide sequence encoding a protein of the disclosures. BLAST protein searches can be performed with the BLASTX program, score=50, wordlength=3, to obtain amino acid sequences homologous to a protein or polypeptide of the disclosures. To obtain gapped alignments for comparison purposes, Gapped BLAST (in BLAST 2.0) can be utilized as described in Altschul, et al. (1997) *Nucleic Acids Res.* 25:3389. Alternatively, PSI-BLAST (in BLAST 2.0) can be used to perform an iterated search that detects distant relationships between molecules (Altschul, et al. (1997) supra). When utilizing BLAST, Gapped BLAST, PSI-BLAST and the default parameters of the respective programs (e.g., BLASTN for nucleotide sequences, BLASTX for proteins) can be used (the National Center for Biotechnology Information of the National Library of Medicine of the National Institutes of Health of the U.S. government). Alignment may also be performed by manual inspection.

Paired sequence identity/similarity values can be obtained using GAP Version 10 with the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch. (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (Henikoff and Henikoff. (1989) *Proc. Natl. Acad. Sci. USA* 89:10915).

Unless stated otherwise, multiple alignments of the sequences provided herein are performed using the Clustal V method of alignment (Higgins and Sharp. (1989) *CABIOS.* 5:151-153) with the default parameters (GAP PENALTY=10, GAP LENGTH PENALTY=10). Default parameters for pairwise alignments and calculation of percent identity of amino acid sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Embodiments include isolated polynucleotides and polypeptides, and recombinant DNA constructs useful for conferring drought tolerance; compositions (such as plants or seeds) comprising these recombinant DNA constructs; and methods utilizing these recombinant DNA constructs.

Isolated Polynucleotides and Polypeptides:

The present disclosure includes the following isolated polynucleotides and polypeptides:

An isolated polynucleotide comprising: (i) a nucleic acid sequence encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 5, 8, 11, 14, 17 or 20; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. Over-expression of the encoded polypeptide increases drought tolerance, and/or paraquat tolerance activity in plant.

An isolated polypeptide having an amino acid sequence of at least 50%, 51%, 52%, 53%, 54%, 55%, 56%, 57%, 58%, 59%, 60%, 61%, 62%, 63%, 6.4%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 5, 8, 11, 14, 17 or 20. The polypeptide is preferably a drought tolerance polypeptide. Over-expression of the polypeptide increases drought tolerance, and/or paraquat tolerance activity in plant.

An isolated polynucleotide comprising (i) a nucleic acid sequence of at least 50%, 51%, 52%, 53%, 5.4%, 55%, 56%, 57%, 58%, 59%, 60%, 61%, 62%, 63%, 6.4%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16 or 19; (ii) a nucleic acid sequence of at least 50%, 51%, 52%, 53%, 54%, 55%, 56%, 57%, 58%, 59%, 60%, 61%, 62%, 63%, 6.4%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3, 6, 9, 12, 15 or 18; or (iii) a full complement of the nucleic acid sequence of (i) or (ii). Any of the foregoing isolated polynucleotides may be utilized in any recombinant DNA constructs of the present disclosure. The isolated polynucleotide preferably encodes a drought tolerance polypeptide. Over-expression of the polypeptide improves drought tolerance and/or paraquat tolerance activity in plant.

Recombinant DNA Constructs:

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 5, 8, 11, 14, 17 or 20; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16 or 19; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3, 6, 9, 12, 15 or 18; or (iii) a full complement of the nucleic acid sequence of (i) or (ii).

In another embodiment, a recombinant DNA construct comprises a polynucleotide operably linked to at least one regulatory sequence (e.g., a promoter functional in a plant), wherein said polynucleotide encodes a drought tolerance polypeptide. The polypeptide preferably has drought tolerance and/or paraquat tolerance activity. The polypeptide may be from, for example, *Oryza sativa*, *Oryza australiensis*, *Oryza barthii*, *Oryza glaberrima* (African rice), *Oryza latifolia*, *Oryza longistaminata*, *Oryza meridionalis*, *Oryza officinalis*, *Oryza punctata*, *Oryza rufipogon* (brownbeard or red rice), *Oryza nivara* (Indian wild rice), *Arabidopsis thaliana*, *Zea mays*, *Glycine max*, *Glycine tabacina*, *Glycine soja* or *Glycine tomentella*.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive of, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (for example, U.S. Pat. No. 5,107,065). The complementarity of an antisense RNA may be with respect to any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on over-expression of a nucleic acid sequence having homology to a native mRNA, in the sense orientation, which results in the reduction of all RNA having homology to the over-expressed sequence (Vaucheret et al. (1998) *Plant J.* 16:651-659; and Gura. (2000) *Nature* 404:804-808).

RNA interference (RNAi) refers to the process of sequence-specific post-transcriptional gene silencing (PTGS) in animals mediated by short interfering RNAs (siRNAs) (Fire et al. (1998) *Nature* 391:806). The corresponding process in plants is commonly referred to as PTGS or RNA silencing and is also referred to as quelling in fungi. The process of PTGS is thought to be an evolutionarily-conserved cellular defense mechanism used to prevent the expression of foreign genes and is commonly shared by diverse flora and phyla (Fire et al. (1999) *Trends Genet.* 15:358).

Small RNAs play an important role in controlling gene expression, for example, small RNAs regulate many developmental processes which include flowering. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to 24 nucleotides (nt) in length that have been identified in both animals and plants (Lagos-Quintana et al. (2001) *Science* 294:853-858, Lagos-Quintana et al. (2002) *Curr. Biol.* 12:735-739; Lau et al. (2001) *Science* 294:858-862; Lee and Ambros. (2001) *Science* 294:862-864; Llave et al. (2002) *Plant Cell* 14:1605-1619; Mourelatos et al. (2002) *Genes Dev.* 16:720-728; Park et al. (2002)*Curr. Biol.* 12:1484-1495; Reinhart et al. (2002) *Genes Dev.* 16: 1616-1626). They are processed from longer precursor transcripts that range in size from approximately 70 to 200 nt, and these precursor transcripts have the ability to form stable hairpin structures.

miRNAs appear to regulate target genes by binding to complementary sequences located in the transcripts produced by these genes. It seems likely that miRNAs can enter at least two pathways of target gene regulation: (1) translational inhibition; and (2) RNA cleavage. miRNAs entering the RNA cleavage pathway are analogous to the 21-25 nt siRNAs generated during RNAi in animals and PTGS in plants, and likely are incorporated into an RNA-induced silencing complex (RISC) that is similar or identical to that seen for RNAi.

Regulatory Sequences:

A recombinant DNA construct of the present disclosure may comprise at least one regulatory sequence.

A regulatory sequence may be a promoter.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High-level, constitutive expression of the candidate gene under control of the 35S or UBI promoter may have pleiotropic effects, although candidate gene efficacy may be estimated when driven by a constitutive promoter. Use of tissue-specific and/or stress-induced promoters may eliminate undesirable effects but retain the ability to enhance drought tolerance. This effect has been observed in *Arabidopsis* (Kasuga et al. (1999) *Nature Biotechnol.* 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

Many leaf-preferred promoters are known in the art (Yamamoto et al. (1997) *Plant J.* 12(2):255-265; Kwon et al. (1994) *Plant Physiol.* 105:357-367; Yamamoto et al. (1994) *Plant Cell Physiol.* 35(5):773-778; Gotor et al. (1993) *Plant J.* 3:509-518; Orozco et al. (1993) *Plant Mol. Biol.* 23(6): 1129-1138; and Matsuoka et al. (1993) *Proc. Natl. Acad. Sci. USA* 90(20):9586-9590).

Promoters which are seed or embryo-specific and may be useful in the disclosure include soybean Kunitz trypsin inhibitor (Kti3, Jofuku and Goldberg. (1989) *Plant Cell* 1:1079-1093), convicilin, vicilin, and legumin (pea cotyledons) (Rerie, W. G., et al. (1991) *Mol. Gen. Genet.* 259: 149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci.* 82:3320-3324), phytohemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564). Promoters of seed-specific genes operably linked to heterologous coding regions in chimeric gene constructions maintain their temporal and spatial expression pattern in transgenic plants. Such examples include *Arabidopsis* 2S seed storage protein gene promoter to express enkephalin peptides in *Arabidopsis* and *Brassica napus* seeds (Vanderkerckhove et al. (1989) *Bio/Technology* 7:L929-932), bean lectin and bean beta-phaseolin promoters to express luciferase (Riggs et al. (1989) *Plant Sci.* 63:47-57), and wheat glutenin promoters to express chloramphenicol acetyl transferase (Colot et al. (1987) *EMBO J* 6:3559-3564).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in certain embodiments include the following: 1) the stress-inducible promoter RD29A (Kasuga et al. (1999) *Nature Biotechnol.* 17:287-291); 2) the stress-inducible promoter Rab17 (Vilardell et al. (1991) *Plant Mol. Bio.* 17:985-993; Kamp Busk et al. (1997) *Plant J* 11(6): 1285-1295); 3) the barley promoter B22E whose expression is specific to the pedicel in developing maize kernels ("Primary Structure of a Novel Barley Gene Differentially Expressed in Immature Aleurone Layers". Klemsdal, S. S. et al. (1991) *Mol. Gen. Genet.* 228(1/2):9-16); and 4) maize promoter Zag2 ("Identification and molecular characterization of ZAG1, the maize homolog of the *Arabidopsis* floral homeotic gene AGAMOUS", Schmidt, R. J. et al. (1993) *Plant Cell* 5(7):729-737; "Structural characterization, chromosomal localization and phylogenetic evaluation of two pairs of AGAMOUS-like MADS-box genes from maize", Theissen et al. (1995) *Gene* 156(2):155-166; NCBI GenBank Accession No. X80206)). Zag2 transcripts can be detected 5 days prior to pollination to 7 to 8 days after pollination ("DAP"), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Ciml that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize led promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007).

Additional promoters for regulating the expression of the nucleotide sequences of the present disclosure in plants are stalk-specific promoters, including the alfalfa S2A promoter (GenBank Accession No. EF030816; Abrahams et al. (1995) *Plant Mol. Biol.* 27:513-528) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in certain embodiments of the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*; root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1 BIO promoter (WO06055487, published May 26, 2006), the CRWAQ81 (WO05035770, published Apr. 21, 2005) and the maize ZRP2.47 promoter (NCBI accession number: U38790; GI No. 1063664).

Recombinant DNA constructs of the present disclosure may also include other regulatory sequences, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol. Cell Biol.* 8:4395-4405; Callis et al. (1987) *Genes Dev.* 1:1183-1200).

Any plant can be selected for the identification of regulatory sequences and polypeptide genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, switchgrass, tangerine, tea, tobacco, tomato, triticale, turf, turnip, vine, watermelon, wheat, yams, and zucchini.

Compositions:

A composition of the present disclosure is a plant comprising in its genome any of the recombinant DNA constructs of the present disclosure (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds or rice seeds.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

The recombinant DNA construct may be stably integrated into the genome of the plant.

Particular embodiments include but are not limited to the following:

1. A transgenic plant (for example, a rice or maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 5, 8, 11, 14, 17 or 20, and wherein said plant exhibits increased drought tolerance and/or paraquat tolerance when compared to a control plant. The plant may further exhibit an alteration of at least one agronomic characteristic when compared to the control plant.

2. A transgenic plant (for example, a rice or maize or soybean plant) comprising in its genome a recombinant DNA construct comprising a polynucleotide operably linked to at least one regulatory sequence, wherein said polynucleotide encodes a drought tolerance polypeptide, and wherein said plant exhibits increased drought tolerance and/or paraquat tolerance when compared to a control plant. The plant may further exhibit an alteration of at least one agronomic characteristic when compared to the control plant.

3. A transgenic plant (for example, a rice or maize or soybean plant) comprising in its genome a recombinant DNA construct comprising a polynucleotide operably linked to at least one regulatory sequence, wherein said polynucleotide encodes a drought tolerance polypeptide, and wherein said plant exhibits an alteration of at least one agronomic characteristic when compared to a control plant.

4. Any progeny of the above plants in embodiment 1-3, any seeds of the above plants in embodiment 1-3, any seeds of progeny of the above plants in embodiment 1-3, and cells from any of the above plants in embodiment 1-3 and progeny thereof.

In any of the foregoing embodiment 1-4 or other embodiments, the drought tolerance polypeptide may be from *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara* (Indian wild rice), *Arabidopsis thaliana, Zea mays, Glycine max, Glycine tabacina, Glycine soja* or *Glycine tomentella*.

In any of the foregoing embodiment 1-4 or other embodiments, the recombinant DNA construct may comprise at least a promoter functional in a plant as a regulatory sequence.

In any of the foregoing embodiment 1-4 or other embodiments, the alteration of at least one agronomic characteristic is either an increase or decrease.

In any of the foregoing embodiment 1-4 or other embodiments, the at least one agronomic characteristic may be selected from the group consisting of greenness, grain yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress. For example, the alteration of at least one agronomic characteristic may be an increase in grain yield, greenness or biomass.

In any of the foregoing embodiment 1-4 or other embodiments, the plant may exhibit the alteration of at least one agronomic characteristic when compared, under water limiting conditions, to a control plant.

In any of the foregoing embodiment 1-4 or other embodiments, the plant may exhibit the alteration of at least one agronomic characteristic when compared, under oxidative stress (paraquat) conditions, to a control plant.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought without exhibiting substantial physiological or physical deterioration, and/or its ability to recover when water is restored following a period of drought.

"Drought tolerance activity" of a polypeptide indicates that over-expression of the polypeptide in a transgenic plant confers increased drought tolerance of the transgenic plant relative to a reference or control plant.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than would a control plant when water is restored following a period of drought.

"Environmental conditions" refer to conditions under which the plant is grown, such as the availability of water, availability of nutrients, or the presence of insects or disease.

"Paraquat" (1,1-dimethyl-4,4-bipyridinium dichloride), is a foliar-applied and non-selective bipyridinium herbicides, and causes photooxidative stress which further cause damage to plant or prevent its successful growth.

"Paraquat tolerance" is a trait of a plant, reflects the ability to survive and/or grow better when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

The Examples below describe some representative protocols and techniques for simulating drought conditions and/or evaluating drought tolerance; and simulating oxidative conditions.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to yield loss exhibited by a control or reference plant).

Parameters such as recovery degree, survival rate, paraquat tolerance rate, gene expression level, water use efficiency, level or activity of an encoded protein, and others are typically presented with reference to a control cell or control plant. A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration. One of ordinary skill in the art would readily recognize a suitable control or reference plant to be utilized when assessing or measuring an agronomic characteristic or phenotype of a transgenic plant using compositions or methods as described herein. For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct. The progeny not comprising the recombinant DNA construct is the control or reference plant.

2. Introgression of a recombinant DNA construct into an inbred line, such as in rice and maize, or into a variety, such as in soybean: the introgressed line would typically be measured relative to the parent inbred or variety line (i.e., the parent inbred or variety line is the control or reference plant).

3. Two hybrid lines, wherein the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity of nuclear genetic material compared to the plant comprising the recombinant DNA construct. There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

A control plant or plant cell may comprise, for example: (a) a wild-type (WT) plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimulus that would induce expression of the gene of interest or (e) the subject plant or plant cell itself, under conditions in which the gene of interest is not expressed. A control may comprise numerous individuals representing one or more of the categories above; for example, a collection of the non-transformed segregants of category "c" is often referred to as a bulk null.

In this disclosure, Line null, Bulk null, ZH11-TC and VC indicate control plants, Line null represents the control segregated from the corresponding hemizygous transgenic lines, Bulk null represents the bulk null which is a collection of the non-transformed segregants from the hemizygous transgenic lines, ZH11-TC represents rice plants generated from tissue cultured Zhonghua 11, and VC represents plants transformed with empty vector of DP0005 or DP0158.

Methods:

Methods include but are not limited to methods for increasing drought tolerance in a plant, methods for evaluating drought tolerance in a plant, methods for increasing paraquat tolerance, methods for altering an agronomic characteristic in a plant, methods for determining an alteration of an agronomic characteristic in a plant, and methods for producing seed. The plant may be a monocotyledonous or dicotyledonous plant, for example, rice, maize or soybean plant. The plant may also be sunflower, canola, wheat, alfalfa, cotton, barley, millet, sugar cane or sorghum. The seed may be a maize or soybean seed, for example, a maize hybrid seed or maize inbred seed.

Methods include but not limited to the following:

A method for transforming a cell comprising transforming a cell with any one or more of the isolated polynucleotides of the present disclosure, wherein, in particular embodiments, the cell is eukaryotic cell, e.g., a yeast, insect or plant cell; or prokaryotic cell, e.g., a bacterial cell.

A method for producing a transgenic plant comprising transforming a plant cell with any of the isolated polynucleotides or recombinant DNA constructs of the present disclosure and regenerating a transgenic plant from the transformed plant cell, wherein, the transgenic plant and the transgenic seed obtained by this method may be used in other methods of the present disclosure.

A method for isolating a polypeptide of the disclosure from a cell or culture medium of the cell, wherein the cell comprises a recombinant DNA construct comprising a polynucleotide of the disclosure operably linked to at least one regulatory sequence, and wherein the transformed host cell is grown under conditions that are suitable for expression of the recombinant DNA construct.

A method for altering the level of expression of a polypeptide of the disclosure in a host cell comprising: (a) transforming a host cell with a recombinant DNA construct of the present disclosure; and (b) growing the transformed host cell under conditions that are suitable for the expression of the recombinant DNA construct, wherein the expression of the recombinant DNA construct results in production of altered levels of the polypeptide of the disclosure in the transformed host cell.

A method of increasing drought tolerance and/or paraquat tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 5, 8, 11, 14, 17 or 20; (b) regenerating a transgenic plant from the regenerable plant cell after step (a), wherein the transgenic plant comprises in its genome the recombinant DNA construct and exhibits increased drought tolerance and/or paraquat tolerance when compared to a control plant; and further (c) obtaining a progeny plant derived from transgenic plant, wherein said progeny plant comprises in its genome the recombinant DNA construct and exhibits increased drought tolerance and/or paraquat tolerance when compared to a control plant.

A method of evaluating drought tolerance and/or paraquat tolerance in a plant comprising (a) obtaining a transgenic plant, which comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 5, 8, 11, 14, 17 or 20; (b) obtaining a progeny plant derived from said transgenic plant, wherein the progeny plant comprises in its genome the recombinant DNA construct; and (c) evaluating the progeny plant for drought tolerance and/or paraquat tolerance compared to a control plant.

A method of determining an alteration of an agronomic characteristic in a plant comprising (a) obtaining a transgenic plant which comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5, 8, 11, 14, 17 or 20; (b) obtaining a progeny plant derived from said transgenic plant, wherein the progeny plant comprises in its genome the recombinant DNA construct; and (c) determining whether the progeny plant exhibits an alteration in at least one agronomic characteristic when compared, optionally under water limiting conditions, to a control plant.

A method of producing seed comprising any of the preceding methods, and further comprising obtaining seeds from said progeny plant, wherein said seeds comprise in their genome said recombinant DNA construct.

In any of the preceding methods or any other embodiments of methods of the present disclosure, in said introducing step, the said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise the following: (i) culturing said transformed plant cells in a medium comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the step of determining an alteration of an agronomic characteristic in a transgenic plant, if applicable, may comprise determining whether the transgenic plant exhibits an alteration of at least one agronomic characteristic when compared, under varying environmental conditions, to a control plant not comprising the recombinant DNA construct.

In any of the preceding methods or any other embodiments of methods of the present disclosure, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding methods or any other embodiments of methods of the present disclosure, the plant may exhibit the alteration of at least one agronomic characteristic when compared, under water limiting conditions, to a control plant.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation. Techniques for plant transformation and regeneration have been described in International Patent Publication WO 2009/006276, the contents of which are herein incorporated by reference.

In addition, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" engineered endonucleases such as meganucleases produced to modify plant genomes (e.g., WO 2009/114321; Gao et al. (2010) *Plant Journal* 1:176-187). Another site-directed engineering is through the use of zinc finger domain recognition coupled with the restriction properties of restriction enzyme (e.g., Urnov, et al. (2010) *Nat Rev Genet.* 11(9): 636-46; Shukla, et al. (2009) *Nature* 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326 (5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant containing a desired polypeptide is cultivated using methods well known to one skilled in the art.

EXAMPLES

The present disclosure is further illustrated in the following examples, in which parts and percentages are by weight and degrees are Celsius, unless otherwise stated. It should be understood that these examples, while indicating embodiments of the disclosure, are given by way of illustration only. From the above discussion and these examples, one skilled in the art can ascertain the essential characteristics of this disclosure, and without departing from the spirit and scope thereof, can make various changes and modifications of the disclosure to adapt it to various usages and conditions. Furthermore, various modifications of the disclosure in addition to those shown and described herein will be apparent to those skilled in the art from the foregoing description. Such modifications are also intended to fall within the scope of the appended claims.

Example 1

Drought Tolerance Genes Cloning and Over-Expression Vector Construction

Based on our preliminary screening of rice activation tagging population and the sequence information of gene IDs shown in Table 2, primers were designed for cloning rice abiotic stress tolerance genes OsGSTU41, OsPPCK4, OsCAM2, OsDN-DTP4, OsLecRK4.1 and OsLecRK4.2. The primers and the expected-lengths of the amplified genes are shown in Table 3.

For OsGSTU41, OsPPCK4 and OsCAM2, their cDNAs were cloned by using pooled cDNA from leaf, stem and root tissues of Zhonghua 11 plant as the template. For OsDN-DTP4, OsLecRK4.1, and OsLecRK4.2, their gDNAs were cloned, and amplified using genomic DNA of Zhonghua 11 as the template. The PCR reaction mixtures and PCR procedures are shown in Table 4 and Table 5.

TABLE 2

Rice gene names, Gene IDs (from TIGR) and Construct IDs

| Gene name | LOC ID | Construct ID |
|---|---|---|
| OsGSTU41 | LOC_Os01g72160 | DP0043 |
| OsPPCK4 | LOC_Os02g56310 | DP0058 |
| OsCAM2 | LOC_Os05g41210 | DP0059 |
| OsDN-DTP4 | LOC_Os07g04720 | DP0167 |
| OsLecRK4.1 | LOC_Os04g44900 | DP0173 |
| OsLecRK4.2 | LOC_Os04g44910 | DP0209 |

TABLE 3

Primers for cloning rice drought tolerance genes

| Primer | Sequence | SEQ ID NO: | Gene name | Length of amplified fragment (bp) |
|---|---|---|---|---|
| gc-371 | 5'-AAATGGTTAAGCTAATCAGCGCCTTC-3' | 21 | OsGSTU41 | 727 |
| gc-372 | 5'-TACGCATATTCCAGCATCGAAATTCAC-3' | 22 | | |
| DEgc-516 | 5'-GGAGAAGAGAATCGCGGAGATAGC-3' | 23 | OsPPCK4 | 760 |
| DEgc-517 | 5'-TGGAGTTCATCATCATCCTCGATC-3' | 24 | | |
| DEgc-546 | 5'-CTCGCGGAACCTTCTCGAAGCTTC-3' | 25 | OsCAM2 | 576 |
| DEgc-547 | 5'-CAGCTTTGTTGTAGGCCCTGAC-3' | 26 | | |
| gc-996 | 5'-GCGGCAAAAACGATGTCAGTGGCTAG-3' | 27 | OsDN-DTP4 | 1184 |
| gc-997 | 5'-GTCCCTTAACTATATAAAACCGGTCTCCC-3' | 28 | | |
| gc-1573 | 5'-ACCGGGGCCGTGACTTGACTGAC-3' | 29 | OsLecRK4.1 | 2346 |
| gc-1574 | 5'-CGTCGACAATCAGATCAGAGGAGAA-3' | 30 | | |
| gc-1578 | 5'-GTAGCGAGGAGTGTGAACGATGTGATGC-3' | 31 | OsLecRK4.2 | 2464 |
| gc-1579 | 5'-GCCTTCTCGAAGCTTTGCACACTCACTG-3' | 32 | | |

TABLE 4

PCR reaction mixture for cloning drought tolerance genes

| Reaction mix | 50 μL |
|---|---|
| Template | 1 μL |
| TOYOBO KOD-FX (1.0 U/μL) | 1 μL |
| 2 × PCR buffer for KOD-FX | 25 μL |
| 2 mMdNTPs (0.4 mM each) | 10 μL |
| Primer-F/R (10 μM) | 2 μL each |
| ddH$_2$O | 9 μL |

TABLE 5

PCR cycle conditions

| 94° C. | 3 min | |
|---|---|---|
| 98° C. | 10 s | |
| 58° C. | 30 s | ×30 |
| 68° C. | (1 Kb/min) 1 min | |
| 68° C. | 5 min | |

The PCR amplified products were extracted after the agarose gel electrophoresis using a column kit and then ligated with TA cloning vectors. The sequences and orientation in these constructs were confirmed by sequencing. Then these genes were cloned into plant binary construct DP0005 (pCAMBIA1300-AsRed) (SEQ ID NO: 1) or DP0158 which was generated by transferring DsRed gene expression cassette (SEQ ID NO: 2 in the sequence list) into construct DP0005.

OsGSTU41, OsPPCK4 and OsCAM2 were cloned into the construct of DP0005. The generated over-expression vectors were listed in Table 2. The cloned nucleotide sequence in construct of DP0043 and coding sequence of OsGSTU41 are provided as SEQ ID NO: 3 and 4, the encoded amino acid sequence of OsGSTU41 is shown in SEQ ID NO: 5; the cloned nucleotide sequence in construct of DP0058 and coding sequence of OsPPCK4 are provided as SEQ ID NO: 6 and 7, the encoded amino acid sequence of OsPPCK4 is shown in SEQ ID NO: 8; the cloned nucleotide sequence in construct of DP0059 and coding sequence of OsCAM2 are provided as SEQ ID NO: 9 and 10, the encoded amino acid sequence of OsCAM2 is shown in SEQ ID NO: 11.

OsDN-DTP4, OsLecRK4.1 and OsLecRK4.2 were cloned into the construct of DP0158. The cloned nucleotide sequence in construct of DP0167 and coding sequence of OsDN-DTP4 are provided as SEQ ID NO: 12 and 13, the encoded amino acid sequence of OsDN-DTP4 is shown in SEQ ID NO: 14; the cloned nucleotide sequence in construct of DP0173 and coding sequence of OsLecRK4.1 are provided as SEQ ID NO: 15 and 16, the encoded amino acid sequence of OsLecRK4.1 is shown in SEQ ID NO: 17; and the cloned nucleotide sequence in construct of DP0209 and coding sequence of OsLecRK4.2 are provided as SEQ ID NO: 18 and 19, the encoded amino acid sequence of OsLecRK4.2 is shown in SEQ ID NO: 20.

Example 2

Generation of Transgenic Rice Lines

The over-expression vectors and empty vectors (DP0005 and DP0158) were transformed into the Zhonghua 11 (*Oryza sativa* L.) by Agrobacteria-mediated method as described by Lin and Zhang ((2005) *Plant Cell Rep.* 23:540-547). Zhonghua 11 was cultivated by the Institute of Crop Sciences, Chinese Academy of Agricultural Sciences. The first batch of seeds used in this research was provided by Beijing Weiming Kaituo Agriculture Biotech Co., Ltd. Calli induced from embryos was transformed with Agrobacteria with the vector. The transgenic seedlings (T$_0$) generated in transformation laboratory are transplanted in the field to get T$_1$ seeds. The T$_1$ and T$_2$ seeds are stored at cold room (4° C.), and the T$_2$ seeds were used for following trait screening.

OsGSTU41, OsPPCK4 and OsCAM2 transgenic seeds did not show red color under green fluorescent light. The T$_1$ transgenic plants were selected by hygromycin by culturing the rice plants (from 1-2 cm in height) in 50 mg/L hygromycin solution, the survived plants (hygromycin-resistant) were planted in field to produce T$_2$ seeds. Only the hygromycin-resistant T$_2$ transgenic rice plants were used in trait screen.

OsDN-DTP4, OsLecRK4.1 and OsLecRK4.2 transgenic seeds which showed red color under green fluorescent light (transgenic seeds) were used in the following assays.

Example 3

Gene Expression Analysis

Transgene expression levels in the transgenic rice plants were analyzed. A standard RT-PCR or a real-time RT-PCR procedure, such as the QuantiTect® Reverse Transcription Kit from Qiagen® and Real Time-PCR (SYBR$^R$Premix Ex Taq™, TaKaRa), is used. EF-1α gene is used as an internal control to show that the amplification and loading of samples from the transgenic rice and wild-type are similar. Gene expression is normalized based on the EF-1α mRNA levels.

As shown in FIG. 3, the expression level of OsGSTU41 gene in DP0043.15 rice is set at 1.00, OsGSTU4/overexpressed in all the ten transgenic rice lines, while the expression of OsGSTU41 was not detected in ZH11-TC plants. The primers used for the real-time PCR are as below:

```
                                   (SEQ ID NO: 33)
DP0043-3:      5'-GGCTGTCGTTCTGGATGG-3'

(SEQ ID NO: 34)
DP0043-4:      5'-GCAGTGAACAAGGCGACG-3'
```

As shown in FIG. 4, the expression level of OsPPCK4 gene in ZH11-TC rice is set at 1.00, OsPPCK4 overexpressed in all the transgenic lines, while the expression levels of OsPPCK4 were very low in both ZH11-TC and DP0158 controls.

```
                                   (SEQ ID NO: 35)
DP0058-F1:     5'-GCTCTACATGATGCTCTCCG-3'

(SEQ ID NO: 36)
DP0058-R1:     5'-GAGACGTCCTTGCAGAGC-3'
```

The expression level of OsDN-DTP4 gene in ZH11-TC rice is set at 1.00, OsDN-DTP4 over-expressed in all the nine transgenic rice lines (FIG. 5).

```
                                   (SEQ ID NO: 37)
DP0167-F1:     5'-CCAGTTCAGAGTACGGTGCCG-3'

(SEQ ID NO: 38)
DP0167-R1:     5'-GTGTCCACGTCAGCCTCCTTTC-3'
```

The expression level of OsLecRK4.1 gene in ZH11-TC rice is set at 1.00, OsLecRK4.1 over-expressed in all the nine transgenic rice lines (FIG. 6).

```
                                   (SEQ ID NO: 39)
DP0173-F1:     5'-CGCTCAACATCTCATCCC-3'

(SEQ ID NO: 40)
DP0173-R1:     5'-CCGCATGAACACGAACAC-3'
```

As shown in FIG. 7, the expression level of OsLecRK4.2 gene in ZH11-TC rice is set at 1.00, OsGLRL1.2 overexpressed in all the transgenic lines, while the expression levels of OsLecRK4.2 were very low in ZH11-TC plants.

```
                                   (SEQ ID NO: 41)
DP0209-F1:     5'-CCGACGATGGTGAGCTAC-3'

(SEQ ID NO: 42)
DP0209-R1:     5'-GTGACGGTGGAAGGGAAG-3'
```

Example 4

Drought Screening of Transgenic Rice Plants

The transgenic rice plants were screened in greenhouse drought assays. Two types of lamps, i.e. sodium lamp and metal halide lamp with the ratio of 1:1, were provided as light source with a 16-h-light/8-h-dark cycle and placed approximately 1.5 m height above the seedbed. The light intensity 30 cm above the seedbed was measured as 10,000-20,000 lx in sunny day, while 6,000-10,000 lx in cloudy day, the relative humidity ranged from 30% to 90%, and the temperature ranged from 20 to 35° C.

Drought Screening Method:

$T_2$ Transgenic seeds were sterilized by 800 ppm carbendazol for 8 h at 32° C. and washed 3-5 times with distilled water, then soaked in water for 16 h at 32° C., germinated for 18 h at 35-37° C. in an incubator. The germinated seeds were sowed in one tray or pot filled with mixture of organic soil, vermiculite and sand (V:V:V=3:3:2). The seedlings were grown under normal greenhouse condition and watered by modified IRRI solution. When the seedlings grew to 3-leaf stage, watering was stopped and the trays were kept into a dry place until the leaves became dry and curved (approximately 9-15 days depending on the seasons). The trays were transferred into water pool to recover the seedlings for 5-7 days, and then the plants were scored for the recovery degree. The following scoring system was used: more than half green stem=1, more than two third green leaf=1, less than two third but more than one third green leaf=0.5, less than one third green leaf=0.2, no green leaf or less than half green stem=0. The recovery degree was the sum of the score of the green tissues, and the data were statistically analyzed using Mixed Model. The lines showed significant better than the controls (P<0.05) were considered as positive ones. Survival rate (percentage of survived plants over the total plant number) was also used as a parameter for drought screening.

Two experimental designs were used. (1) Latin Square Design was used, and the total 16 plants for each line grew into different positions of the tray. The wild-type control (Zhonghua 11) from tissue culture procedure (ZH11-TC) and/or empty vector (DP0158) transgenic control in the same tray were used as controls. Several positive control (a drought tolerant variety, Mianhui 501) and negative control (a drought sensitive variety, Dongbeiyin 2) seedlings also were planted in the same tray. (2) Randomized Block Design was used for confirming the observation of the transformed rice from construct level. Nine to twelve transgenic lines from the same construct were planted in one experimental unit to evaluate the transgene at construct level by Mixed Model considering construct, line and environment effects. If the survival rates or recovery degrees of the transgenic rice plants were significantly greater than that of control (P<0.05), the gene was considered as having drought tolerant function.

GH Drought Assay Results:

1) GH DRT Validation Results of OsGSTU41 (DP0043) Transgenic Rice

Ten OsGSTU41 transgenic lines were tested by Latin square design in the first experiment. Different lines were planted in different trays, and the ZH11-TC and DP0005 seedlings in the same tray were used as their corresponding controls. Table 6 shows that all of the ten lines exhibited higher survival rates and recovery degrees, and six lines showed significantly higher recovery degrees than ZH11-TC control. When compared with the DP0005 control, eight lines exhibited higher survival rates and average recovery degrees, and four lines showed significantly higher recovery degrees. These results demonstrate that OsGSTU41 transgenic rice had enhanced drought tolerance at seedling stage.

TABLE 6

Enhanced drought tolerance of OsGSTU41 transgenic rice plants under greenhouse conditions (1st experiment)

| Line ID | Number of survived plants | Number of total plants | Survival rate (%) | Average recovery degree | Pvalue | P ≤ 0.05 |
|---|---|---|---|---|---|---|
| DP0043.02 | 6 | 16 | 37.5 | 0.45 | 0.1373 | |
| ZH11-TC | 3 | 16 | 18.8 | 0.19 | | |
| DP0043.03 | 9 | 16 | 56.3 | 0.63 | 0.2394 | |
| ZH11-TC | 5 | 16 | 31.3 | 0.38 | | |
| DP0043.11 | 7 | 16 | 43.8 | 0.61 | 0.5978 | |
| ZH11-TC | 5 | 16 | 31.3 | 0.47 | | |
| DP0043.12 | 11 | 16 | 68.8 | 0.70 | 0.0004 | Y |
| ZH11-TC | 1 | 16 | 6.3 | 0.09 | | |
| DP0043.15 | 12 | 16 | 75.0 | 1.06 | 0.0007 | Y |
| ZH11-TC | 5 | 15 | 33.3 | 0.31 | | |

TABLE 6-continued

Enhanced drought tolerance of OsGSTU41 transgenic rice plants under greenhouse conditions (1st experiment)

| Line ID | Number of survived plants | Number of total plants | Survival rate (%) | Average recovery degree | Pvalue | P ≤ 0.05 |
|---|---|---|---|---|---|---|
| DP0043.19 | 10 | 16 | 62.5 | 0.66 | 0.4345 | |
| ZH11-TC | 5 | 12 | 41.7 | 0.50 | | |
| DP0043.25 | 12 | 16 | 75.0 | 1.38 | 0.0022 | Y |
| ZH11-TC | 5 | 14 | 35.7 | 0.47 | | |
| DP0043.26 | 14 | 16 | 87.5 | 0.99 | 0.0004 | Y |
| ZH11-TC | 2 | 13 | 15.4 | 0.16 | | |
| DP0043.28 | 14 | 16 | 87.5 | 1.19 | 0.0017 | Y |
| ZH11-TC | 4 | 16 | 25.0 | 0.37 | | |
| DP0043.29 | 13 | 16 | 81.3 | 1.59 | 0.0010 | Y |
| ZH11-TC | 8 | 15 | 53.3 | 0.76 | | |

In the second experiment, construct level design was used, and nine transgenic lines were tested. When grown to 3-leaf stage, the plants were first drought stressed for 17 days, recovered in water for six days, and then were drought stressed for 22 days and recovered for seven days. 69 of the 108 OsGSTU41 transgenic rice plants survived, while 9 of the 24 ZH11-TC and 5 of the 12 DP0158 seedlings survived. OsGSTU41 transgenic rice exhibited higher survival rate and average recovery degree than both ZH11-TC and DP0158 seedlings at the construct level (Table 7). Analysis at transgenic line level showed that eight lines exhibited higher survival rates and average recovery degrees than both controls (Table 8). These results indicate that OsGSTU41 transgenic rice showed enhanced drought tolerance at seedling stage, and OsGSTU41 plays a role in improving drought tolerance of transgenic plants.

TABLE 7

Enhanced drought tolerance of OsGSTU41 transgenic rice plants under greenhouse conditions at construct level (2nd experiment)

| Construct ID | Number of survived plants | Number of total plants | Survival rate (%) | Average recovery degree | P value | P ≤ 0.05 |
|---|---|---|---|---|---|---|
| DP0043 | 69 | 108 | 63.9 | 0.64 | 0.0426 | Y |
| ZH11-TC | 9 | 24 | 37.5 | 0.40 | | |
| DP0043 | 69 | 108 | 63.9 | 0.64 | 0.1615 | |
| DP0158 | 5 | 12 | 41.7 | 0.42 | | |

TABLE 8

Enhanced drought tolerance of OsGSTU41 transgenic rice plants under greenhouse conditions at line level (2nd experiment)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0043.06 | 3 | 12 | 25.0 | 0.52 | 0.3682 | | 0.5479 | |
| DP0043.11 | 9 | 12 | 75.0 | 0.69 | 0.0381 | Y | 0.1238 | |
| DP0043.12 | 6 | 12 | 50.0 | 0.60 | 0.1493 | | 0.3011 | |
| DP0043.13 | 9 | 12 | 75.0 | 0.68 | 0.0474 | Y | 0.1425 | |
| DP0043.15 | 7 | 12 | 58.3 | 0.63 | 0.1047 | | 0.2387 | |
| DP0043.19 | 8 | 12 | 66.7 | 0.65 | 0.0714 | | 0.1860 | |
| DP0043.24 | 8 | 12 | 66.7 | 0.65 | 0.0714 | | 0.1860 | |
| DP0043.26 | 9 | 12 | 75.0 | 0.68 | 0.0474 | Y | 0.1425 | |
| DP0043.28 | 10 | 12 | 83.3 | 0.70 | 0.0304 | Y | 0.1071 | |
| ZH11-TC | 9 | 24 | 37.5 | 0.40 | | | | |
| DP0158 | 5 | 12 | 41.7 | 0.42 | | | | |

2) GH DRT Validation Results of OsPPCK4 (DP0058) Transgenic Rice

Twelve OsPPCK4 transgenic lines were tested by drought stress, and planted in different trays in the first experiment. ZH11-TC plants in the same tray were used as their corresponding controls. Table 9 shows that ten lines exhibited higher survival rates and recovery degrees than that of ZH11-TC control, and five lines showed significantly higher recovery degrees, indicating that the OsPPCK4 transgenic rice plants had improved drought tolerance at seedling stage.

TABLE 9

Enhanced drought tolerance of OsPPCK4 transgenic rice plants under greenhouse conditions (1st experiment)

| Line ID | Number of survived plants | Number of total plants | Survival rate (%) | Average recovery degree | Pvalue | P ≤ 0.05 |
|---|---|---|---|---|---|---|
| DP0058.02 | 8 | 16 | 50.0 | 0.54 | 0.0119 | Y |
| ZH11-TC | 1 | 16 | 6.3 | 0.06 | | |
| DP0058.03 | 5 | 16 | 31.3 | 0.31 | 0.1701 | |
| ZH11-TC | 2 | 16 | 12.5 | 0.13 | | |
| DP0058.04 | 7 | 16 | 43.8 | 0.56 | 0.0219 | Y |
| ZH11-TC | 2 | 16 | 12.5 | 0.13 | | |
| DP0058.07 | 11 | 16 | 68.8 | 0.81 | 0.5165 | |
| ZH11-TC | 9 | 16 | 56.3 | 0.66 | | |
| DP0058.08 | 7 | 16 | 43.8 | 0.44 | 0.8143 | |
| ZH11-TC | 5 | 16 | 31.3 | 0.38 | | |

TABLE 9-continued

Enhanced drought tolerance of OsPPCK4transgenic rice plants under greenhouse conditions (1st experiment)

| Line ID | Number of survived plants | Number of total plants | Survival rate (%) | Average recovery degree | Pvalue | P ≤ 0.05 |
|---|---|---|---|---|---|---|
| DP0058.10 | 5 | 16 | 31.3 | 0.50 | 0.6151 | |
| ZH11-TC | 8 | 16 | 50.0 | 0.64 | | |
| DP0058.11 | 11 | 15 | 73.3 | 2.16 | 0.2430 | |
| ZH11-TC | 9 | 15 | 60.0 | 1.56 | | |
| DP0058.13 | 10 | 16 | 62.5 | 1.43 | 0.0020 | Y |
| ZH11-TC | 0 | 16 | 0.0 | 0.00 | | |
| DP0058.14 | 9 | 16 | 56.3 | 1.45 | 0.7110 | |
| ZH11-TC | 6 | 16 | 37.5 | 1.26 | | |
| DP0058.15 | 9 | 15 | 60.0 | 1.09 | 0.0131 | Y |
| ZH11-TC | 3 | 16 | 18.8 | 0.28 | | |

TABLE 10

Enhanced drought tolerance of OsPPCK4 transgenic rice plants under greenhouse conditions at construct level (2nd experiment)

| Construct ID | Number of survived plants | Number of total plants | Survival rate (%) | Average recovery degree | P value | P ≤ 0.05 |
|---|---|---|---|---|---|---|
| DP0058 | 49 | 108 | 45.4 | 0.66 | 0.0479 | Y |
| ZH11-TC | 6 | 24 | 25.0 | 0.32 | | |
| DP0058 | 49 | 108 | 45.4 | 0.66 | 0.0102 | Y |
| DP0158 | 1 | 12 | 8.3 | 0.08 | | |

TABLE 11

Enhanced drought tolerance of OsPPCK4 transgenic rice plants under greenhouse conditionsat transgenic line level (2nd experiment)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0058.01 | 8 | 12 | 66.7 | 0.77 | 0.0269 | Y | 0.0059 | Y |
| DP0058.03 | 3 | 12 | 25.0 | 0.51 | 0.3440 | | 0.0846 | |
| DP0058.04 | 7 | 12 | 58.3 | 0.73 | 0.0405 | Y | 0.0088 | Y |
| DP0058.05 | 5 | 12 | 41.7 | 0.69 | 0.0665 | | 0.0144 | Y |
| DP0058.06 | 6 | 12 | 50.0 | 0.63 | 0.1200 | | 0.0265 | Y |
| DP0058.10 | 3 | 12 | 25.0 | 0.53 | 0.3037 | | 0.0732 | |
| DP0058.13 | 8 | 12 | 66.7 | 0.77 | 0.0247 | Y | 0.0054 | Y |
| DP0058.15 | 3 | 12 | 25.0 | 0.54 | 0.2668 | | 0.0631 | |
| DP0058.16 | 6 | 12 | 50.0 | 0.73 | 0.0438 | Y | 0.0095 | Y |
| ZH11-TC | 6 | 24 | 25.0 | 0.32 | | | 0.3444 | |
| DP0158 | 1 | 12 | 8.3 | 0.08 | | | | |

TABLE 9-continued

Enhanced drought tolerance of OsPPCK4transgenic rice plants under greenhouse conditions (1st experiment)

| Line ID | Number of survived plants | Number of total plants | Survival rate (%) | Average recovery degree | Pvalue | P ≤ 0.05 |
|---|---|---|---|---|---|---|
| DP0058.18 | 12 | 16 | 75.0 | 2.33 | 0.0045 | Y |
| ZH11-TC | 5 | 16 | 31.3 | 0.96 | | |

In the second experiment, construct level design was used, and nine transgenic lines were tested. When grown to 3-leaf stage, the plants were drought stressed for 17 days, recovered in water for seven days. 49 of the 108 OsPPCK4 transgenic rice plants survived, whereas 6 of the 24 ZH11-TC and 1 of the 12 DP0158 seedlings survived. OsPPCK4 transgenic rice exhibited higher survival rate and exhibited significantly higher average recovery degree than both ZH11-TC and DP0158 seedlings at the construct level (Table 10). Analysis at line level showed that six lines exhibited higher survival rates and nine lines exhibited higher recovery degrees than both controls (Table 11). These results demonstrate that OsPPCK4 transgenic rice showed enhanced drought tolerance at seedling stage and OsPPCK4 plays a role in improving drought tolerance of transgenic plants.

3) GH DRT Validation Results of OsCAM2 (DP0059) Transgenic Rice

In the first experiment, Latin square design was used, and eight OsCAM2 transgenic lines were tested. Different lines were planted in different trays, and the ZH11-TC seedlings in the same tray were used as their corresponding controls. Table 12 shows that six lines had higher survival rates and recovery degrees than that of ZH11-TC control, and four of which showed significantly higher recovery degrees, indicating that the OsCAM2 transgenic rice plants had improved drought tolerance at seedling stage.

In the second experiment, construct level testing design was used, and the eight OsCAM2 transgenic lines were tested again. As shown in Table 13, 83 of the 96 OsCAM2 transgenic seedlings survived after drought stress, and the survival rate and recovery degree was higher than that of DP0158 control (P value=0.0679) and significantly higher than that of ZH11-TC control (P value=0.0090). Analysis at transgenic line level showed that all the eight lines exhibited higher survival rates and average recovery degrees, five lines showed significantly higher recovery degrees than ZH11-TC control and three lines showed significantly higher recovery degrees than DP0158 control (Table 14). These results further demonstrate that OsCAM2 gene enhances drought tolerance in plant.

In the third experiment, construct level design was also used, and eight transgenic lines were tested. When grown to 3-leaf stage, the plants were drought stressed for 15 days, recovered in water for seven days. 55 of the 96 OsCAM2 transgenic rice plants survived, while 4 of the 24 ZH11-TC and 4 of the 12 DP0158 seedlings survived. OsCAM2 transgenic rice exhibited higher survival rate and exhibited significantly higher average recovery degree than both ZH11-TC seedlings at the construct level (Table 15). Analysis at line level showed that all the eight lines exhibited higher survival rates and average recovery degrees than both controls (Table 16). In these three experiments, OsCAM2 transgenic rice showed enhanced drought tolerance at seedling stage. These results demonstrate that OsCAM2 plays a role in improving drought tolerance of transgenic plants.

TABLE 12

Enhanced drought tolerance of OsCAM2 transgenic rice plants under greenhouse conditions (1st experiment)

| Line ID | Number of survived plants | Number of total plants | Survival rate (%) | Average recovery degree | Pvalue | P ≤ 0.05 |
|---|---|---|---|---|---|---|
| DP0059.01 | 8 | 16 | 50.0 | 0.58 | 0.0100 | Y |
| ZH11-TC | 0 | 15 | 0.0 | 0.00 | | |
| DP0059.04 | 10 | 16 | 62.5 | 1.03 | 0.5592 | |
| ZH11-TC | 6 | 15 | 40.0 | 0.89 | | |
| DP0059.05 | 11 | 16 | 68.8 | 0.93 | 0.1365 | |
| ZH11-TC | 4 | 16 | 25.0 | 0.50 | | |
| DP0059.09 | 11 | 16 | 68.8 | 1.23 | 0.0239 | Y |
| ZH11-TC | 9 | 16 | 56.3 | 0.60 | | |
| DP0059.11 | 14 | 16 | 87.5 | 1.28 | 0.0252 | Y |
| ZH11-TC | 9 | 15 | 60.0 | 0.76 | | |
| DP0059.12 | 3 | 16 | 18.8 | 0.76 | 0.4943 | |
| ZH11-TC | 5 | 16 | 31.3 | 1.17 | | |
| DP0059.13 | 4 | 16 | 25.0 | 0.28 | 0.2387 | |
| ZH11-TC | 9 | 16 | 56.3 | 0.60 | | |
| DP0059.14 | 14 | 15 | 93.3 | 1.64 | 0.0003 | Y |
| ZH11-TC | 9 | 15 | 60.0 | 0.76 | | |

TABLE 13

Enhanced drought tolerance of OsCAM2 transgenic rice plants under greenhouse conditions at construct level (2nd experiment)

| Construct ID | Number of survived plants | Number of total plants | Survival rate (%) | Average recovery degree | Pvalue | P ≤ 0.05 |
|---|---|---|---|---|---|---|
| DP0059 | 83 | 96 | 86.5 | 1.05 | 0.0090 | Y |
| ZH11-TC | 15 | 23 | 65.2 | 0.68 | | |
| DP0059 | 83 | 96 | 86.5 | 1.05 | 0.0679 | |
| DP0158 | 7 | 12 | 58.3 | 0.71 | | |

TABLE 14

Enhanced drought tolerance of OsCAM2 transgenic rice plants under greenhouse conditions at line level (2nd experiment)

| Line ID | Number of survived plants | Number of total plants | Survival rate (%) | Average recovery decree | CK = ZH11-TC P value | P ≤ 0.05 | CK = DP0158 P value | P ≤ 0.05 |
|---|---|---|---|---|---|---|---|---|
| DP0059.01 | 11 | 12 | 91.7 | 1.00 | 0.0535 | | 0.1576 | |
| DP0059.04 | 9 | 12 | 75.0 | 0.94 | 0.1143 | | 0.2599 | |
| DP0059.05 | 12 | 12 | 100.0 | 1.13 | 0.0066 | Y | 0.0399 | Y |
| DP0059.09 | 12 | 12 | 100.0 | 1.18 | 0.0030 | Y | 0.0240 | Y |
| DP0059.11 | 10 | 12 | 83.3 | 1.02 | 0.0419 | Y | 0.1341 | |
| DP0059.12 | 8 | 12 | 66.7 | 0.92 | 0.1401 | | 0.2975 | |
| DP0059.13 | 10 | 12 | 83.3 | 1.07 | 0.0190 | Y | 0.0800 | |
| DP0059.14 | 11 | 12 | 91.7 | 1.13 | 0.0070 | Y | 0.0415 | Y |
| ZH11-TC | 15 | 23 | 65.2 | 0.68 | | | | |
| DP0158 | 7 | 12 | 58.3 | 0.71 | | | | |

TABLE 15

Enhanced drought tolerance of OsCAM2 transgenic rice plants under greenhouse conditions at the construct level (3rd experiment)

| Construct ID | Number of survived plants | Number of total plants | Survival rate (%) | Average recovery degree | P value | P ≤ 0.05 |
|---|---|---|---|---|---|---|
| DP0059 | 55 | 96 | 57.3 | 0.59 | 0.0004 | Y |
| ZH11-TC | 4 | 24 | 16.7 | 0.17 | | |
| DP0059 | 55 | 96 | 57.3 | 0.59 | 0.1012 | |
| DP0158 | 4 | 12 | 33.3 | 0.33 | | |

TABLE 16

Enhanced drought tolerance of OsCAM2transgenic rice plants under greenhouse conditions at line level (3rd experiment)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0059.01 | 10 | 12 | 83.3 | 0.67 | 0.0002 | Y | 0.0497 | Y |
| DP0059.04 | 7 | 12 | 58.3 | 0.59 | 0.0020 | Y | 0.1346 | |
| DP0059.05 | 8 | 12 | 66.7 | 0.61 | 0.0010 | Y | 0.0985 | |
| DP0059.09 | 6 | 12 | 50.0 | 0.56 | 0.0038 | Y | 0.1801 | |
| DP0059.11 | 9 | 12 | 75.0 | 0.65 | 0.0003 | Y | 0.0594 | |
| DP0059.12 | 5 | 12 | 41.7 | 0.53 | 0.0069 | Y | 0.2359 | |
| DP0059.13 | 4 | 12 | 33.3 | 0.51 | 0.0121 | Y | 0.3032 | |
| DP0059.14 | 6 | 12 | 50.0 | 0.59 | 0.0020 | Y | 0.1346 | |
| ZH11-TC | 4 | 24 | 16.7 | 0.17 | | | | |
| DP0158 | 4 | 12 | 33.3 | 0.33 | | | | |

4) GH DRT Validation Results of OsDN-DTP4 (DP0167) Transgenic Rice

In the first experiment, Latin square design was used, and 12 OsDN-DTP4 transgenic lines were tested. Different lines were planted in different trays, and the ZH11-TC seedlings in the same tray were used as their corresponding controls. Table 17 shows that eight lines had higher survival rates and recovery degrees, and four lines had significantly higher recovery degrees than that of ZH11-TC control. These results indicate that the OsDN-DTP4 transgenic rice plants had improved drought tolerance at seedling stage.

Nine lines were tested in the second and third experiments using construct level design. In the second experiment, as shown in Table 18, all the tested OsDN-DTP4 transgenic rice plants exhibited higher survival rate and recovery degree than that of DP0158 and ZH11-TC controls at the construct level. And further analysis at line level indicated that all of the 9 lines showed higher survival rates and recovery degrees than that of either ZH11-TC or DP0158 control (Table 19). And the experimental results in the third experiment, showed the same tendency (Table 20 and 21). The recovery degree of all the tested OsDN-DTP4 transgenic rice plants had higher survival rate and recovery degree than that of ZH11-TC and DP0158 controls both at construct level and at transgenic line level. All these results further demonstrate that OsDN-DTP4 gene enhances drought tolerance in plant.

TABLE 17

Drought tolerance assay of OsDN-DTP4 transgenic rice plants under greenhouse conditions (1st experiment)

| Line ID | Number of survived plants | Number of total plants | Survival rate (%) | Average recovery degree | Pvalue | P ≤ 0.05 |
|---|---|---|---|---|---|---|
| DP0167.01 | 11 | 16 | 68.8 | 0.93 | 0.8279 | |
| ZH11-TC | 10 | 16 | 62.5 | 0.89 | | |
| DP0167.02 | 9 | 16 | 56.3 | 0.81 | 0.0208 | Y |
| ZH11-TC | 2 | 16 | 12.5 | 0.13 | | |
| DP0167.03 | 9 | 16 | 56.3 | 1.12 | 0.0227 | Y |
| ZH11-TC | 2 | 16 | 12.5 | 0.25 | | |
| DP0167.04 | 3 | 16 | 18.8 | 0.34 | 0.5673 | |
| ZH11-TC | 2 | 16 | 12.5 | 0.19 | | |
| DP0167.05 | 8 | 16 | 50.0 | 0.73 | 0.0186 | Y |
| ZH11-TC | 1 | 15 | 6.7 | 0.13 | | |
| DP0167.06 | 9 | 16 | 56.3 | 1.03 | 0.1491 | |
| ZH11-TC | 4 | 15 | 26.7 | 0.56 | | |
| DP0167.07 | 6 | 16 | 37.5 | 0.45 | 0.7690 | |
| ZH11-TC | 6 | 15 | 40.0 | 0.38 | | |
| DP0167.08 | 13 | 16 | 81.3 | 1.64 | 0.1871 | |
| ZH11-TC | 12 | 16 | 75.0 | 1.22 | | |
| DP0167.09 | 11 | 16 | 68.8 | 0.69 | 0.0038 | Y |
| ZH11-TC | 4 | 16 | 25.0 | 0.25 | | |
| DP0167.11 | 8 | 16 | 50.0 | 0.61 | 0.8116 | |
| ZH11-TC | 6 | 16 | 37.5 | 0.67 | | |
| DP0167.13 | 8 | 16 | 50.0 | 0.51 | 0.7480 | |
| ZH11-TC | 9 | 16 | 56.3 | 0.56 | | |

TABLE 18

Drought tolerance assay of OsDN-DTP4 transgenic rice plants under greenhouse conditions at construct level (2nd experiment)

| Construct ID | Number of survived plants | Number of total plants | Survival rate (%) | Average recovery degree | Pvalue | P ≤ 0.05 |
|---|---|---|---|---|---|---|
| DP0167 | 84 | 108 | 77.8 | 0.97 | 0.1807 | |
| ZH11-TC | 16 | 24 | 66.7 | 0.75 | | |

TABLE 18-continued

Drought tolerance assay of OsDN-DTP4 transgenic rice plants under greenhouse conditions at construct level (2$^{nd}$ experiment)

| Construct ID | Number of survived plants | Number of total plants | Survival rate (%) | Average recovery degree | Pvalue | P ≤ 0.05 |
|---|---|---|---|---|---|---|
| DP0167 | 84 | 108 | 77.8 | 0.97 | 0.0823 | |
| DP0158 | 5 | 12 | 41.7 | 0.58 | | |

TABLE 19

Drought tolerance assay of OsDN-DTP4 transgenic rice plants under greenhouse conditions at line level (2$^{nd}$ experiment)

| Line ID | Number of survived plants | Number of total plants | Survival rate (%) | Average recovery degree | CK = ZH11-TC | | CK = DP0158 | |
|---|---|---|---|---|---|---|---|---|
| | | | | | P value | P ≤ 0.05 | P value | P ≤ 0.05 |
| DP0167.01 | 11 | 12 | 91.7 | 0.97 | 0.1807 | | 0.0823 | |
| DP0167.02 | 8 | 12 | 66.7 | 0.97 | 0.1807 | | 0.0823 | |
| DP0167.03 | 11 | 12 | 91.7 | 0.97 | 0.1807 | | 0.0823 | |
| DP0167.04 | 8 | 12 | 66.7 | 0.97 | 0.1807 | | 0.0823 | |
| DP0167.05 | 9 | 12 | 75.0 | 0.97 | 0.1807 | | 0.0823 | |
| DP0167.06 | 10 | 12 | 83.3 | 0.97 | 0.1807 | | 0.0823 | |
| DP0167.07 | 9 | 12 | 75.0 | 0.97 | 0.1807 | | 0.0823 | |
| DP0167.11 | 9 | 12 | 75.0 | 0.97 | 0.1807 | | 0.0823 | |
| DP0167.12 | 9 | 12 | 75.0 | 0.97 | 0.1807 | | 0.0823 | |
| ZH11-TC | 16 | 24 | 66.7 | 0.75 | | | | |
| DP0158 | 5 | 12 | 41.7 | 0.58 | | | | |

TABLE 20

Drought tolerance assay of OsDN-DTP4 transgenic rice plants under greenhouse conditions at construct level (3$^{rd}$ experiment)

| Construct ID | Number of survived plants | Number of total plants | Survival rate (%) | Average recovery degree | P value | P ≤ 0.1 |
|---|---|---|---|---|---|---|
| DP0167 | 55 | 108 | 50.9 | 0.69 | 0.6312 | |
| ZH11-TC | 11 | 24 | 45.8 | 0.61 | | |
| DP0167 | 55 | 108 | 50.9 | 0.69 | 0.0561 | Y |
| DP0158 | 3 | 12 | 25.0 | 0.27 | | |

TABLE 21

Drought tolerance assay of OsDN-DTP4 transgenic rice plants under greenhouse conditions at line level (3$^{rd}$ experiment)

| Line ID | Number of survived plants | Number of total plants | Survival rate (%) | Average recovery degree | CK = ZH11-TC | | CK = DP0158 | |
|---|---|---|---|---|---|---|---|---|
| | | | | | P value | P ≤ 0.05 | P value | P ≤ 0.05 |
| DP0167.01 | 7 | 12 | 58.3 | 0.69 | 0.6312 | | 0.0561 | |
| DP0167.02 | 6 | 12 | 50.0 | 0.69 | 0.6312 | | 0.0561 | |
| DP0167.03 | 6 | 12 | 50.0 | 0.69 | 0.6312 | | 0.0561 | |
| DP0167.04 | 8 | 12 | 66.7 | 0.69 | 0.6312 | | 0.0561 | |
| DP0167.05 | 6 | 12 | 50.0 | 0.69 | 0.6312 | | 0.0561 | |
| DP0167.06 | 4 | 12 | 33.3 | 0.69 | 0.6312 | | 0.0561 | |
| DP0167.07 | 5 | 12 | 41.7 | 0.69 | 0.6312 | | 0.0561 | |
| DP0167.11 | 6 | 12 | 50.0 | 0.69 | 0.6312 | | 0.0561 | |
| DP0167.12 | 7 | 12 | 58.3 | 0.69 | 0.6312 | | 0.0561 | |
| ZH11-TC | 11 | 24 | 45.8 | 0.61 | | | | |
| DP0158 | 3 | 12 | 25.0 | 0.27 | | | | |

Example 5

Field Drought Tolerance Assays of Mature Transgenic Rice Plants

Drought stress at flowering stage is an important problem in agriculture practice. The transgenic rice plants were further tested under field drought conditions. For the field drought assays of mature rice plants, 9-12 transgenic lines of each construct were tested. The T$_2$ seeds were first sterilized as described in Example 4. The germinated seeds were planted into a seedbed. The seedlings were transplanted into the testing field at 3-leaf stage with 3-4 replicates. About 8-10 plants per replicate for each transgenic line were planted into the same block. And the ZH11-TC, DP0158, Bulk Null or Line Null planted nearby the transgenic lines of the same block, were used as the controls in statistical analysis according to the experimental design.

The rice plants were managed by normal practice using pesticides and fertilizers. Watering was stopped at the panicle initiation stage II stage, so as to give drought stress at flowering stage depending on the weather conditions (temperature and humidity). The soil water content was measured every four days at several sites of each block using TDR30 (Spectrum Technologies, Inc.).

Plant phenotypes, included heading date, leaf rolling degree, drought sensitivity and drought tolerance, were observed and recorded during the experimental processes. Special attention was paid to the leaf rolling degree at noontime. At the end of the planting season, six representative plants of each transgenic line were harvested from the middle of the row per line, and the grain weight per plant was measured. The grain weight data were statistically analyzed using mixed linear model. Positive transgenic lines were selected based on the analysis.

Field Drought Assay Results:

1) Field DRT Validation Results of OsGSTU41 (DP0043) Transgenic Rice

Figure 1:
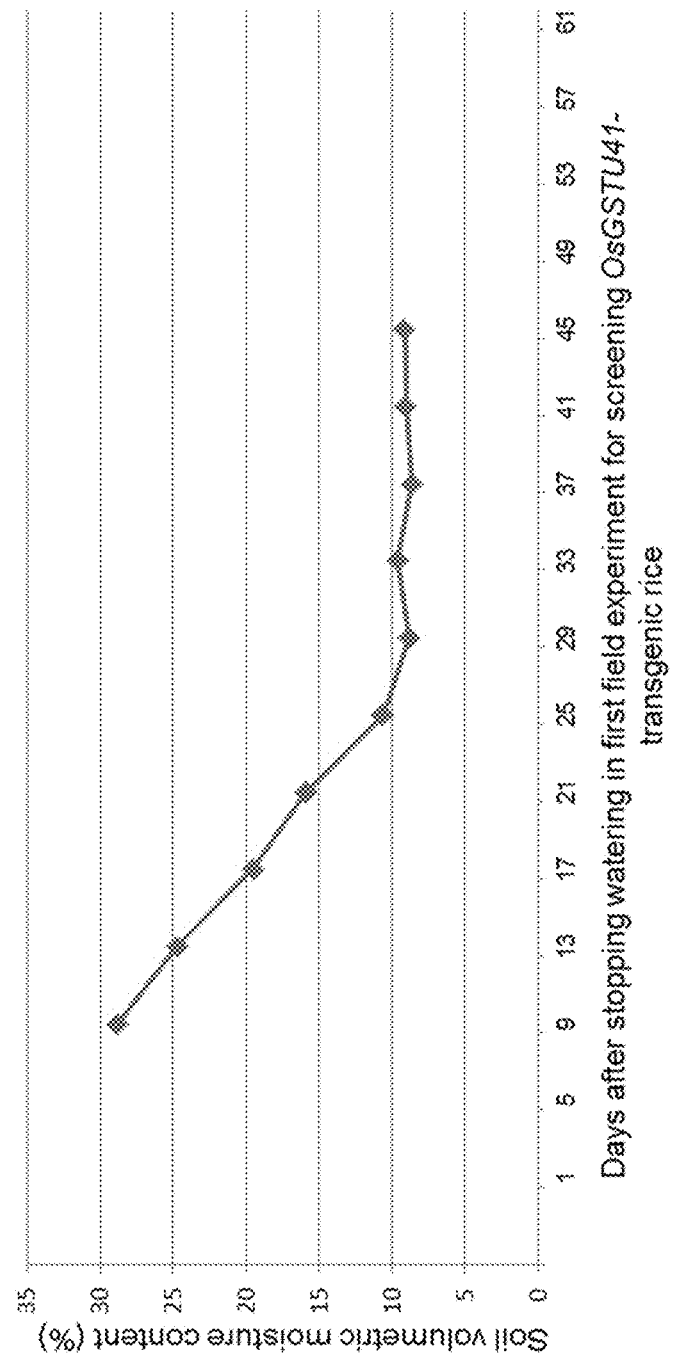
FIG. 1 shows changes of soil volumetric moisture content at different developmental stages in the first field experiment for drought screening OsGSTU41 transgenic rice. The OsGSTU41 transgenic rice started heading at 26 days after stopping watering and matured at 63 days after stopping watering.

Twenty-two OsGSTU41 transgenic lines were tested in Hainan Province in the first field experiment using the corresponding line null planted every two rows as the control. Four replicates per transgenic line and 10 plants per replicate were planted into the same block. Watering was stopped from panicle initiation stage II to seed mature to produce heavier drought stress. The soil volumetric moisture content decreased from about 30% to 10% during the heading and maturation stages (FIG. 1). At the end of the planting season, six representative plants of each transgenic line were harvested from the middle of the row per line, and the grain weight per plant was measured. Thirteen lines exhibited higher grain yield per plant than that of their corresponding line null control, and seven lines exhibited significantly higher at the level of $P<0.05$ as shown in Table 22. These results demonstrate that OsGSTU41 transgenic rice plants had greater grain yield per plant than that of the control after drought stress.

Figure 2:
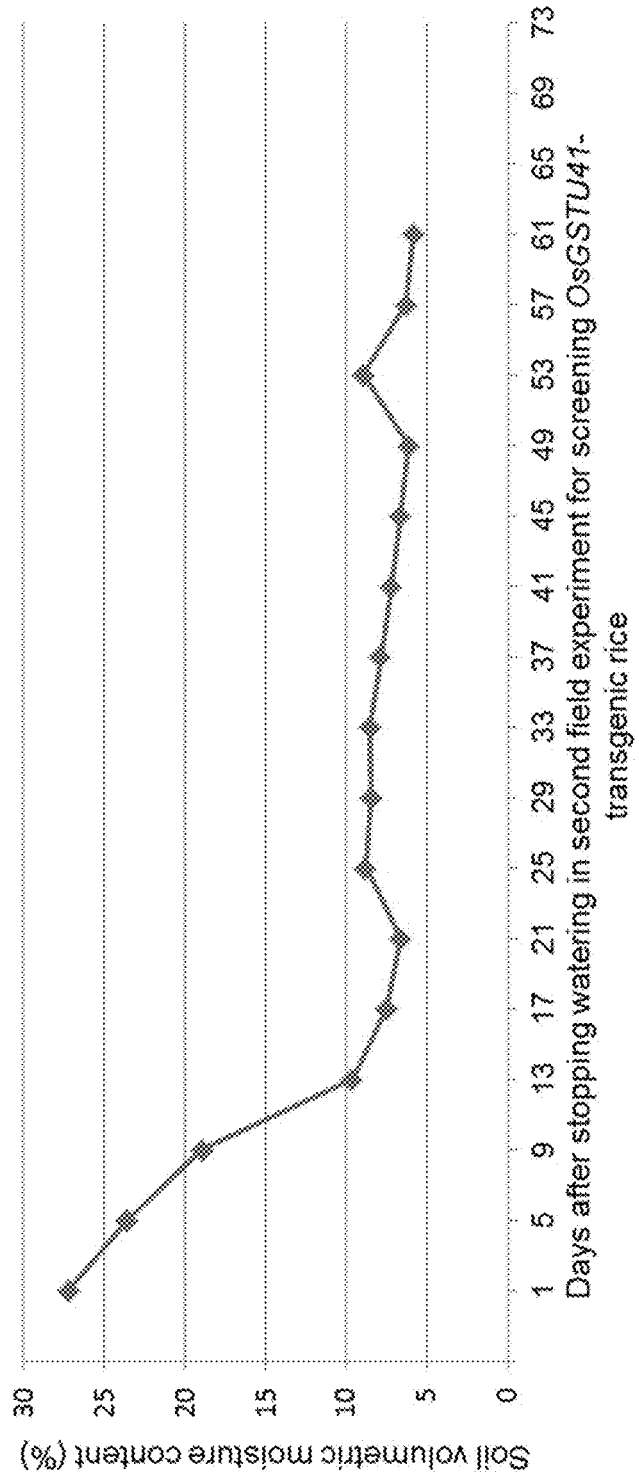
FIG. 2 shows changes of soil volumetric moisture content at different developmental stages in the second field experiment for drought screening OsGSTU41 transgenic rice. The OsGSTU41 transgenic rice started heading at 43 days after stopping watering and matured at 73 days after stopping watering.

Twelve OsGSTU41 transgenic lines were tested again in Hainan Province in the second field experiment. The bulk null planted nearby were used as the control. And three replicates per transgenic line and eight plants per replicate were planted into the same block. Watering was stopped from panicle initiation stage II to seed mature to produce heavier drought stress. The soil volumetric moisture content decreased from about 27% to 6% during the heading and maturation stages (FIG. 2). Three transgenic lines DP0043.10, DP0043.16 and DP0043.22 showed drought tolerance phenotype such as less leaf roll degree and greener leaf. Four lines DP0043.10, DP0043.16, DP0043.22 and DP0043.26 showed better seed setting rates at the maturation stage. At the end of the planting season, six representative plants of each transgenic line were harvested from the middle of the row per line, and the grain weight per plant was measured. As shown in Table 23, 11 OsGSTU41 transgenic lines exhibited higher grain yield per plant than that of the bulk null control, and two lines showed significantly higher at the level of $P<0.1$. These results further demonstrate that OsGSTU41 transgenic rice plants had greater grain yield per plant than that of the control after drought stress.

As described in Example 4, OsGSTU41 transgenic rice exhibited enhanced drought tolerance at seedling stage. These results at mature stage further demonstrate OsGSTU41 gene plays a role in enhancing drought tolerance in plant from seedling stage to mature stage.

TABLE 22

Grain yield analysis of OsGSTU41 transgenic rice plants under field drought conditions (1st experiment)

| Line ID | Number of survived plants | Number of harvest plants | Grain yield per plant (g) | Pvalue | P ≤ 0.05 |
|---|---|---|---|---|---|
| DP0043.06 | 40 | 24 | 4.93 | 0.993 | |
| DP0043.06-Null | 40 | 24 | 4.59 | | |
| DP0043.10 | 40 | 24 | 4.36 | 0.008 | Y |
| DP0043.11-Null | 40 | 24 | 2.42 | | |
| DP0043.11 | 40 | 24 | 2.75 | 0.491 | |
| DP0043.11-Null | 40 | 24 | 2.42 | | |
| DP0043.12 | 40 | 24 | 3.49 | 0.455 | |
| DP0043.12-Null | 40 | 24 | 3.00 | | |
| DP0043.13 | 40 | 24 | 5.63 | 0.022 | Y |
| DP0043.13-Null | 40 | 24 | 2.91 | | |
| DP0043.16 | 40 | 24 | 3.57 | 0.000 | Y |
| DP0043.16-Null | 40 | 24 | 0.11 | | |
| DP0043.17 | 40 | 24 | 6.88 | 0.000 | Y |
| DP0043.17-Null | 40 | 24 | 1.99 | | |
| DP0043.21 | 40 | 24 | 5.32 | 0.013 | Y |
| DP0043.21-Null | 40 | 24 | 2.94 | | |
| DP0043.22 | 40 | 24 | 4.02 | 0.048 | Y |
| DP0043.22-Null | 40 | 24 | 1.92 | | |
| DP0043.23 | 40 | 24 | 6.65 | 0.457 | |
| DP0043.23-Null | 40 | 24 | 5.98 | | |
| DP0043.24 | 40 | 24 | 3.89 | 0.884 | |
| DP0043.24-Null | 40 | 24 | 3.61 | | |
| DP0043.26 | 40 | 24 | 7.77 | 0.026 | Y |
| DP0043.26-Null | 40 | 24 | 6.01 | | |
| DP0043.29 | 40 | 24 | 4.33 | 0.098 | |
| DP0043.29-Null | 40 | 24 | 2.56 | | |

TABLE 23

Grain yield analysis of OsGSTU41 transgenic rice plants under field drought conditions (2nd experiment)

| Line ID | Number of survived plants | Number of harvest plants | Grain yield per plant (g) | Pvalue | CK = Bulk Null P ≤ 0.1 |
|---|---|---|---|---|---|
| DP0043.02 | 24 | 15 | 5.19 | 0.464 | |
| DP0043.03 | 24 | 16 | 4.69 | 0.766 | |
| DP0043.04 | 24 | 14 | 4.73 | 0.747 | |
| DP0043.06 | 24 | 15 | 4.86 | 0.647 | |
| DP0043.10 | 24 | 15 | 4.74 | 0.731 | |
| DP0043.13 | 24 | 16 | 4.97 | 0.588 | |
| DP0043.16 | 24 | 16 | 6.43 | 0.061 | Y |
| DP0043.17 | 24 | 15 | 4.87 | 0.658 | |
| DP0043.21 | 24 | 16 | 4.82 | 0.673 | |
| DP0043.22 | 24 | 16 | 4.78 | 0.720 | |
| DP0043.26 | 24 | 15 | 6.77 | 0.031 | Y |
| DP0043.29 | 24 | 16 | 4.36 | 0.988 | |
| CK (Bulk Null) | 24 | 16 | 4.38 | | |

2) Field DRT Validation Results of OsPPCK4 (DP0058) Transgenic Rice

Nine OsPPCK4 transgenic lines were tested in Beijing in the first field experiment using ZH11-TC and DP0158 rice plants as the controls. Three replicates per transgenic line and eight plants per replicate were planted into the same block. Watering was stopped from panicle initiation stage II to seed mature to produce heavier drought stress. The soil volumetric water content decreased from about 50% to 10% during the heading and maturation stages (FIG. 8). The transgenic line DP0058.14 showed drought tolerance phenotype such as keeping leaf expanding and leaf green. At the end of the planting season, about six representative plants of each transgenic line were harvested from the middle of the row per line, and the grain weight per plant was measured. Nine lines exhibited higher grain yield per plant than DP0158 control, and four lines exhibited higher grain yield per plant than ZH11-TC plants as shown in Table 24. These results demonstrate that OsPPCK4 transgenic rice plants had greater grain yield per plant than that of the control after drought stress.

TABLE 24

Grain yield analysis of OsPPCK4 transgenic rice plants under field drought conditions

| Line ID | Number of survived plants | Number of harvested plants | Grain yield per plant (g) | CK = ZH11-TC P value | P ≤ 0.1 | CK = DP0158 P value | P ≤ 0.1 |
|---|---|---|---|---|---|---|---|
| DP0058.02 | 24 | 14 | 6.90 | 0.044 | | 0.945 | |
| DP0058.07 | 24 | 16 | 7.88 | 0.220 | | 0.407 | |
| DP0058.08 | 24 | 18 | 9.58 | 0.928 | | 0.029 | Y |
| DP0058.10 | 24 | 17 | 9.94 | 0.709 | | 0.014 | Y |
| DP0058.12 | 24 | 17 | 9.56 | 0.943 | | 0.032 | Y |
| DP0058.13 | 24 | 17 | 9.14 | 0.807 | | 0.079 | Y |
| DP0058.14 | 23 | 16 | 10.04 | 0.663 | | 0.013 | Y |
| DP0058.15 | 24 | 17 | 7.08 | 0.069 | | 0.839 | |
| DP0058.18 | 24 | 17 | 7.82 | 0.211 | | 0.442 | |
| ZH11-TC | 24 | 18 | 9.47 | | | | |
| DP0158 | 24 | 17 | 6.81 | | | | |
| DP0043 (construct) | | | 8.66 | 0.45 | | 0.08 | Y |

3) Field DRT Validation Results of OsCAM2 (DP0059) Transgenic Rice

Eight OsCAM2 transgenic lines were tested in Beijing in the first field experiment using ZH11-TC and DP0158 rice plants as the controls. Three replicates per transgenic line and eight plants per replicate were planted into the same block. Watering was stopped from panicle initiation stage II to seed mature to produce heavier drought stress. The soil volumetric moisture content decreased from about 50% to 10% during the heading and maturation stages (FIG. 9). DP0059.05 showed better drought tolerance phenotype and better seed setting rate than control during drought stress. At the end of the planting season, about six representative plants of each transgenic line were harvested from the middle of the row per line, and the grain weight per plant was measured. The OsCAM2 transgenic rice exhibited significantly greater grain yield per plant than DP0158 control at the construct level. Eight lines exhibited higher grain yield per plant than DP0158 control, and three lines exhibited higher grain yield per plant than ZH11-TC plants as shown in Table 25. These results demonstrate that OsCAM2 transgenic rice plants had greater grain yield per plant than that of the control after drought stress.

The second experiment was performed in Hainan province; the same eight OsCAM2 transgenic lines were tested. ZH11-TC and DP0158 rice plants were used as control. Ten plants from each line were planted and repeated for four times. Watering was stopped from panicle initiation stage II to seed maturity to produce heavier drought stress. The soil volumetric water content decreased from 35% to 5% during heading and maturation stage (FIG. 10). Five lines DP0059.04, DP0059.05, DP0059.09, DP0059.11 and DP0059.14 showed drought tolerance phenotype, the leaf rolling degree was less than control and the leaves were greener. At the end of the growing season, OsCAM2 transgenic rice did not show greater grain yield per plant, only two lines showed greater grain yields per plant (Table 26). These results demonstrate that OsCAM2 over-expressed transgenic rice plant obtained drought tolerance at seedling stage and over-expression of OsCAM2 improved the drought tolerance.

TABLE 25

Grain yield analysis of OsCAM2 transgenic rice plants under field drought conditions(1st experiment)

| Line ID | Number of survived plants | Number of harvest plants | Grain yield per plant (g) | CK = ZH11-TC P value | P ≤ 0.1 | CK = DP0158 P value | P ≤ 0.1 |
|---|---|---|---|---|---|---|---|
| DP0059.01 | 24 | 17 | 9.42 | 0.969 | | 0.048 | Y |
| DP0059.04. | 24 | 17 | 8.77 | 0.592 | | 0.135 | |
| DP0059.05 | 24 | 18 | 10.09 | 0.624 | | 0.011 | Y |
| DP0059.09 | 24 | 17 | 9.16 | 0.811 | | 0.066 | Y |
| DP0059.11 | 24 | 18 | 10.12 | 0.617 | | 0.011 | Y |
| DP0059.12 | 24 | 18 | 8.81 | 0.611 | | 0.123 | |
| DP0059.13 | 24 | 15 | 8.82 | 0.622 | | 0.125 | |
| DP0059.14 | 24 | 12 | 10.57 | 0.404 | | 0.005 | Y |
| ZH11-TC | 24 | 17 | 9.47 | | | | |
| DP0158 | 24 | 16 | 6.81 | | | | |
| DP0059 (construct) | | | 9.47 | 1.00 | | 0.015 | Y |

TABLE 26

Grain yield analysis of OsCAM2 transgenic rice plants under field drought conditions(2$^{nd}$ experiment)

| Line ID | Number of survival plants | Number of harvested plants | Yield per plant (g) | CK = ZH11-TC P value | P ≤ 0.1 | CK = DP0158 P value | P ≤ 0.1 |
|---|---|---|---|---|---|---|---|
| DP0059.01 | 40 | 24 | 4.48 | 0.017 | | 0.024 | |
| DP0059.04 | 40 | 24 | 5.68 | 0.449 | | 0.565 | |
| DP0059.05 | 40 | 24 | 5.06 | 0.109 | | 0.168 | |
| DP0059.09 | 40 | 24 | 6.27 | 0.994 | | 0.862 | |
| DP0059.11 | 40 | 24 | 5.55 | 0.367 | | 0.471 | |
| DP0059.12 | 39 | 24 | 5.25 | 0.177 | | 0.259 | |
| DP0059.13 | 40 | 24 | 4.99 | 0.089 | | 0.127 | |
| DP0059.14 | 39 | 24 | 6.79 | 0.514 | | 0.400 | |
| ZH11-TC | 40 | 24 | 6.27 | | | | |
| DP0158 | 39 | 24 | 6.13 | | | | |
| DP0059 (construct) | | | 5.51 | 0.313 | | 0.413 | |

4) Field DRT Validation Results of OsLecRK4.1 (DP0173) Transgenic Rice

Twelve OsLecRK4.1 transgenic lines were tested in the first field experiment using ZH11-TC and DP0158 rice plants as the controls. Four replicates per transgenic line and ten plants per replicate were planted into the same block. Watering was stopped from panicle initiation stage II to seed mature to produce heavier drought stress. The soil volumetric moisture content decreased from about 40% to 5% during the heading and maturation stages (FIG. 11). Four transgenic lines DP0173.01, DP0173.04, DP0173.08 and DP0173.14 showed greener leaf and less leaf roll degree compared with the ZH11-TC and DP0158 controls planted nearby. DP0173.04 also showed better seed setting rate at the maturation stage. The grain weight per plant of OsLecRK4.1 transgenic rice was less than ZH11-TC but more than DP0158 control at the construct level. Transgenic line level analysis is shown in Table 27. These results demonstrate that OsLecRK4.1 transgenic rice plants had improved drought tolerance at seedling stage and may improve the grain yield per plant after drought stress.

TABLE 27

Grain yield analysis of OsLecRK4.1 transgenic rice plants under field drought conditions

| Line ID | Number of survival plants | Number of harvested plants | Yield per plant (g) | CK = ZH11-TC P value | P ≤ 0.1 | CK= DP0158 P value | P ≤ 0.1 |
|---|---|---|---|---|---|---|---|
| DP0173.01 | 40 | 24 | 3.47 | 0.128 | | 0.052 | Y |
| DP0173.04 | 40 | 24 | 4.49 | 0.792 | | 0.001 | Y |
| DP0173.06 | 40 | 24 | 2.21 | 0.001 | | 0.867 | |
| DP0173.08 | 39 | 23 | 4.69 | 0.948 | | 0.001 | Y |
| DP0173.11 | 40 | 24 | 3.42 | 0.045 | | 0.133 | |
| DP0173.12 | 40 | 24 | 3.30 | 0.063 | | 0.105 | |
| DP0173.13 | 39 | 23 | 2.15 | 0.001 | | 0.910 | |
| DP0173.14 | 32 | 20 | 2.39 | 0.001 | | 0.904 | |
| DP0173.15 | 39 | 21 | 4.17 | 0.360 | | 0.010 | Y |
| DP0173.17 | 40 | 24 | 2.91 | 0.008 | | 0.393 | |
| DP0173.18 | 38 | 24 | 3.34 | 0.045 | | 0.119 | |
| DP0173.25 | 40 | 24 | 3.32 | 0.072 | | 0.076 | Y |
| ZH11-TC | 40 | 24 | 4.51 | | | | |
| DP0158 | 40 | 24 | 2.36 | | | | |
| DP0173 (construct) | | | 3.21 | 0.031 | | 0.080 | Y |

5) Field DRT Validation Results of OsLecRK4.2 (DP0209) Transgenic Rice

Twelve OsLecRK4.2 transgenic lines were tested in the first field experiment using ZH11-TC and DP0158 rice plants as the controls. Four replicates per transgenic line and ten plants per replicate were planted into the same block. Watering was stopped from panicle initiation stage II to seed mature to produce heavier drought stress. The soil volumetric moisture content decreased from about 35% to 5% during the heading and maturation stages (FIG. 12). Four transgenic lines DP0209.13, DP0209.26, DP0209.28 and DP0209.34 showed greener leaf and less leaf roll degree compared with the ZH11-TC and DP0158 controls planted nearby. DP0209.34 showed better seed setting rate at the maturation stage. The grain weight per plant of OsLecRK4.2 transgenic rice was less than ZH11-TC and DP0158 control at the construct level. Transgenic line level analysis is shown in Table 28. These results demonstrate that OsLecRK4.2 transgenic rice plants had improved drought tolerance at seedling stage after drought stress.

TABLE 28

Grain yield analysis of OsLecRK4.2 transgenic rice plants under field drought conditions

| Line ID | Number of survival plants | Number of harvested plants | Grain yield per plant (g) | CK = ZH11-TC P value | P ≤ 0.1 | CK = DP0158 P value | P ≤ 0.1 |
|---|---|---|---|---|---|---|---|
| DP0209.02 | 40 | 24 | 2.53 | 0.062 | | 0.040 | |
| DP0209.07 | 34 | 22 | 2.31 | 0.044 | | 0.030 | |
| DP0209.10 | 40 | 24 | 3.28 | 0.329 | | 0.244 | |
| DP0209.11 | 40 | 24 | 3.92 | 1.000 | | 0.833 | |
| DP0209.13 | 40 | 25 | 1.84 | 0.003 | | 0.001 | |
| DP0209.19 | 40 | 24 | 1.86 | 0.006 | | 0.003 | |
| DP0209.25 | 39 | 22 | 3.23 | 0.349 | | 0.253 | |
| DP0209.26 | 38 | 24 | 3.07 | 0.380 | | 0.287 | |
| DP0209.28 | 32 | 21 | 4.85 | 0.201 | | 0.269 | |
| DP0209.30 | 40 | 24 | 2.48 | 0.061 | | 0.041 | |
| DP0209.34 | 39 | 24 | 4.19 | 0.768 | | 0.933 | |
| DP0209.35 | 40 | 25 | 2.49 | 0.059 | | 0.036 | |
| ZH11-TC | 40 | 24 | 3.66 | | | | |
| DP0158 | 39 | 24 | 3.78 | | | | |
| DP0209 (construct) | | | 3.10 | 0.175 | | 0.115 | |

Example 6

Laboratory Paraquat Assays of Transgenic Rice Plants

Paraquat (1,1-dimethyl-4,4-bipyridinium dichloride), is a foliar-applied and non-selective bipyridinium herbicide, and is one of the most widely used herbicides in the world, controlling weeds in a huge variety of crops like corn, rice, soybean etc. In plant cells, paraquat mainly targets to the chloroplasts by accepting electrons from photosystem I and then reacting with oxygen to produce superoxide and hydrogen peroxide, which alters plants' ability to resist photooxidative stress. Drought stress usually leads to increased reactive oxygen species (ROS) in plants and sometimes, the drought tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, the paraquat tolerance of the drought tolerance transgenic rice plants was tested.

Paraquat Assay Methods:

Transgenic rice plants from 8-10 transgenic lines of each transgenic rice line were tested by paraquat assay. Tissue-cultured Zhonghua 11 plants (ZH11-TC) and empty vector transgenic plants (DP0158) were used as controls. $T_2$ transgenic seeds were sterilized and germinated as described in Example 4, and cultivated in growth room with the temperature of 28-30° C. and humidity of ~30%. The germinated seeds were placed into a tube with a hole at the bottom, and cultured in water at 30° C. for 5 days till one-leaf and one-terminal bud stage. Uniform seedlings about 3.5-4 cm in height were selected for paraquat testing. Randomized block design was used in this experiment. There were five blocks, each of which has 16×12 holes. Each transgenic line was placed in one row (12 plants/line), and the ZH11-TC and DP0158 controls were placed randomly in 3 rows (3×12 plants) in one block. Then the seedlings were treated with 0.8 μM paraquat solution for 7 days with a 10-h-light/14-h-dark cycle, and the treated seedlings first encountered dark and took up the paraquat solution which was changed every two days. After treated for 7 days, the green seedlings were counted. Those seedlings that maintain green in whole without damage were considered as paraquat tolerant seedlings; while those with bleached leaves or stem were not considered as paraquat tolerant seedling.

Tolerant rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", and statistic method of "SAS® PROC GLIMMIX".

Paraquat Assay Results:

1) Paraquat Validation Results of OsGSTU41 (DP0043) Transgenic Rice

For OsGSTU41 transgenic rice, in the first experiment, 231 of the 540 transgenic seedlings (43%) kept green and showed tolerant phenotype after treatment with 0.8 μM paraquat solutions for 7 days, while 48 of the 240 (20%) seedlings from ZH11-TC control and 55 of the 180 (31%) seedlings from DP0158 showed tolerant phenotype under the same condition. The tolerance rate of OsGSTU41 transgenic seedlings was significantly higher than that of ZH11-TC (P value=0.0000) and DP0158 (P value=0.0087) controls. The OsGSTU41 transgenic seedlings grew better after treatment with 0.8 μM paraquat solutions compared with the ZH11-TC and DP0158 seedlings. These results indicate that the OsGSTU41 transgenic seedling exhibited enhanced paraquat tolerance compared with both ZH11-TC and DP0158 controls at construct level.

Further analysis at transgenic line level, as shown in Table 29, indicates that all of the eight OsGSTU41 transgenic lines had greater tolerance rates and five lines showed significantly higher tolerance rates compared with ZH11-TC control; and when compared with the DP0158 control, five lines had greater tolerance rates and four lines showed significantly greater tolerance rates. These results show that over-expression of the OsGSTU41 gene increased the paraquat tolerance or antioxidative ability in the transgenic plants.

TABLE 29

Paraquat tolerance assay of OsGSTU41 transgenic rice plants at transgenic line level (1st experiment)

| Line ID | Number of tolerant seedlings | Number of total seedlings | Tolerance rate (%) | CK = ZH11-TC Pvalue | CK = ZH11-TC P ≤ 0.05 | CK = DP0158 Pvalue | CK = DP0158 P ≤ 0.05 |
|---|---|---|---|---|---|---|---|
| DP0043.03 | 16 | 60 | 27 | 0.2653 |   | 0.5700 |   |
| DP0043.11 | 16 | 60 | 27 | 0.2653 |   | 0.5700 |   |
| DP0043.12 | 50 | 120 | 42 | 0.0000 | Y | 0.0530 |   |
| DP0043.15 | 14 | 60 | 23 | 0.5707 |   | 0.2900 |   |
| DP0043.19 | 30 | 60 | 50 | 0.0000 | Y | 0.0089 | Y |
| DP0043.25 | 37 | 60 | 62 | 0.0000 | Y | 0.0000 | Y |
| DP0043.26 | 27 | 60 | 45 | 0.0002 | Y | 0.0465 | Y |
| DP0043.28 | 41 | 60 | 68 | 0.0000 | Y | 0.0000 | Y |
| ZH11-TC | 48 | 240 | 20 |   |   |   |   |
| DP0158 | 55 | 180 | 31 |   |   |   |   |

In the second experiment, 372 of the 600 transgenic seedlings (62%) kept green and showed tolerant phenotype after treated with 0.8 μM paraquat solutions for 7 days, while 86 of the 180 (48%) seedlings from ZH11-TC control and 73 of the 180 (41%) seedlings from DP0158 showed tolerant phenotype under the same condition. The tolerance rate of OsGSTU41 transgenic seedlings was significantly higher than ZH11-TC (P value=0.0008) and DP0158 (P value=0.0000) controls. Analysis at transgenic line level indicates that nine OsGSTU41 transgenic lines had greater tolerance rates than ZH11-TC and DP0158. Five lines showed significantly higher tolerance rates compared with ZH11-TC control, and eight lines showed greater tolerance rates than DP0158 control (Table 30). These results further show that OsGSTU41 transgenic rice had enhanced paraquat tolerance and over-expression of the OsGSTU41 gene increased the paraquat tolerance or antioxidative ability in the transgenic plants.

As described in Example 4 and 5, over-expression of OsGSTU41 gene increased the drought tolerance of rice plants at seedling and mature stage. These cross-validations further confirm that the OsGSTU41 gene plays a role in increasing antioxidative ability and then improve drought tolerance in plant.

2) Paraquat Validation Results of OsPPCK4 (DP0058) Transgenic Rice

In the first experiment, 380 of the 600 OsPPCK4 transgenic seedlings (63%) kept green and showed tolerant phenotype after 0.8 μM paraquat solution treated for 7 days, while 76 of the 180 (42%) seedlings from ZH11-TC control and 65 of the 180 (36%) seedlings from DP0158 control showed tolerant phenotype. The tolerance rate of all screened OsPPCK4 transgenic seedlings was significantly greater than that of the ZH11-TC (P value=0.0000) and DP0158 (P value=0.0000) controls. The OsPPCK4 transgenic seedlings grew better than ZH11-TC and DP0158 seedlings. All these results show that OsPPCK4 transgenic seedlings exhibited enhanced paraquat tolerance compared with both controls of ZH11-TC and DP0158 seedlings at construct level.

Further analysis at transgenic line level is illustrated in Table 31. Nine lines had greater tolerance rates compared with ZH11-TC and DP0158 controls. The tolerance rates of six lines were significantly greater than that of both ZH11-TC and DP0158 controls. These results demonstrate that OsPPCK4 transgenic rice plants had enhanced paraquat tolerance compared with both controls of ZH11-TC and DP0158 rice plants at construct and transgenic line level at seedling stages.

TABLE 30

Paraquat tolerance assay of OsGSTU41 transgenic rice plants at transgenic line level (2nd experiment)

| Line ID | Number of tolerant seedlings | Number of total seedlings | Tolerance rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0043.03 | 34 | 60 | 57 | 0.2382 |   | 0.0346 | Y |
| DP0043.04 | 33 | 60 | 55 | 0.3367 |   | 0.0567 |   |
| DP0043.11 | 36 | 60 | 60 | 0.1072 |   | 0.0118 | Y |
| DP0043.12 | 42 | 60 | 70 | 0.0046 | Y | 0.0003 | Y |
| DP0043.15 | 40 | 60 | 67 | 0.0146 | Y | 0.0010 | Y |
| DP0043.19 | 41 | 60 | 68 | 0.0083 | Y | 0.0005 | Y |
| DP0043.21 | 49 | 60 | 82 | 0.0000 | Y | 0.0000 | Y |
| DP0043.25 | 41 | 60 | 68 | 0.0083 | Y | 0.0005 | Y |
| DP0043.26 | 21 | 60 | 35 | 0.0909 |   | 0.4481 |   |
| DP0043.28 | 35 | 60 | 58 | 0.1626 |   | 0.0205 | Y |
| ZH11-TC | 86 | 180 | 48 |   |   |   |   |
| DP0158 | 73 | 180 | 41 |   |   |   |   |

TABLE 31

Paraquat tolerance assay of OsPPCK4 transgenic rice plants at transgenic line level (1st experiment)

| Line ID | Number of tolerant seedlings | Number of total seedlings | Tolerance rate (%) | CK = ZH11-TC Pvalue | P ≤ 0.05 | CK = DP0158 Pvalue | P ≤ 0.05 |
|---|---|---|---|---|---|---|---|
| DP0058.02 | 51 | 60 | 85 | 0.0000 | Y | 0.0000 | Y |
| DP0058.03 | 30 | 60 | 50 | 0.2950 |   | 0.0611 |   |
| DP0058.04 | 37 | 60 | 62 | 0.0115 | Y | 0.0011 | Y |
| DP0058.07 | 34 | 60 | 57 | 0.0561 |   | 0.0070 | Y |
| DP0058.10 | 39 | 60 | 65 | 0.0035 | Y | 0.0003 | Y |
| DP0058.12 | 20 | 60 | 33 | 0.2264 |   | 0.6964 |   |
| DP0058.13 | 53 | 60 | 88 | 0.0000 | Y | 0.0000 | Y |
| DP0058.14 | 36 | 60 | 60 | 0.0201 | Y | 0.0021 | Y |
| DP0058.15 | 26 | 60 | 43 | 0.8798 |   | 0.3195 |   |
| DP0058.18 | 54 | 60 | 90 | 0.0000 | Y | 0.0000 | Y |
| ZH11-TC | 76 | 180 | 42 |   |   |   |   |
| DP0158 | 65 | 180 | 36 |   |   |   |   |

In the second experiment, 265 of the 540 OsPPCK4 transgenic seedlings (49%) kept green and showed tolerant phenotype after 0.8 μM paraquat solution treated for 7 days, while 88 of the 240 (37%) ZH11-TC seedlings and 75 of the 180 (42%) DP0158 seedlings showed tolerant phenotype at construct level. The paraquat tolerance rate of OsPPCK4 transgenic seedlings was significantly higher than ZH11-TC control (P value=0.0030) and higher than DP0158 control (P value=0.1075) at construct level. These results indicate that the OsPPCK4 transgenic seedlings had enhanced paraquat tolerance at construct level.

The analysis at transgenic line level indicates that five transgenic lines had higher tolerance rates compared with either ZH11-TC or DP0158 controls (Table 32). Five lines had significantly higher tolerance rates than ZH11-TC control, and four lines had significantly higher tolerance rates than DP0158 control. These results demonstrate that OsPPCK4 transgenic rice plants exhibited enhanced paraquat tolerance compared with both ZH11-TC and DP0158 controls at construct and transgenic line level at seedling stage.

In the third experiment, 290 of the 540 OsPPCK4 transgenic seedlings (54%) kept green and showed tolerant phenotype after 0.8 μM paraquat solution treated for 7 days, while 77 of the 180 (43%) ZH11-TC seedlings and 89 of the 180 (49%) DP0158 seedlings showed tolerant phenotype at construct level. The paraquat tolerance rate of OsPPCK4 transgenic seedlings was also significantly higher than ZH11-TC control (P value=0.0086) and higher than DP0158 control (P value=0.2236) at construct level.

The analysis at transgenic line level indicates that six transgenic lines had higher tolerance rates compared with either ZH11-TC or DP0158 controls (Table 33). Four lines had significantly higher tolerance rates than ZH11-TC control, and two lines had significantly higher tolerance rates than DP0158 control. These results demonstrate that OsPPCK4 transgenic rice plants exhibited enhanced paraquat tolerance compared with both ZH11-TC and DP0158 controls at construct and transgenic line level at seedling stage. Over-expression of OsPPCK4 gene increased the paraquat tolerance or antioxidative activity of transgenic plants.

TABLE 32

Paraquat tolerance assay of OsPPCK4 transgenic rice plants at transgenic line level (2nd experiment)

| Line ID | Number of tolerant seedlings | Number of total seedlings | Tolerance rate (%) | CK = ZH11-TC Pvalue | P ≤ 0.05 | CK = DP0158 Pvalue | P ≤ 0.05 |
|---|---|---|---|---|---|---|---|
| DP0058.02 | 42 | 60 | 70 | 0.0000 | Y | 0.0004 | Y |
| DP0058.03 | 21 | 60 | 35 | 0.8107 |   | 0.3628 |   |
| DP0058.07 | 23 | 60 | 38 | 0.8104 |   | 0.6487 |   |
| DP0058.10 | 33 | 60 | 55 | 0.0124 | Y | 0.0767 |   |
| DP0058.12 | 39 | 60 | 65 | 0.0002 | Y | 0.0029 | Y |
| DP0058.13 | 36 | 60 | 60 | 0.0019 | Y | 0.0167 | Y |
| DP0058.14 | 17 | 60 | 28 | 0.2302 |   | 0.0710 |   |
| DP0058.15 | 14 | 60 | 23 | 0.0568 |   | 0.0142 |   |
| DP0058.18 | 40 | 60 | 67 | 0.0001 | Y | 0.0015 | Y |
| ZH11-TC | 88 | 240 | 37 |   |   |   |   |
| DP0158 | 75 | 180 | 42 |   |   |   |   |

TABLE 33

Paraquat tolerance assay of OsPPCK4 transgenic rice plants at transgenic line level (3$^{rd}$ experiment)

| Line ID | Number of tolerant seedlings | Number of total seedlings | Tolerance rate % (%) | CK = ZH11-TC P value | P ≤ 0.05 | CK = DP0158 Pvalue | P ≤ 0.05 |
|---|---|---|---|---|---|---|---|
| DP0058.02 | 32 | 60 | 53 | 0.1612 | | 0.6038 | |
| DP0058.03 | 37 | 60 | 62 | 0.0146 | Y | 0.1071 | |
| DP0058.07 | 13 | 60 | 22 | 0.0057 | | 0.0005 | |
| DP0058.10 | 17 | 60 | 28 | 0.0534 | | 0.0067 | |
| DP0058.12 | 35 | 60 | 58 | 0.0418 | Y | 0.2383 | |
| DP0058.13 | 42 | 60 | 70 | 0.0007 | Y | 0.0082 | Y |
| DP0058.14 | 26 | 60 | 43 | 0.9402 | | 0.4154 | |
| DP0058.15 | 34 | 60 | 57 | 0.0678 | | 0.3368 | |
| DP0058.18 | 54 | 60 | 90 | 0.0000 | Y | 0.0000 | Y |
| ZH11-TC | 77 | 180 | 43 | | | | |
| DP0158 | 89 | 180 | 49 | | | | |

Over-expression of OsPPCK4 gene increased the drought tolerance of transgenic rice plants as illustrated in Example 4 and 5. These cross-validations by three different assays confirm that OsPPCK4 gene increases drought tolerance in plants.

3) Paraquat Validation Results of OsCAM2 (DP0059) Transgenic Rice

In the first experiment, after treated with paraquat solution, 341 of the 480 OsCAM2 transgenic seedlings (71%) kept green and showed tolerant phenotype, whereas only 165 of the 300 ZH11-TC seedlings (55%) and 71 of the 180 DP0158 seedlings (39%) showed paraquat tolerant phenotype. The paraquat tolerance rate of OsCAM2 transgenic plants was significantly higher than that of ZH11-TC (P value=0.0000) and DP0158 (P value=0.0000) controls at construct level. The OsCAM2 transgenic seedlings grew better than either ZH11-TC or DP0158 seedlings after paraquat solution treatment. These results indicate that the OsCAM2 transgenic seedlings had enhanced paraquat tolerance compared with both of ZH11-TC and DP0158 controls at construct level.

The analysis at transgenic line level is displayed in Table 34. All the eight lines had greater tolerance rates than ZH11-TC and DP0158 seedlings, and the eight lines also showed significantly greater paraquat tolerance rates than DP0158. These results further demonstrate over-expression of OsCAM2 gene enhanced the paraquat tolerance in transgenic plants at both construct level and transgenic line level at seedling stage.

In the second experiment, after treated with paraquat solution, 287 of the 480 OsCAM2 transgenic seedlings (60%) kept green and showed tolerant phenotype, whereas 134 of the 300 ZH11-TC seedlings (45%) and 75 of the 180 DP0158 seedlings (42%) showed paraquat tolerant phenotype. The paraquat tolerance rate of OsCAM2 transgenic plants was significantly higher than that of ZH11-TC (P value=0.0000) and DP0158 (P value=0.0000) controls at construct level. The analysis at transgenic line level is displayed in Table 35. Five lines had greater tolerance rates than ZH11-TC and DP0158 seedlings, and four lines showed significantly greater paraquat tolerance rates than both ZH11-TC and DP0158 controls. These results further demonstrate OsCAM2 transgenic rice exhibited better paraquat tolerance and/or antioxidative activity, and over-expression of OsCAM2 gene enhanced the paraquat tolerance in transgenic plants at both construct level and transgenic line level at seedling stage.

As described in Example 4 and 5, over-expression of OsCAM2 gene can also increase the drought tolerance of the transgenic plants. These cross-validations by two different assays indicate the function of OsCAM2 gene in increasing drought tolerance in plant.

TABLE 34

Paraquat tolerance assay of OsCAM2 transgenicrice plants at transgenic line level (1$^{st}$ experiment)

| Line ID | Number of tolerant seedlings | Number of total seedlings | Tolerancerate (%) | CK = ZH11-TC Pvalue | P ≤ 0.05 | CK = DP0158 Pvalue | P ≤ 0.05 |
|---|---|---|---|---|---|---|---|
| DP0059.01 | 35 | 60 | 58 | 0.6370 | | 0.0140 | Y |
| DP0059.04 | 49 | 60 | 82 | 0.0005 | Y | 0.0000 | Y |
| DP0059.05 | 41 | 60 | 68 | 0.0632 | | 0.0003 | Y |
| DP0059.09 | 42 | 60 | 70 | 0.0376 | Y | 0.0002 | Y |
| DP0059.11 | 48 | 60 | 80 | 0.0010 | Y | 0.0000 | Y |
| DP0059.12 | 48 | 60 | 80 | 0.0010 | Y | 0.0000 | Y |
| DP0059.13 | 38 | 60 | 63 | 0.2404 | | 0.0024 | Y |
| DP0059.14 | 40 | 60 | 67 | 0.1025 | | 0.0007 | Y |
| ZH11-TC | 165 | 300 | 55 | | | | |
| DP0158 | 71 | 180 | 39 | | | | |

TABLE 35

Paraquat tolerance assay of OsCAM2 transgenicrice plants at transgenic line level ($2^{nd}$ experiment)

| Line ID | Number of tolerant seedlings | Number of total seedlings | Tolerance rate (%) | CK = ZH11-TC | | CK = DP0158 | |
|---|---|---|---|---|---|---|---|
| | | | | P value | P ≤ 0.05 | P value | P ≤ 0.05 |
| DP0059.01 | 37 | 60 | 62 | 0.0202 | Y | 0.0099 | Y |
| DP0059.04 | 49 | 60 | 82 | 0.0000 | Y | 0.0000 | Y |
| DP0059.05 | 27 | 60 | 45 | 0.9618 | | 0.6519 | |
| DP0059.09 | 45 | 60 | 75 | 0.0001 | Y | 0.0000 | Y |
| DP0059.11 | 48 | 60 | 80 | 0.0000 | Y | 0.0000 | Y |
| DP0059.12 | 31 | 60 | 52 | 0.3249 | | 0.1824 | |
| DP0059.13 | 25 | 60 | 42 | 0.6714 | | 0.9991 | |
| DP0059.14 | 25 | 60 | 42 | 0.6716 | | 0.9989 | |
| ZH11-TC | 134 | 300 | 45 | | | | |
| DP0158 | 75 | 180 | 42 | | | | |

4) Paraquat Validation Results of OsDN-DTP4 (DP0167) Transgenic Rice

In the first experiment, construct level analysis of all OsDN-DTP4 transgenic rice plants indicates that, 486 of the 600 seedlings (81%) kept green and showed tolerant phenotype, while 101 of the 180 (56%) ZH11-TC seedlings showed tolerant phenotype, and 71 of 180 (39%) DP0158 seedlings showed tolerant phenotype. The tolerance rate of all tested OsDN-DTP4 transgenic seedlings was significantly higher than that of the ZH11-TC (P value=0.0000) and DP0158 (P value=0.0000) controls. These results indicate that the OsDN-DTP4 transgenic seedlings grew better and enhanced paraquat tolerance compared with either ZH11-TC or DP0158 seedlings at construct level after treated by 0.8 μM paraquat solutions.

Further analysis at transgenic line level indicates that all of the ten lines had greater tolerance rates compared with ZH11-TC and DP0158 controls (Table 36). Nine lines compared with ZH11-TC control and ten lines compared with DP0158 control had significantly higher tolerance rates, respectively. These results demonstrate that OsDN-DTP4 transgenic rice plants exhibited enhanced paraquat tolerance compared with both ZH11-TC and DP0158 controls at construct and transgenic line level at seedling stage.

In the second experiment, 366 of the 600 seedlings (61%) kept green and showed tolerant phenotype, while 63 of the 180 (35%) ZH11-TC seedlings showed tolerant phenotype, and 98 of the 180 (54%) DP0158 seedlings showed tolerant phenotype. The tolerance rate of all tested OsDN-DTP4 transgenic seedlings was significantly higher than ZH11-TC (P value=0.0000) and DP0158 (P value=0.0491) controls. These results indicate that the OsDN-DTP4 transgenic seedlings grew better and enhanced paraquat tolerance compared with either ZH11-TC or DP0158 seedlings at construct level.

Analysis at transgenic line level indicates that eight lines exhibited greater tolerance rates compared with ZH11-TC and DP0158 controls (Table 37). Eight lines compared with ZH11-TC control and two lines compared with DP0158 control had significantly higher tolerance rates, respectively. These results further demonstrate that OsDN-DTP4 transgenic rice plants exhibited enhanced paraquat tolerance and/or antioxidative activity at seedling stage. Over-expression of OsDN-DTP4 gene increased the paraquat tolerance and/or antioxidative activity in transgenic plants.

As described in Example 4, over-expression of OsDN-DTP4 can also increase the drought tolerance of the transgenic plants. These cross-validations by two different assays demonstrate that OsDN-DTP4 expression increased drought tolerance in plant.

TABLE 36

Paraquat tolerance assay of OsDN-DTP4 transgenic rice plant at transgenic line level ($1^{st}$ experiment)

| Line ID | Number of tolerant seedlings | Number of total seedlings | Tolerance rate (%) | CK = ZH11-TC | | CK = DP0158 | |
|---|---|---|---|---|---|---|---|
| | | | | Pvalue | P ≤ 0.05 | Pvalue | P ≤ 0.05 |
| DP0167.01 | 52 | 60 | 87 | 0.0002 | Y | 0.0000 | Y |
| DP0167.02 | 52 | 60 | 87 | 0.0002 | Y | 0.0000 | Y |
| DP0167.03 | 48 | 60 | 80 | 0.0019 | Y | 0.0000 | Y |
| DP0167.04 | 48 | 60 | 80 | 0.0019 | Y | 0.0000 | Y |
| DP0167.05 | 52 | 60 | 87 | 0.0002 | Y | 0.0000 | Y |
| DP0167.06 | 47 | 60 | 78 | 0.0037 | Y | 0.0000 | Y |
| DP0167.07 | 46 | 60 | 77 | 0.0068 | Y | 0.0000 | Y |
| DP0167.11 | 40 | 60 | 67 | 0.1532 | | 0.0000 | Y |
| DP0167.12 | 46 | 60 | 77 | 0.0068 | Y | 0.0000 | Y |
| DP0167.13 | 55 | 60 | 92 | 0.0000 | Y | 0.0000 | Y |
| ZH11-TC | 101 | 180 | 56 | | | | |
| DP0158 | 71 | 180 | 39 | | | | |

TABLE 37

Paraquat tolerance assay of OsDN-DTP4 transgenic rice plant at transgenic line level (2$^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0167.02 | 39 | 60 | 65 | 0.0002 | Y | 0.1573 | |
| DP0167.03 | 37 | 60 | 62 | 0.0007 | Y | 0.3313 | |
| DP0167.04 | 44 | 60 | 73 | 0.0000 | Y | 0.0132 | Y |
| DP0167.05 | 36 | 60 | 60 | 0.0013 | Y | 0.4542 | |
| DP0167.06 | 24 | 60 | 40 | 0.4863 | | 0.0578 | |
| DP0167.07 | 36 | 60 | 60 | 0.0013 | Y | 0.4542 | |
| DP0167.11 | 38 | 60 | 63 | 0.0004 | Y | 0.2326 | |
| DP0167.12 | 41 | 60 | 68 | 0.0000 | Y | 0.0645 | |
| DP0167.13 | 43 | 60 | 72 | 0.0000 | Y | 0.0234 | Y |
| ZH11-TC | 63 | 180 | 35 | | | | |
| DP0158 | 98 | 180 | 54 | | | | |

5) Paraquat Validation Results of OsLecRK4.1 (DP0173) Transgenic Rice

For OsLecRK4.1 transgenic rice, in the first experiment, 462 of the 600 OsLecRK4.1 transgenic seedlings (77%) kept green and showed tolerant phenotype after treated with paraquat solutions, whereas 99 of the 180 (55%) ZH11-TC seedlings and 95 of the 180 (53%) DP0158 seedlings showed paraquat tolerant phenotype respectively. The tolerance rate of OsLecRK4.1 transgenic seedlings was significantly higher than that of ZH11-TC (P value=0.0000) and DP0158 (P value=0.0000) controls. The OsLecRK4.1 transgenic seedlings grew better after paraquat solution treatment compared with the ZH11-TC or DP0158 seedlings. All these results demonstrate that OsLecRK4.1 transgenic seedlings exhibited enhanced paraquat tolerance compared with both of ZH11-TC and DP0158 controls at construct level.

As shown in Table 38, nine of the ten OsLecRK4.1 transgenic lines had higher tolerance rates than ZH11-TC and DP0158 controls at transgenic line level. And seven lines compared with ZH11-TC control and 8 lines compared with DP0158 control had significantly higher tolerance rates. These results further demonstrate that over-expression of OsLecRK4.1 gene increased paraquat tolerance or antioxidative activity of transgenic rice plants.

In the second experiment, 425 of the 600 OsLecRK4.1 transgenic seedlings (71%) kept green and showed tolerant phenotype after treated with paraquat solutions, while 103 of the 180 (57%) ZH11-TC seedlings and 108 of the 180 (60%) DP0158 seedlings showed paraquat tolerant phenotype respectively. The tolerance rate of OsLecRK4.1 transgenic seedlings was significantly higher than ZH11-TC (P value=0.0002) and DP0158 (P value=0.0020) controls. Analysis at transgenic line level shows that nine transgenic lines had higher tolerance rates than ZH11-TC and DP0158 controls, four lines compared with ZH11-TC control and three lines compared with DP0158 control exhibited significantly higher tolerance rates (Table 39). These results further demonstrate that over-expression of OsLecRK4.1 gene increased paraquat tolerance or antioxidative activity of transgenic rice plants.

Over-expression of OsLecRK4.1 gene enhanced the drought tolerance of the transgenic rice plants as described in Example 5. These cross-validations by two different assays indicate that OsLecRK4.1 gene functions in increasing drought tolerance in plant.

TABLE 38

Paraquat tolerance assay of OsLecRK4.1 transgenic rice plant at transgenic line level (1$^{st}$ experiment)

| Line ID | Number of tolerant seedlings | Number of total seedlings | Tolerance rate (%) | CK = ZH11-TC Pvalue | P ≤ 0.05 | CK = DP0158 Pvalue | P ≤ 0.05 |
|---|---|---|---|---|---|---|---|
| DP0173.01 | 48 | 60 | 80 | 0.0014 | Y | 0.0007 | Y |
| DP0173.02 | 34 | 60 | 57 | 0.8227 | | 0.6027 | |
| DP0173.04 | 41 | 60 | 68 | 0.0762 | | 0.0408 | Y |
| DP0173.05 | 30 | 60 | 50 | 0.5039 | | 0.7105 | |
| DP0173.06 | 50 | 60 | 83 | 0.0004 | Y | 0.0002 | Y |
| DP0173.11 | 50 | 60 | 83 | 0.0004 | Y | 0.0002 | Y |
| DP0173.12 | 58 | 60 | 97 | 0.0000 | Y | 0.0000 | Y |
| DP0173.13 | 45 | 60 | 75 | 0.0091 | Y | 0.0043 | Y |
| DP0173.14 | 54 | 60 | 90 | 0.0000 | Y | 0.0000 | Y |
| DP0173.15 | 52 | 60 | 87 | 0.0001 | Y | 0.0000 | Y |
| ZH11-TC | 99 | 180 | 55 | | | | |
| DP0158 | 95 | 180 | 53 | | | | |

TABLE 39

Paraquat tolerance assay of OsLecRK4.1 transgenic rice plant at transgenic line level (2nd experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0173.01 | 55 | 60 | 92 | 0.0000 | Y | 0.0001 | Y |
| DP0173.02 | 43 | 60 | 72 | 0.0523 |   | 0.1105 |   |
| DP0173.04 | 44 | 60 | 73 | 0.0311 | Y | 0.0689 |   |
| DP0173.05 | 37 | 60 | 62 | 0.5460 |   | 0.8196 |   |
| DP0173.06 | 38 | 60 | 63 | 0.4066 |   | 0.6475 |   |
| DP0173.11 | 36 | 60 | 60 | 0.7060 |   | 0.9996 |   |
| DP0173.12 | 47 | 60 | 78 | 0.0055 | Y | 0.0136 | Y |
| DP0173.13 | 31 | 60 | 52 | 0.4543 |   | 0.2606 |   |
| DP0173.14 | 53 | 60 | 88 | 0.0001 | Y | 0.0003 | Y |
| DP0173.15 | 41 | 60 | 68 | 0.1325 |   | 0.2519 |   |
| ZH11-TC | 103 | 180 | 57 |   |   |   |   |
| DP0158 | 108 | 180 | 60 |   |   |   |   |

6) Paraquat Validation Results of OsLecRK4.2 (DP0209) Transgenic Rice

In the first experiment, 600 OsLecRK4.2 transgenic seedlings were considered as a whole and analyzed at construct level. 221 of the 600 OsLecRK4.2 transgenic seedlings (37%) kept green and showed tolerant phenotype, while only 30 of the 240 (17%) ZH11-TC seedlings and 29 of the 180 (16%) DP0158 seedlings showed tolerant phenotype. The paraquat tolerance rate of OsLecRK4.2 transgenic seedlings was significantly higher than that of ZH11-TC (P value=0.0000) and DP0158 controls (P value=0.0000) at construct level. These results indicate that OsLecRK4.2 transgenic seedlings had enhanced paraquat tolerance at construct level, and the OsLecRK4.2 transgenic seedlings grew better after treated by 0.8 µM paraquat solutions compared with the ZH11-TC and DP0158 seedlings.

The analysis at transgenic line level indicates that nine of the ten tested transgenic lines had higher tolerance rates compared with either ZH11-TC or DP0158 controls (Table 40). Eight lines showed significantly higher tolerance rates than that of ZH11-TC and DP0158 controls respectively as shown in Table 37. These results demonstrate that OsLecRK4.2 transgenic rice plants exhibited enhanced paraquat tolerance compared with both ZH11-TC and DP0158 controls at construct and transgenic line level at seedling stage. Over-expression of OsLecRK4.2 gene increased the paraquat tolerance or antioxidative activity in transgenic plants.

TABLE 40

Paraquat tolerance assay of OsLecRK4.2 transgenic rice plant at transgenic line level (1st experiment)

| Line ID | Number of tolerant seedlings | Number of total seedlings | Tolerancerate rate (%) | CK = ZH11-TC P value | P ≤ 0.05 | CK = DP0158 P value | P ≤ 0.05 |
|---|---|---|---|---|---|---|---|
| DP0209.01 | 32 | 60 | 53 | 0.0000 | Y | 0.0000 | Y |
| DP0209.02 | 22 | 60 | 37 | 0.0022 | Y | 0.0016 | Y |
| DP0209.05 | 22 | 60 | 37 | 0.0022 | Y | 0.0016 | Y |
| DP0209.06 | 23 | 60 | 38 | 0.0011 | Y | 0.0008 | Y |
| DP0209.08 | 27 | 60 | 45 | 0.0000 | Y | 0.0000 | Y |
| DP0209.09 | 31 | 60 | 52 | 0.0000 | Y | 0.0000 | Y |
| DP0209.10 | 7 | 60 | 12 | 0.3576 |   | 0.4075 |   |
| DP0209.11 | 22 | 60 | 37 | 0.0022 | Y | 0.0016 | Y |
| DP0209.12 | 14 | 60 | 23 | 0.2526 | Y | 0.2120 |   |
| DP0209.14 | 21 | 60 | 35 | 0.0044 | Y | 0.0032 | Y |
| ZH11-TC | 30 | 180 | 17 |   |   |   |   |
| DP0158 | 29 | 180 | 16 |   |   |   |   |

In the second experiment, 351 of the 600 OsLecRK4.2 transgenic seedlings (59%) kept green and showed tolerant phenotype, while 66 of the 180 (37%) ZH11-TC seedlings and 85 of the 180 (47%) DP0158 seedlings showed tolerant phenotype. The paraquat tolerance rate of OsLecRK4.2 transgenic seedlings was significantly higher than ZH11-TC (P value=0.0000) and DP0158 controls (P value=0.0080) at construct level. These results indicate that OsLecRK4.2 transgenic seedlings had enhanced paraquat tolerance at construct level.

The analysis at transgenic line level indicates that eight lines exhibited higher tolerance rates compared with either ZH11-TC or DP0158 controls (Table 41). Eight lines showed significantly higher tolerance rates than ZH11-TC and five lines exhibited significantly higher tolerance rates than DP0158 controls respectively. These results further demonstrate that OsLecRK4.2 transgenic rice plants exhibited enhanced paraquat tolerance at seedling stage. Over-expression of OsLecRK4.2 gene increased the paraquat tolerance or antioxidative activity in transgenic plants.

Over-expression of OsLecRK4.2 gene can also increase the drought tolerance of transgenic rice plants as illustrated in Example 5. These cross-validations by two different assays confirm that OsLecRK4.2 gene can increase drought tolerance in plants.

TABLE 41

Paraquat tolerance assay of OsLecRK4.2 transgenic rice plant at transgenic line level ($2^{nd}$ experiment)

| Line ID | Number of tolerant seedlings | Number of total seedlings | Tolerance rate (%) | CK = ZH11-TC | | CK = DP0158 | |
|---|---|---|---|---|---|---|---|
| | | | | P value | P ≤ 0.05 | P value | P ≤ 0.05 |
| DP0209.01 | 42 | 60 | 70 | 0.0000 | Y | 0.0038 | Y |
| DP0209.02 | 22 | 60 | 37 | 1.0000 | | 0.1607 | |
| DP0209.05 | 35 | 60 | 58 | 0.0051 | Y | 0.1424 | |
| DP0209.06 | 33 | 60 | 55 | 0.0160 | Y | 0.3014 | |
| DP0209.08 | 31 | 60 | 52 | 0.0458 | Y | 0.5531 | |
| DP0209.09 | 44 | 60 | 73 | 0.0000 | Y | 0.0011 | Y |
| DP0209.10 | 24 | 60 | 40 | 0.6458 | | 0.3350 | |
| DP0209.11 | 43 | 60 | 72 | 0.0000 | Y | 0.0020 | Y |
| DP0209.12 | 38 | 60 | 63 | 0.0008 | Y | 0.0358 | Y |
| DP0209.14 | 39 | 60 | 65 | 0.0004 | Y | 0.0212 | Y |
| ZH11-TC | 66 | 180 | 37 | | | | |
| DP0158 | 85 | 180 | 47 | | | | |

Example 7

Transformation and Evaluation of Maize with Rice Drought Tolerance Genes

Maize plants can be transformed to over-express *Oryza sativa* drought tolerance genes or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter or a tissue-preferred promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999. The *Agrobacterium*-mediated transformation process involves bacterium inoculation, co-cultivation, resting, selection and plant regeneration.

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in maize to enhance drought tolerance.

Example 8

Transformation and Evaluation of Gaspe Flint Derived Maize Lines

As described in Example 7, maize plants can be transformed to over-express the rice drought tolerance genes, or corresponding homologs from another species. In certain circumstances, recipient plant cells can be from a uniform maize line having a short life cycle ("fast cycling"), a reduced size, and high transformation potential, and are disclosed in Tomes et al. U.S. Pat. No. 7,928,287.

The population of transgenic ($T_0$) plants resulting from the transformed maize embryos can be grown in a controlled greenhouse environment using a modified randomized block design to reduce or eliminate environmental error. For example, a group of 30 plants, comprising 24 transformed experimental plants and 6 control plants (collectively, a "replicate group"), are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of 30 plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

Each plant in the line population is identified and tracked throughout the evaluation process, and the data gathered from that plant are automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor (U.S. Pat. Nos. 7,403,855 and 7,702,462).

Each greenhouse plant in the $T_0$ line population, including any control plants, is analyzed for agronomic characteristics of interest, and the agronomic data for each plant are recorded or stored in a manner so as to be associated with the identifying data for that plant. Confirmation of a phenotype (gene effect) can be accomplished in the $T_1$ generation with a similar experimental design to that described above.

Example 9

Laboratory Drought Assays of Rice Drought Tolerance Genes in *Arabidopsis*

To understand whether rice drought tolerance genes can improve dicot plants' drought tolerance, or other traits, the rice drought tolerance gene over-expression vectors were transformed into *Arabidopsis* (Columbia) using floral dip method by *Agrobacterium* mediated transformation procedure and transgenic plants were identified (Clough, S. T. and Bent, A. F. (1998) *The Plant Journal* 16, 735-743; Zhang, X. et al. (2006) *Nature Protocols* 1: 641-646).

A 16.8-kb T-DNA based binary vector which is called pBC-yellow was used in this experiment. This vector contains the RD29a promoter driving expression of the gene for ZS-Yellow, which confers yellow fluorescence to transformed seed. The rice tolerance genes were cloned as described in Example 1, and constructed in the Gateway vector. Then using the INVITROGEN™ GATEWAY® technology, an LR Recombination Reaction was performed on the entry clone containing the directionally cloned PCR product and the pBC-yellow vector, and the over-expression vectors were obtained.

T₂ seeds were used for lab drought assay. *Arabidopsis* drought screening is a soil-based water withdrawal assay performed in a growth chamber with conditions of light intensity 145 μMol, temperature 22° C. day/20° C. night and humidity ~60%. The transgenic seeds were sorted by COPAS™ (Complex Object Parametric Analyzer and Sorter, a seed sorter, Union Biometrica), and were stratified by putting in 0.1% agarose solution, and placing at 4° C. for 3 days. Wild-type *Arabidopsis* were used as control and stratified as above. 36 plants each for over-expression transgenic *Arabidopsis* and wild-type were planted equidistantly and alternatively to each other in a zig-zag fashion. The soil composition was 3 parts peat moss, 2 parts vermiculite and 1 part perlite. Apart from these, fertilizers and fungicides were added to the soil in the following concentrations: NPK (Nitrogen, Phosphorus, Potassium)—1 gm/kg soil, Micronutrients—0.5 gm/kg soil, Fungicide—0.5 gm/kg soil. Plants were thinned to 9 plants per pot (72 plants per flat), and were well watered for the first 12 days, then saturated with 1 L of deionized water for 30 min with excess water drained off completely. The plants were imaged between days 28 and 36 after germination using an imaging device and data were analyzed. The flats were rotated each day from the second day after sowing till the last day of imaging. The files generated in the imaging device were converted into XLS files and put in a Stan's format and sent to ESL for generating Stan's score for the experimental lines. Rate of decay or wilting under drought conditions is used as tested parameter. The cut-off Score=1.5.

---

What is claimed is:

1. A method of increasing drought tolerance in a plant, the method comprising: (a) introducing into a plant cell, plant, or plant part a construct comprising a polynucleotide operably linked to at least one heterologous regulatory sequence, wherein the polynucleotide encodes a polypeptide having an amino acid sequence of at least 95% sequence identity to SEQ ID NO: 5; and (b) selecting a plant cell, plant, or plant part comprising the construct for increased drought tolerance as compared to a control plant lacking the construct.

2. The method of claim 1, wherein said plant is selected from the group consisting of rice, maize, soybean, sunflower, sorghum, canola, wheat, alfalfa, cotton, barley, millet, sugar cane and switchgrass.

3. The method of claim 1, wherein the plant is maize or rice.

4. The plant method of claim 1, wherein the polynucleotide is expressed in the root tissue.

5. The method of claim 1, wherein the selection is for increased yield.

6. The method of claim 1, wherein the selection occurs during the grain fill stage.

* * * * *

SEQUENCE LISTING

```
<160> NUMBER OF SEQ ID NOS: 42

<210> SEQ ID NO 1
<211> LENGTH: 10952
<212> TYPE: DNA
<213> ORGANISM: Artificial Sequence
<220> FEATURE:
<223> OTHER INFORMATION: The nucleotide sequence of vector DP0005

<400> SEQUENCE: 1
gaattctcta gtcccgatct agtaacatag atgacaccgc gcgcgataat ttatcctagt      60
ttgcgcgcta tattttgttt tctatcgcgt attaaatgta taattgcggg actctaatca     120
taaaaaccca tctcataaat aacgtcatgc attacatgtt aattattaca tgcttaacgt     180
aattcaacag aaattatatg ataatcatcg caagaccggc aacaggattc aatcttaaga     240
aacgcggccg cttcagttgt ggcccagctt ggaggtcgac tcgcgaggat cctctagtcc     300
cgatctagta acatagatga caccgcgcgc gataatttat cctagtttgc gcgctatatt     360
ttgttttcta tcgcgtatta aatgtataat tgcgggactc taatcataaa aacccatctc     420
ataaataacg tcatgcatta catgttaatt attacatgct taacgtaatt caacagaaat     480
tatatgataa tcatcgcaag accggcaaca ggattcaatc ttaagaaacg gccgcttc     540 agttgtggcc cagcttggag gggcggcgt cgcagtagcg gcccacggcg gcctcgtact     600
gcttgtagca cttgcccttc tccacctcct ccaggatctc gatgcggtgg tcctcgaagt     660
ggaagccggg catcttcagg gcggaggcgg gcttcttgga gcggtaggtg gtgtgcaggt     720
ggcaggtcag gtggcgaccg ccggggcact ccagggccat cagggactgg ccgcgcagca     780
cgccgtccac ctcgtacacg atctcggtgg agggctccca gcggccggcc ttgttctgca     840
tcacggggcc gtcggcgggg aagttgttgc ccaggatctt caccttgtac accaggcagt     900
cgccgtccag ggaggtgtcc tggtgggcgg tcaggaagcc gccgtcctcg taggtggtgg     960
tgcgctccca ggtgaagccc tcggggaggg actgcttgaa gtagtcgggg atgccggaca    1020
```

```
cgtacttgat gaaggccttg gagccgtaca tgcaggaggt ggacaggatg tggaaggcga    1080
agggcagggg gccgccctcg atcacctcga tcttcatctc ctgggtgccc tccagggggt    1140
tgccctcgcc cttgccggtg cacttgaagt agtggccgtt cacggtgccc tcgatggtgg    1200
tcctgaaggg catggtcttc ttcagcaaag aggccatggt ggcgaccggt accagatctc    1260
tgcagagaga tagatttgta gagagagact ggtgatttca gcgtgtcctc tccaaatgaa    1320
atgaacttcc ttatatagag gaagggtctt gcgaaggata gtgggattgt gcgtcatccc    1380
ttacgtcagt ggagatatca catcaatcca cttgctttga agacgtggtt ggaacgtctt    1440 cttttccac gatgctcctc gtgggtgggg gtccatcttt gggaccactg tcggcagagg    1500
catcttgaac gatagccttt cctttatcgc aatgatggca tttgtaggtg ccaccttcct    1560
tttctactgt cctttgatg aagtgacaga tagctgggca atggaatccg aggaggtttc    1620
ccgatattac cctttgttga aaagtctcaa tagcccttg gtcttctgag actgtatctt    1680
tgatattctt ggagtagacg agagtgtcgt gctccaccat gttcacatca atccacttgc    1740
tttgaagacg tggttggaac gtcttctttt tccacgatgc tcctcgtggg tggggtcca    1800 tctttgggac cactgtcggc agaggcatct tgaacgatag cctttccttt atcgcaatga    1860
tggcatttgt aggtgccacc ttcctttct actgtccttt tgatgaagtg acagatagct    1920
gggcaatgga atccgaggag gtttcccgat attacccttt gttgaaaagt ctcaatagcc    1980
ctttggtctt ctgagactgt atctttgata ttcttggagt agacgagagt gtcgtgctcc    2040
accatgttgc caagctgctc taagcttggc actggccgtc gttttacaac gtcgtgactg    2100
ggaaaaccct ggcgttaccc aacttaatcg ccttgcagca catcccctt tcgccagctg    2160 gcgtaatagc gaagaggccc gcaccgatcg cccttcccaa cagttgcgca gcctgaatgg    2220
cgaatgctag agcagcttga gcttggatca gattgtcgtt actatcagtg tttgacagga    2280
tatattggcg ggtaaaccta agagaaaaga gcgtttatta gaataacgga tatttaaaag    2340
ggcgtgaaaa ggtttatccg ttcgtccatt tgtatgtgca tgccaaccac agggttcccc    2400
tcgggatcaa agtactttga tccaaccct ccgctgctat agtgcagtcg gcttctgacg    2460
ttcagtgcag ccgtcttctg aaaacgacat gtcgcacaag tcctaagtta cgcgacaggc    2520
tgccgccctg ccctttcct ggcgttttct tgtcgcgtgt tttagtcgca taaagtagaa    2580
tacttgcgac tagaaccgga gacattacgc catgaacaag agcgccgccg ctggcctgct    2640
gggctatgcc cgcgtcagca ccgacgacca ggacttgacc aaccaacggg ccgaactgca    2700
cgcggccggc tgcaccaagc tgttttccga aagatcacc ggcaccaggc gcgaccgccc    2760
ggagctggcc aggatgcttg accacctacg ccctggcgac gttgtgacag tgaccaggct    2820
agaccgcctg gcccgcagca cccgcgacct actggacatt gccgagcgca tccaggaggc    2880
cggcgcgggc ctgcgtagcc tggcagagcc gtgggccgac accaccacgc cggccggccg    2940
catggtgttg accgtgttcg ccggcattgc cgagttcgag cgttccctaa tcatcgaccg    3000
cacccggagc gggcgcgagg ccgccaaggc ccgaggcgtg aagtttggcc cccgccctac    3060
cctcaccccg gcacagatcg cgcacgcccg cgagctgatc gaccaggaag gccgcaccgt    3120
gaaagaggcg gctgcactgc ttggcgtgca tcgctcgacc ctgtaccgcg cacttgagcg    3180
cagcgaggaa gtgacgccca ccgaggccag gcggcgcggt gccttccgtg aggacgcatt    3240
gaccgaggcc gacgccctgg cggccgccga gaatgaacgc caagaggaac aagcatgaaa    3300
ccgcaccagg acgccaggat cgaaccgttt ttcattaccg aagagatcga ggcggagatg    3360
```

```
atcgcggccg ggtacgtgtt cgagccgccc gcgcacgtct caaccgtgcg gctgcatgaa      3420
atcctggccg gtttgtctga tgccaagctg gcggcctggc cggccagctt ggccgctgaa      3480
gaaaccgagc gccgccgtct aaaaaggtga tgtgtatttg agtaaaacag cttgcgtcat      3540
gcggtcgctg cgtatatgat gcgatgagta aataaacaaa tacgcaaggg gaacgcatga      3600
aggttatcgc tgtacttaac cagaaaggcg ggtcaggcaa gacgaccatc gcaacccatc      3660
tagcccgcgc cctgcaactc gccggggccg atgttctgtt agtcgattcc gatccccagg      3720
gcagtgcccg cgattgggcg gccgtgcggg aagatcaacc gctaaccgtt gtcggcatcg      3780
accgcccgac gattgaccgc gacgtgaagg ccatcggccg gcgcgacttc gtagtgatcg      3840
acggagcgcc ccaggcggcg gacttggctg tgtccgcgat caaggcagcc gacttcgtgc      3900
tgattccggt gcagccaagc ccttacgaca tatgggccac cgccgacctg gtggagctgg      3960
ttaagcagcg cattgaggtc acggatggaa ggctacaagc ggcctttgtc gtgtcgcggg      4020
cgatcaaagg cacgcgcatc ggcggtgagg ttgccgaggc gctggccggg tacgagctgc      4080
ccattcttga gtcccgtatc acgcagcgcg tgagctaccc aggcactgcc gccgccggca      4140
caaccgttct tgaatcagaa cccgagggcg acgctgcccg cgaggtccag gcgctggccg      4200
ctgaaattaa atcaaaactc atttgagtta atgaggtaaa gagaaaatga gcaaaagcac      4260
aaacacgcta agtgccggcc gtccgagcgc acgcagcagc aaggctgcaa cgttggccag      4320
cctggcagac acgccagcca tgaagcgggt caactttcag ttgccggcgg aggatcacac      4380
caagctgaag atgtacgcgg tacgccaagg caagaccatt accgagctgc tatctgaata      4440
catcgcgcag ctaccagagt aaatgagcaa atgaataaat gagtagatga ttttagcgg       4500 ctaaaggagg cggcatggaa aatcaagaac aaccaggcac cgacgccgtg gaatgcccca      4560
tgtgtggagg aacgggcggt tggccaggcg taagcggctg ggttgtctgc cggccctgca      4620
atggcactgg aaccccaag cccgaggaat cggcgtgacg gtcgcaaacc atccggcccg       4680
gtacaaatcg cgcggcgct gggtgatgac ctggtggaga agttgaaggc cgcgcaggcc       4740
gcccagcggc aacgcatcga ggcagaagca cgccccggtg aatcgtggca agcggccgct      4800
gatcgaatcc gcaaagaatc ccggcaaccg ccggcagccg gtgcgccgtc gattaggaag      4860
ccgcccaagg gcgacgagca accagatttt ttcgttccga tgctctatga cgtgggcacc      4920
cgcgatagtc gcagcatcat ggacgtggcc gttttccgtc tgtcgaagcg tgaccgacga      4980
gctggcgagg tgatccgcta cgagcttcca gacgggcacg tagaggtttc cgcagggccg      5040
gccggcatgg ccagtgtgtg ggattacgac ctggtactga tggcggtttc ccatctaacc      5100
gaatccatga accgataccg ggaagggaag ggagacaagc ccggccgcgt gttccgtcca      5160
cacgttgcgg acgtactcaa gttctgccgg cgagccgatg gcggaaagca gaaagacgac      5220
ctggtagaaa cctgcattcg gttaaacacc acgcacgttg ccatgcagcg tacgaagaag      5280
gccaagaacg gccgcctggt gacggtatcc gagggtgaag ccttgattag ccgctacaag      5340
atcgtaaaga gcgaaaccgg gcggccggag tacatcgaga tcgagctagc tgattggatg      5400
taccgcgaga tcacagaagg caagaacccg gacgtgctga cggttcaccc cgattacttt      5460
ttgatcgatc ccggcatcgg ccgttttctc taccgcctgg cacgccgcgc cgcaggcaag      5520
gcagaagcca gatggttgtt caagacgatc tacgaacgca gtggcagcgc cggagagttc      5580
aagaagttct gtttcaccgt gcgcaagctg atcgggtcaa atgacctgcc ggagtacgat      5640
ttgaaggagg aggcggggca ggctggcccg atcctagtca tgcgctaccg caacctgatc      5700
gagggcgaag catccgccgg ttcctaatgt acggagcaga tgctagggca aattgcccta      5760
```

```
gcaggggaaa aaggtcgaaa aggtctcttt cctgtggata gcacgtacat tgggaacccca    5820 aagccgtaca ttgggaaccg gaacccgtac attgggaacc caaagccgta cattgggaac    5880
cggtcacaca tgtaagtgac tgatataaaa gagaaaaaag gcgattttc cgcctaaaac     5940 tctttaaaac ttattaaaac tcttaaaacc cgcctggcct gtgcataact gtctggccag    6000
cgcacagccg aagagctgca aaaagcgcct acccttcggt cgctgcgctc cctacgcccc    6060
gccgcttcgc gtcggcctat cgcggccgct ggccgctcaa aaatggctgg cctacggcca    6120
ggcaatctac cagggcgcgg acaagccgcg ccgtcgccac tcgaccgccg cgcccacat    6180 caaggcaccc tgcctcgcgc gtttcggtga tgacggtgaa aacctctgac acatgcagct    6240
cccggagacg gtcacagctt gtctgtaagc ggatgccggg agcagacaag cccgtcaggg    6300
cgcgtcagcg ggtgttggcg ggtgtcgggg cgcagccatg acccagtcac gtagcgatag    6360
cggagtgtat actggcttaa ctatgcggca tcagagcaga ttgtactgag agtgcaccat    6420
atgcggtgtg aaataccgca cagatgcgta aggagaaaat accgcatcag gcgctcttcc    6480
gcttcctcgc tcactgactc gctgcgctcg gtcgttcggc tgcggcgagc ggtatcagct    6540
cactcaaagg cggtaatacg gttatccaca gaatcagggg ataacgcagg aaagaacatg    6600
tgagcaaaag gccagcaaaa ggccaggaac cgtaaaaagg ccgcgttgct ggcgtttttc    6660
cataggctcc gccccctga cgagcatcac aaaaatcgac gctcaagtca gaggtggcga    6720
aacccgacag gactataaag ataccaggcg tttcccctg gaagctccct cgtgcgctct    6780
cctgttccga ccctgccgct taccggatac ctgtccgcct ttctcccttc gggaagcgtg    6840
gcgctttctc atagctcacg ctgtaggtat ctcagttcgg tgtaggtcgt tcgctccaag    6900
ctgggctgtg tgcacgaacc ccccgttcag cccgaccgct gcgccttatc cggtaactat    6960
cgtcttgagt ccaacccggt aagacacgac ttatcgccac tggcagcagc cactggtaac    7020
aggattagca gagcgaggta tgtaggcggt gctacagagt tcttgaagtg gtggcctaac    7080
tacggctaca ctagaaggac agtatttggt atctgcgctc tgctgaagcc agttaccttc    7140
ggaaaaagag ttggtagctc ttgatccggc aaacaaacca ccgctggtag cggtggtttt    7200
tttgtttgca agcagcagat tacgcgcaga aaaaaaggat ctcaagaaga tcctttgatc    7260
ttttctacgg ggtctgacgc tcagtggaac gaaaactcac gttaagggat tttggtcatg    7320
cattctaggt actaaaacaa ttcatccagt aaaatataat atttatttt ctcccaatca     7380 ggcttgatcc ccagtaagtc aaaaatagc tcgacatact gttcttcccc gatatcctcc     7440
ctgatcgacc ggacgcagaa ggcaatgtca taccacttgt ccgccctgcc gcttctccca    7500
agatcaataa agccacttac tttgccatct ttcacaaaga tgttgctgtc tcccaggtcg    7560
ccgtgggaaa agacaagttc ctcttcgggc ttttccgtct ttaaaaaatc atacagctcg    7620
cgcggatctt taaatggagt gtcttcttcc cagttttcgc aatccacatc ggccagatcg    7680
ttattcagta agtaatccaa ttcggctaag cggctgtcta agctattcgt ataggggacaa   7740 tccgatatgt cgatggagtg aaagagcctg atgcactccg catacagctc gataatcttt    7800
tcagggcttt gttcatcttc atactcttcc gagcaaagga cgccatcggc ctcactcatg    7860
agcagattgc tccagccatc atgccgttca agtgcagga cctttggaac aggcagctttt    7920 ccttccagcc atagcatcat gtcctttttcc cgttccacat cataggtggt cctttatac    7980 cggctgtccg tcattttaa atataggttt tcatttctc ccaccagctt atataccta      8040 gcaggagaca ttccttccgt atcttttacg cagcggtatt tttcgatcag ttttttcaat    8100
```

```
tccggtgata ttctcatttt agccatttat tatttccttc ctcttttcta cagtatttaa    8160
agatacccca agaagctaat tataacaaga cgaactccaa ttcactgttc cttgcattct    8220
aaaaccttaa ataccagaaa acagcttttt caaagttgtt ttcaaagttg gcgtataaca    8280
tagtatcgac ggagccgatt ttgaaaccgc ggtgatcaca ggcagcaacg ctctgtcatc    8340
gttacaatca acatgctacc ctccgcgaga tcatccgtgt ttcaaacccg gcagcttagt    8400
tgccgttctt ccgaatagca tcggtaacat gagcaaagtc tgccgcctta caacggctct    8460
cccgctgacg ccgtcccgga ctgatgggct gcctgtatcg agtggtgatt tgtgccgag    8520
ctgccggtcg gggagctgtt ggctggctgg tggcaggata tattgtggtg taaacaaatt    8580
gacgcttaga caacttaata acacattgcg gacgttttta atgtactgaa ttaacgccga    8640
attaattcgg gggatctgga ttttagtact ggattttggt tttaggaatt agaaatttta    8700
ttgatagaag tattttacaa atacaaatac atactaaggg tttcttatat gctcaacaca    8760
tgagcgaaac cctataggaa ccctaattcc cttatctggg aactactcac acattattat    8820
ggagaaactc gagcttgtcg atcgacagat ccggtcggca tctactctat ttctttgccc    8880
tcggacgagt gctggggcgt cggttttccac tatcggcgag tacttctaca cagccatcgg    8940
tccagacggc cgcgcttctg cgggcgattt gtgtacgccc gacagtcccg gctccggatc    9000
ggacgattgc gtcgcatcga ccctgcgccc aagctgcatc atcgaaattg ccgtcaacca    9060
agctctgata gagttggtca agaccaatgc ggagcatata cgcccggagt cgtggcgatc    9120
ctgcaagctc cggatgcctc cgctcgaagt agcgcgtctg ctgctccata caagccaacc    9180
acggcctcca gaagaagatg ttggcgacct cgtattggga atccccgaac atcgcctcgc    9240
tccagtcaat gaccgctgtt atgcggccat tgtccgtcag gacattgttg gagccgaaat    9300
ccgcgtgcac gaggtgccgg acttcggggc agtcctcggc ccaaagcatc agctcatcga    9360
gagcctgcgc gacggacgca ctgacggtgt cgtccatcac agtttgccag tgatacacat    9420
ggggatcagc aatcgcgcat atgaaatcac gccatgtagt gtattgaccg attccttgcg    9480
gtccgaatgg gccgaacccg ctcgtctggc taagatcggc cgcagcgatc gcatccatag    9540
cctccgcgac cggttgtaga acagcgggca gttcggtttc aggcaggtct tgcaacgtga    9600
caccctgtgc acggcgggag atgcaatagg tcaggctctc gctaaactcc ccaatgtcaa    9660
gcacttccgg aatcgggagc gcggccgatg caaagtgccg ataaacataa cgatctttgt    9720
agaaaccatc ggcgcagcta tttacccgca ggacatatcc acgccctcct acatcgaagc    9780
tgaaagcacg agattcttcg ccctccgaga gctgcatcag gtcggagacg ctgtcgaact    9840
tttcgatcag aaacttctcg acagacgtcg cggtgagttc aggcttttc atatctcatt    9900
gccccccggg atctgcgaaa gctcgagaga gatagatttg tagagagaga ctggtgattt    9960
cagcgtgtcc tctccaaatg aaatgaactt ccttatatag aggaaggtct tgcgaaggat    10020
agtgggattg tgcgtcatcc cttacgtcag tggagatatc acatcaatcc acttgctttg    10080
aagacgtggt tggaacgtct tctttttcca cgatgctcct cgtgggtggg ggtccatctt    10140
tgggaccact gtcggcagag gcatcttgaa cgatagcctt tcctttatcg caatgatggc    10200
atttgtaggt gccaccttcc ttttctactg tcctttgat gaagtgacag atagctgggc    10260
aatggaatcc gaggaggttt cccgatatta ccctttgttg aaaagtctca atagcccttt    10320
ggtcttctga gactgtatct ttgatattct tggagtagac gagagtgtcg tgctccacca    10380
tgttatcaca tcaatccact tgctttgaag acgtggttgg aacgtcttct ttttccacga    10440
tgctcctcgt gggtgggggt ccatctttgg gaccactgtc ggcagaggca tcttgaacga    10500
```

```
tagcctttcc tttatcgcaa tgatggcatt tgtaggtgcc accttccttt tctactgtcc    10560
ttttgatgaa gtgacagata gctgggcaat ggaatccgag gaggtttccc gatattaccc    10620
tttgttgaaa agtctcaata gcccttttggt cttctgagac tgtatctttg atattcttgg   10680
agtagacgag agtgtcgtgc tccaccatgt tggcaagctg ctctagccaa tacgcaaacc    10740
gcctctcccc gcgcgttggc cgattcatta atgcagctgg cacgacaggt ttcccgactg    10800
gaaagcgggc agtgagcgca acgcaattaa tgtgagttag ctcactcatt aggcacccca    10860
ggctttacac tttatgcttc cggctcgtat gttgtgtgga attgtgagcg gataacaatt    10920
tcacacagga aacagctatg accatgatta cg                                  10952
```

<210> SEQ ID NO 2
<211> LENGTH: 1921
<212> TYPE: DNA
<213> ORGANISM: Artificial Sequence
<220> FEATURE:
<223> OTHER INFORMATION: The nucleotide sequence of DsRed expression cassette

<400> SEQUENCE: 2

```
cgaagctggc cgctctagaa ctagtggatc tcgatgtgta gtctacgaga agggttaacc      60
gtctcttcgt gagaataacc gtggcctaaa aataagccga tgaggataaa taaaatgtgg     120
tggtacagta cttcaagagg tttactcatc aagaggatgc ttttccgatg agctctagta    180
gtacatcgga cctcacatac ctccattgtg gtgaaatatt tgtgctcat ttagtgatgg     240 gtaaattttg tttatgtcac tctaggtttt gacatttcag ttttgccact cttaggtttt    300
gacaaataat ttccattccg cggcaaaagc aaaacaattt tattttactt ttaccactct    360
tagctttcac aatgtatcac aaatgccact ctagaaattc tgtttatgcc acagaatgtg    420
aaaaaaaaca ctcacttatt tgaagccaag gtgttcatgg catggaaatg tgacataaag    480
taacgttcgt gtataagaaa aaattgtact cctcgtaaca agagacggaa acatcatgag    540
acaatcgcgt ttggaaggct ttgcatcacc tttggatgat gcgcatgaat ggagtcgtct    600
gcttgctagc cttcgcctac cgcccactga gtccgggcgg caactaccat cggcgaacga    660
cccagctgac ctctaccgac cggacttgaa tgcgctacct tcgtcagcga cgatggccgc    720
gtacgctggc gacgtgcccc gcatgcatg cggcacatg gcgagctcag accgtgcgtg     780
gctggctaca aatacgtacc ccgtgagtgc cctagctaga aacttacacc tgcaactgcg    840
agagcgagcg tgtgagtgta gccgagtaga tcctcgccac catggcctcc tccgagaacg    900
tcatcaccga gttcatgcgc ttcaaggtgc gcatggaggg caccgtgaac ggccacgagt    960
tcgagatcga gggcgagggc gagggccgcc cctacgaggg ccacaacacc gtgaagctga   1020
aggtgaccaa gggcggcccc ctgcccttcg cctgggacat cctgtccccc cagttccagt   1080
acggctccaa ggtgtacgtg aagcaccccg ccgacatccc cgactacaag aagctgtcct   1140
tccccgaggg cttcaagtgg gagcgcgtga tgaacttcga ggacggcggc gtggcgaccg   1200
tgacccagga ctcctcccctg caggacggct gcttcatcta caaggtgaag ttcatcggcg   1260
tgaacttccc ctccgacggc cccgtgatgc agaagaagac catgggctgg gaggcctcca   1320
ccgagcgcct gtaccccgc gacggcgtgc tgaagggcga gacccacaag gccctgaagc    1380
tgaaggacgg cggccactac ctggtggagt caagtccat ctacatggcc aagaagcccg    1440
tgcagctgcc cggctactac tacgtggacg ccaagctgga catcacctcc cacaacgagg   1500
actacaccat cgtggagcag tacgagcgca ccgagggccg ccaccacctg ttcctgtagc   1560
```

| | | | | |
|---|---|---|---|---|
| ggcccatgga | tattcgaacg | cgtaggtacc | acatggttaa | cctagacttg tccatcttct | 1620 |
| ggattggcca | acttaattaa | tgtatgaaat | aaaaggatgc | acacatagtg acatgctaat | 1680 |
| cactataatg | tgggcatcaa | agttgtgtgt | tatgtgtaat | tactagttat ctgaataaaa | 1740 |
| gagaaagaga | tcatccatat | ttcttatcct | aaatgaatgt | cacgtgtctt tataattctt | 1800 |
| tgatgaacca | gatgcatttc | attaaccaaa | tccatataca | tataaatatt aatcatatat | 1860 |
| aattaatatc | aattgggtta | gcaaaacaaa | tctagtctag | gtgtgttttg cgaatgcggc | 1920 |
| c | | | | | 1921 |

<210> SEQ ID NO 3
<211> LENGTH: 727
<212> TYPE: DNA
<213> ORGANISM: Oryza sativa

<400> SEQUENCE: 3

| | | | | | |
|---|---|---|---|---|---|
| aaatggttaa | gctaatcagc | gccttcggga | gcccattcgg | gcaccgcgcc gaggcggcgc | 60 |
| tccggctgaa | aggcgtgcag | tacgagctcc | tcctggaaga | cctccgcagc aagagcgacc | 120 |
| tgctgctcgc | ccacaacccc | gtccacaagc | tcgtccccgt | cctcctccac tccgacggcc | 180 |
| gctccgtcgc | cgagtccctc | gtcgtcgtcc | agtacgtcga | cgacgccttc catggcccgc | 240 |
| ccctcctccc | cgccgaccca | tacgctcgtg | cccaggcccg | tttctgggcc caattcatcg | 300 |
| atgataagtt | ctcgaggccg | ttctggctgt | cgttctggat | ggaggacggg gagaagaagg | 360 |
| aggcgttcgt | gagggaagcg | aaggagaatc | tgcggccgct | ggaggcgcag ctcgacggcg | 420 |
| gcaacaagag | gttcttcggc | ggcgacgcca | ttggcctcgt | ggacatcgcc gccagtgggc | 480 |
| tggctcactg | ggtcggggtg | ttcgaggagg | tcaccggcgt | gagcttggtg agcgagcggg | 540 |
| agttccccgc | gctgtgccgg | tggtcgcagc | gctacgtcaa | cgatggagcc gtgaggcagt | 600 |
| gcttgccgag | cagagatgaa | ctcgtcgcct | tgttcactgc | aaacaaagag gcgtatacac | 660 |
| tgctggccaa | ggcaaagttg | cagaaataat | tttattactc | gtgaatttcg atgctggaat | 720 |
| atgcgta | | | | | 727 |

<210> SEQ ID NO 4
<211> LENGTH: 687
<212> TYPE: DNA
<213> ORGANISM: Oryza sativa

<400> SEQUENCE: 4

| | | | | | |
|---|---|---|---|---|---|
| atggttaagc | taatcagcgc | cttcgggagc | ccattcgggc | accgcgccga ggcggcgctc | 60 |
| cggctgaaag | gcgtgcagta | cgagctcctc | ctggaagacc | tccgcagcaa gagcgacctg | 120 |
| ctgctcgccc | acaaccccgt | ccacaagctc | gtccccgtcc | tcctccactc cgacggccgc | 180 |
| tccgtcgccg | agtccctcgt | cgtcgtccag | tacgtcgacg | acgccttcca tggcccgccc | 240 |
| ctcctccccg | ccgacccata | cgctcgtgcc | caggcccgtt | tctgggccca attcatcgat | 300 |
| gataagttct | cgaggccgtt | ctggctgtcg | ttctggatgg | aggacgggga gaagaaggag | 360 |
| gcgttcgtga | gggaagcgaa | ggagaatctg | cggccgctgg | aggcgcagct cgacggcggc | 420 |
| aacaagaggt | tcttcggcgg | cgacgccatt | ggcctcgtgg | acatcgccgc cagtgggctg | 480 |
| gctcactggg | tcggggtgtt | cgaggaggtc | accggcgtga | gcttggtgag cgagcgggag | 540 |
| ttccccgcgc | tgtgccggtg | gtcgcagcgc | tacgtcaacg | atggagccgt gaggcagtgc | 600 |
| ttgccgagca | gagatgaact | cgtcgccttg | ttcactgcaa | acaaagaggc gtatacactg | 660 | ctggccaagg caaagttgca gaaataa 687

<210> SEQ ID NO 5
<211> LENGTH: 228
<212> TYPE: PRT
<213> ORGANISM: Oryza sativa

<400> SEQUENCE: 5

```
Met Val Lys Leu Ile Ser Ala Phe Gly Ser Pro Phe Gly His Arg Ala
1               5                   10                  15
Glu Ala Ala Leu Arg Leu Lys Gly Val Gln Tyr Glu Leu Leu Leu Glu
            20                  25                  30
Asp Leu Arg Ser Lys Ser Asp Leu Leu Ala His Asn Pro Val His
        35                  40                  45
Lys Leu Val Pro Val Leu Leu His Ser Asp Gly Arg Ser Val Ala Glu
    50                  55                  60
Ser Leu Val Val Gln Tyr Val Asp Asp Ala Phe His Gly Pro Pro
65                  70                  75                  80
Leu Leu Pro Ala Asp Pro Tyr Ala Arg Ala Gln Ala Arg Phe Trp Ala
                85                  90                  95
Gln Phe Ile Asp Asp Lys Phe Ser Arg Pro Trp Leu Ser Phe Trp
            100                 105                 110
Met Glu Asp Gly Glu Lys Lys Glu Ala Phe Val Arg Glu Ala Lys Glu
        115                 120                 125
Asn Leu Arg Pro Leu Glu Ala Gln Leu Asp Gly Gly Asn Lys Arg Phe
    130                 135                 140
Phe Gly Gly Asp Ala Ile Gly Leu Val Asp Ile Ala Ala Ser Gly Leu
145                 150                 155                 160
Ala His Trp Val Gly Val Phe Glu Glu Val Thr Gly Val Ser Leu Val
                165                 170                 175
Ser Glu Arg Glu Phe Pro Ala Leu Cys Arg Trp Ser Gln Arg Tyr Val
            180                 185                 190
Asn Asp Gly Ala Val Arg Gln Cys Leu Pro Ser Arg Asp Glu Leu Val
        195                 200                 205
Ala Leu Phe Thr Ala Asn Lys Glu Ala Tyr Thr Leu Leu Ala Lys Ala
    210                 215                 220
Lys Leu Gln Lys
225
```

<210> SEQ ID NO 6
<211> LENGTH: 760
<212> TYPE: DNA
<213> ORGANISM: Oryza sativa

<400> SEQUENCE: 6
ggagaagaga atcgcggaga tagcatgagc agcggcggcg agctcgcgga gcaggagccc    60
aaggtgcacc tcgtcgcgtc ggcgccgggg cccgggccca gcccgcacgt cgtcgcgctc   120
cacgccgcct tcgaggacga cgccgcggtg cacctcgtgg tcgacctctg cgcgggcggg   180
gacctcctct ccctcgtctc ctcccgcggc cgcctcccgg agcacgaggc cgcggacctc   240
gtggcgcaac tggcctccgc gctcgcgtcc tgccaccgcc gcggggtagc gcaccgcgac   300
gtgaagcccg acaacctcct gttcgacggc ggcggcgtgc tcaagctcgg cgacttcggg   360
tcggcggggt ggttcgggga cgggaggccg atgacgggc tggtcgggac gccctactac   420
gtggcgccgg aggtggtggc cgggagggag tacggcgaga aggtggacgt gtggagcgcc   480

```
ggggtggtgc tctacatgat gctctccggg accctgccct tctacggcgc caccgccgcg      540
gaggtcttcc agtgcgtgct ccgcggcaac ctccgcttcc cgccgcgcgc gttcgcctcc      600
gtctcgccgg aggccaagga cctgatgcgc cgcatgctct gcaaggacgt ctccagaagg      660
ttctccgccg accaagtcct gaggcatcct tggatcgtga ccgtgggggg agccgcggtg      720
atgggctagt tcgttcgatc gaggatgatg atgaactcca                            760
```

<210> SEQ ID NO 7
<211> LENGTH: 705
<212> TYPE: DNA
<213> ORGANISM: Oryza sativa

<400> SEQUENCE: 7

```
atgagcagcg gcggcgagct cgcggagcag gagcccaagg tgcacctcgt cgcgtcggcg       60
ccggggcccg gggccagccc gcacgtcgtc gcgctccacg ccgccttcga ggacgacgcc      120
gcggtgcacc tcgtggtcga cctctgcgcg ggcggggacc tcctctccct cgtctcctcc      180
cgcggccgcc tcccggagca cgaggccgcg gacctcgtgg cgcaactggc ctccgcgctc      240
gcgtcctgcc accgccgcgg ggtagcgcac cgcgacgtga agcccgacaa cctcctgttc      300
gacggcggcg gcgtgctcaa gctcggcgac ttcgggtcgg cggggtggtt cggggacggg      360
aggccgatga cggggctggt cgggacgccc tactacgtgg cgccggaggt ggtggccggg      420
agggagtacg gcgagaaggt ggacgtgtgg agcgccgggg tggtgctcta catgatgctc      480
tccgggaccc tgcccttcta cggcgccacc gccgcggagg tcttccagtg cgtgctccgc      540
ggcaacctcc gcttcccgcc gcgcgcgttc gcctccgtct cgccggaggc caaggacctg      600
atgcgccgca tgctctgcaa ggacgtctcc agaaggttct ccgccgacca agtcctgagg      660
catccttgga tcgtgagccg tggggagcc gcggtgatgg gctag                       705
```

<210> SEQ ID NO 8
<211> LENGTH: 234
<212> TYPE: PRT
<213> ORGANISM: Oryza sativa

<400> SEQUENCE: 8

```
Met Ser Ser Gly Gly Glu Leu Ala Glu Gln Glu Pro Lys Val His Leu
1               5                   10                  15

Val Ala Ser Ala Pro Gly Pro Gly Ala Ser Pro His Val Val Ala Leu
            20                  25                  30

His Ala Ala Phe Glu Asp Asp Ala Ala Val His Leu Val Val Asp Leu
        35                  40                  45

Cys Ala Gly Gly Asp Leu Leu Ser Leu Val Ser Ser Arg Gly Arg Leu
    50                  55                  60

Pro Glu His Glu Ala Ala Asp Leu Val Ala Gln Leu Ala Ser Ala Leu
65                  70                  75                  80

Ala Ser Cys His Arg Arg Gly Val Ala His Arg Asp Val Lys Pro Asp
                85                  90                  95

Asn Leu Leu Phe Asp Gly Gly Val Leu Lys Leu Gly Asp Phe Gly
            100                 105                 110

Ser Ala Gly Trp Phe Gly Asp Gly Arg Pro Met Thr Gly Leu Val Gly
        115                 120                 125

Thr Pro Tyr Tyr Val Ala Pro Glu Val Val Ala Gly Arg Glu Tyr Gly
    130                 135                 140

Glu Lys Val Asp Val Trp Ser Ala Gly Val Val Leu Tyr Met Met Leu
145                 150                 155                 160
```

Ser Gly Thr Leu Pro Phe Tyr Gly Ala Thr Ala Ala Glu Val Phe Gln
            165                 170                 175

Cys Val Leu Arg Gly Asn Leu Arg Phe Pro Pro Arg Ala Phe Ala Ser
            180                 185                 190

Val Ser Pro Glu Ala Lys Asp Leu Met Arg Met Leu Cys Lys Asp
        195                 200                 205

Val Ser Arg Arg Phe Ser Ala Asp Gln Val Leu Arg His Pro Trp Ile
    210                 215                 220

Val Ser Arg Gly Gly Ala Ala Val Met Gly
225                 230

<210> SEQ ID NO 9
<211> LENGTH: 576
<212> TYPE: DNA
<213> ORGANISM: Oryza sativa

<400> SEQUENCE: 9
ctcgcggaac cttctcgaag cttccacacc cccaacctcg cctccaccac caaccccca       60 tggcggacca gctcaccgac gagcagatcg ccgagttcaa ggaggcgttc agcctcttcg     120
acaaggacgg cgacggttgc atcactacta aggagcttgg aaccgtgatg cggtcccttg     180
gtcagaaccc aactgaggcg gagctgcagg acatgatcaa cgaggttgat gctgatggca     240
atgggaccat tgacttccca gagttcctga acctgatggc gaagaagatg aaggataccg     300
actctgagga ggagctcaag gaggccttcc gtgtgtttga caaggaccag aacggtttca     360
tctcggctgc tgagctccgc cacgtcatga ccaaccttgg tgagaagctg accgacgagg     420
aagtcgacga gatgatccgt gaggctgacg tcgatggcga tggccagatc aactacgagg     480
agttcgttaa ggtcatgatg gccaagtgag gagggttccc attaaataag ttctgtctga     540
agtgaactaa aactgtcagg gcctacaaca aagctg                              576

<210> SEQ ID NO 10
<211> LENGTH: 450
<212> TYPE: DNA
<213> ORGANISM: Oryza sativa

<400> SEQUENCE: 10
atggcggacc agctcaccga cgagcagatc gccgagttca aggaggcgtt cagcctcttc       60
gacaaggacg gcgacggttg catcactact aaggagcttg gaaccgtgat gcggtccctt     120
ggtcagaacc caactgaggc ggagctgcag gacatgatca acgaggttga tgctgatggc     180
aatgggacca ttgacttccc agagttcctg aacctgatgg cgaagaagat gaaggatacc     240
gactctgagg aggagctcaa ggaggccttc cgtgtgtttg acaaggacca gaacggtttc     300
atctcggctg ctgagctccg ccacgtcatg accaaccttg gtgagaagct gaccgacgag     360
gaagtcgacg agatgatccg tgaggctgac gtcgatggcg atggccagat caactacgag     420
gagttcgtta aggtcatgat ggccaagtga                                     450

<210> SEQ ID NO 11
<211> LENGTH: 149
<212> TYPE: PRT
<213> ORGANISM: Oryza sativa

<400> SEQUENCE: 11

Met Ala Asp Gln Leu Thr Asp Glu Gln Ile Ala Glu Phe Lys Glu Ala
1               5                   10                  15

```
Phe Ser Leu Phe Asp Lys Asp Gly Asp Gly Cys Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asn Gly Thr Ile
    50                  55                  60

Asp Phe Pro Glu Phe Leu Asn Leu Met Ala Lys Lys Met Lys Asp Thr
65                  70                  75                  80

Asp Ser Glu Glu Glu Leu Lys Glu Ala Phe Arg Val Phe Asp Lys Asp
                85                  90                  95

Gln Asn Gly Phe Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Val Asp Gly Asp Gly Gln Ile Asn Tyr Glu Glu Phe Val Lys
    130                 135                 140

Val Met Met Ala Lys
145

<210> SEQ ID NO 12
<211> LENGTH: 1184
<212> TYPE: DNA
<213> ORGANISM: Oryza sativa

<400> SEQUENCE: 12
gcggcaaaaa cgatgtcagt ggctagacag cggccagcgg ggaggcagct ggcggcgagg      60
ctaagtggtg gcggcggccg ctgacctcgc cgatggcgga gacactacgg cgaatccgag     120
atggcggcgc catgctcctc ctcgtcctcc tcaccatcgc agcgcaggtg cagcaggagt     180
acgaggtcac ctcctcctcg tcctccttgc catcgcggcg tggcgcgggc gagggccatc     240
agcagctgcc ttgggcgcag caggagtacg aagtcacctc tgccgccact gcggggccct     300
gcgatgccta cctcgtgttc cgctcctccc caccgctcta cgcctccgcc gtctctatct     360
tcaacctcct caacgtcacc gccaccccccg gcgacgaggt cgtccgcgga ggagatggag     420
gagcaccaaa actggaagaa gaacgcgctg gtgctctatg acctcgtcat ctcccagccg     480
ctcgagtggc catcgctcac cgtccagtgg ctcccctccc actcccggtc accggactcc     540
accctctcct accgcctcat cctcggaacc cacacctccg acgagacgtg ccaaccacct     600
cctgctcgcc gacgccaccc tcccgcttcc accctgcctg gcggcggcag cctcggcggc     660
gagcggcgcc gtcccgaccc cgcttgtgtc catctcccgc tcggtgccgc acaatggcga     720
ggtcaaccac gcccgctgca tgccgcagag gccgtacacg gtggctacca agacctgtgt     780
ggatgaggtg catgtgtacc atcttggtga cggcggcgag aagagcgacg tcgatgtggt     840
gctcaggggg catgaagctg aggggtatgg gctggcgcca gttcagagta cggtgccgtt     900
ccaggtgagc atctccacca gccgatccac catcgcagtc gacgtgccga cctgtcggag     960
cacggcctcg ccgagccgcg ggttcgccgc gacattgacg aagatgacga agggagggag    1020
agagagagag atgaggaagg gagagaagag gggaaagagg gaaaggaggc tgacgtggac    1080
acctgacatg tgggtcctat gctgactcag ccgtcacgta gaataaaacc ggagttaaaa    1140
ccaccgaagg atctcgggag accggtttta tatagttaag ggac                     1184

<210> SEQ ID NO 13
<211> LENGTH: 813
<212> TYPE: DNA
```

<213> ORGANISM: Oryza sativa

<400> SEQUENCE: 13

```
atggcggaga cactacggcg aatccgagat ggcggcgcca tgctcctcct cgtcctcctc      60
accatcgcag cgcaggtgca gcaggagtac gaggtcacct cctcctcgtc ctccttgcca     120
tcgcggcgtg gcgcgggcga gggccatcag cagctgcctt gggcgcagca ggagtacgaa     180
gtcacctctg ccgccactgc ggggccctgc gatgcctacc tcgtgttccg ctcctcccca     240
ccgctctacg cctccgccgt ctctatcttc aacctcctca cgtcaccgc caccccggc       300
gacgaggtcg tccgcggagg agatggagga gcaccaaaac tggaagaaga acgcgctgcc     360
tcggcggcga gcggcgccgt cccgaccccg cttgtgtcca tctcccgctc ggtgccgcac     420
aatggcgagg tcaaccacgc ccgctgcatg ccgcagaggc cgtacacggt ggctaccaag     480
acctgtgtgg atgaggtgca tgtgtaccat cttggtgacg gcggcgagaa gagcgacgtc     540
gatgtggtgc tcaggggggca tgaagctgag gggtatgggc tggcgccagt tcagagtacg     600
gtgccgttcc aggtgagcat ctccaccagc cgatccacca tcgcagtcga cgtgccgacc     660
tgtcggagca cggcctcgcc gagccgcggg ttcgccgcga cattgacgaa gatgacgaag     720
ggagggagag agagagagat gaggaaggga gagaagaggg gaaagaggga aaggaggctg     780
acgtggacac ctgacatgtg ggtcctatgc tga                                  813
```

<210> SEQ ID NO 14
<211> LENGTH: 270
<212> TYPE: PRT
<213> ORGANISM: Oryza sativa

<400> SEQUENCE: 14

```
Met Ala Glu Thr Leu Arg Arg Ile Arg Asp Gly Gly Ala Met Leu Leu
1               5                   10                  15

Leu Val Leu Leu Thr Ile Ala Ala Gln Val Gln Gln Glu Tyr Glu Val
            20                  25                  30

Thr Ser Ser Ser Ser Ser Leu Pro Ser Arg Arg Gly Ala Gly Glu Gly
        35                  40                  45

His Gln Gln Leu Pro Trp Ala Gln Gln Glu Tyr Glu Val Thr Ser Ala
    50                  55                  60

Ala Thr Ala Gly Pro Cys Asp Ala Tyr Leu Val Phe Arg Ser Ser Pro
65                  70                  75                  80

Pro Leu Tyr Ala Ser Ala Val Ser Ile Phe Asn Leu Leu Asn Val Thr
                85                  90                  95

Ala Thr Pro Gly Asp Glu Val Val Arg Gly Gly Asp Gly Gly Ala Pro
            100                 105                 110

Lys Leu Glu Glu Arg Ala Ala Ser Ala Ala Ser Gly Ala Val Pro
        115                 120                 125

Thr Pro Leu Val Ser Ile Ser Arg Ser Val Pro His Asn Gly Glu Val
    130                 135                 140

Asn His Ala Arg Cys Met Pro Gln Arg Pro Tyr Thr Val Ala Thr Lys
145                 150                 155                 160

Thr Cys Val Asp Glu Val His Val Tyr His Leu Gly Asp Gly Gly Glu
                165                 170                 175

Lys Ser Asp Val Asp Val Val Leu Arg Gly His Glu Ala Glu Gly Tyr
            180                 185                 190

Gly Leu Ala Pro Val Gln Ser Thr Val Pro Phe Gln Val Ser Ile Ser
        195                 200                 205
```

```
Thr Ser Arg Ser Thr Ile Ala Val Asp Val Pro Thr Cys Arg Ser Thr
    210                 215                 220
Ala Ser Pro Ser Arg Gly Phe Ala Ala Thr Leu Thr Lys Met Thr Lys
225                 230                 235                 240
Gly Gly Arg Glu Arg Glu Met Arg Lys Gly Glu Lys Arg Gly Lys Arg
                245                 250                 255
Glu Arg Arg Leu Thr Trp Thr Pro Asp Met Trp Val Leu Cys
            260                 265                 270

<210> SEQ ID NO 15
<211> LENGTH: 2346
<212> TYPE: DNA
<213> ORGANISM: Oryza sativa

<400> SEQUENCE: 15
accggggccg tgacttgact gacacaatag aagcagcaaa gcttgggcat ttggtgaggc      60
actgattgaa gctcagcact aggcgaagtg cagggcatgg tgcttcccaa accagaaatg    120
ccgttctttg tcctgctcct cttcctcggc ctcggctgcc tccgcccggc ggcggcgacc    180
gacgagcggt tcgtcttcaa cgggttcacc ggcgccaacc tcagcttcga cggcatggca    240
acggtgacct cgaacgggct gctcatgctg accaacggca cgaaccagct caagggccac    300
gccttcttcc cgtcgccgct ccagttccag aggggggccca acagcacggc gatgcagtcc    360
ttctccacgg ccttcgtcat cggcatcatc ggcgcgttcg aggacctgag cagccacggc    420
atggcgttca tcatcgccaa gagcaagaac ctcacctcgg cgctgccggg cagttcatg    480
gggctcgtca actccgccaa caacggcaac gcgaccaacc acctcttcgc cgtggagttc    540
gacaccatcc tcaactcgga gttcaacgac atgagcggca accatgtcgg gatcgacgtc    600
aacggcctca actccgtcga cgccgacaac gccgggtact acgacgacgg caccggcgac    660
ttcaagaaca tgagcctggt gagccgcagg ccgatgcagg tgtgggtgga cttcgacggc    720
cagaccatgc aggtcaatgt caccatggcg ccgctggagg tggcgcggcc aaagaagccc    780
ctgctgtcca aaatcgtcaa catctcctcc gtcattgatg acaccgccta cgtcggcttc    840
tcctcggcga ccggcatcct cttctgccgc cactacgtgc tcggctggag cttcaagatg    900
aacggcgccg cgccggcgct caacatctca tccctgccct ccctgccggt cacgttcccc    960
aagccgcggt ccaagacgct tgagatcgtg ctgccgatag cctcggcggt gctcgtcttc   1020
gcggtggccg ccgccgtgtt cgtgttcatg cggcggcggc gcatgttctc ggagctcaag   1080
gaggagtggg aggtgacgtt cgggcctcac aggttctcgt acaaggacct gttccacgcc   1140
accgacgggt tcagcgacaa gcggctcctc ggcatcggcg ggttcgggcg cgtgtaccgt   1200
ggcgtgctcc cgtcgtccaa ggcggaggtc gccgtgaaga aggtggcgca cgggtcgagg   1260
caggggatga gggagttcgt ggcggaggtg gtcagcatcg gccggctccg gcaccggaac   1320
ctcgtgcagc tgctcggcta ctgccggcgc aagggcgagc tcctgctggt gtacgactac   1380
atgcccaacg gcagcctgga caagcagctg tacgaccagg gcaagatcac cctgagatgg   1440
gcgcagaggt tccgcatcat cagggggcgtc gcgtccgggc tgctctacct ccacgaggac   1500
tgggagcagg tggtggtgca cagggacatc aaggccagca acgtgctgct cgacgccgac   1560
atgaacggcc ggctcggcga cttcggcctg gcgcggctgt acgaccacgg caccgacccg   1620
cacacgacgc acgtggtggg caccatgggc tacctggcgc ggagctgggg cacaccggcg   1680
aaggcgtcca aggcgtcgga cgtgttcgcg ttcgggcct tcatgctgga ggtggcgtgc   1740
gggcggaagc ccgtggcgca ggacgcgcgc gacaaccgcg tcgtgctcgt cgactgggtg   1800
```

```
ctcgaccggt ggcgcgccgg ggcgatcacg gacacggtgg acccgcgcct gcacggcgac    1860
ttcgtcgaga gcgaggcgag cctcgtgctg cggctgggcc tgctgtgctc gcacccgctg    1920
cccggcgcac ggccggggac gaggcagctt gtgcagtacc tggaaggcga cgtgccgctg    1980
ccggagctgt cgccgacgta ccagagcttc aacatgctgg cgctcatgca ggaccagggg    2040 ttcgaccccct acgtcatgtc ctacccgatg acatccacca gcgcaggcac cttctctgac    2100
ctctctggag gtagatgatg acccgttccc atcagccgga tgtagttaat cagtacctaa    2160
ctagtatcat cctgtttttgt ttaagatcag aactttggtg ttgttatgtt tatatctatg    2220
atgtaaagtg gtgttacgag aatagctcag tgttcagata agagctgaga ataacagat     2280 ctgaaattaa acatttcggg ctttacctcc cactataaat tttctcctct gatctgattg    2340
tcgacg                                                              2346
```

<210> SEQ ID NO 16
<211> LENGTH: 2022
<212> TYPE: DNA
<213> ORGANISM: Oryza sativa
<400> SEQUENCE: 16

```
atggtgcttc ccaaaccaga aatgccgttc tttgtcctgc tcctcttcct cggcctcggc      60
tgcctccgcc cggcggcggc gaccgacgag cggttcgtct tcaacggggtt caccggcgcc    120 aacctcagct tcgacggcat ggcaacggtg acctcgaacg ggctgctcat gctgaccaac    180
ggcacgaacc agctcaaggg ccacgccttc ttcccgtcgc cgctccagtt ccagaggggg    240
cccaacagca cggcgatgca gtccttctcc acggccttcg tcatcggcat catcggcgcg    300
ttcgaggacc tgagcagcca cggcatggcg ttcatcatcg ccaagagcaa gaacctcacc    360
tcggcgctgc cggggcagtt catggggctc gtcaactccg ccaacaacgg caacgcgacc    420
aaccacctct cgccgtggga gttcgacacc atcctcaact cggagttcaa cgacatgagc    480
ggcaaccatg tcgggatcga cgtcaacggc ctcaactccg tcgacgccga caacgccggg    540
tactacgacg acggcaccgg cgacttcaag aacatgagcc tggtgagccg caggccgatg    600
caggtgtggg tggacttcga cggccagacc atgcaggtca atgtcaccat ggcgccgctg    660
gaggtggcgc ggccaaagaa gcccctgctg tccaaaatcg tcaacatctc ctccgtcatt    720
gatgacaccg cctacgtcgg cttctcctcg gcgaccggca tcctcttctg ccgccactac    780
gtgctcggct ggagcttcaa gatgaacggc gccgcgccgg cgctcaacat ctcatccctg    840
ccctccctgc cggtcacgtt ccccaagcgc cggtccaaga gcttgagat cgtgctgccg    900 atagcctcgg cggtgctcgt cttcgcggtg gccgccgccg tgttcgtgtt catgcggcgg    960
cggcgcatgt tctcggagct caaggaggag tgggaggtga cgttcgggcc tcacaggttc    1020
tcgtacaagg acctgttcca cgccaccgac gggttcagcg acaagcggct cctcggcatc    1080
ggcgggttcg gcgcgtgta ccgtggcgtg ctcccgtcgt ccaaggcgga ggtcgccgtg    1140
aagaaggtgg cgcacgggtc gaggcagggg atgaggagt tcgtggcgga ggtggtcagc    1200
atcggccggc tccggcaccg gaacctcgtg cagctgctcg gctactgccg gcgcaagggc    1260
gagctcctgc tggtgtacga ctacatgccc aacggcagcc tggacaagca gctgtacgac    1320
cagggcaaga tcaccctgag atgggcgcag aggttccgca tcatcagggg cgtcgcgtcc    1380
gggctgctct acctccacga ggactgggag caggtggtgg tgcacaggga catcaaggcc    1440
agcaacgtgc tgctcgacgc cgacatgaac ggccggctcg gcgacttcgg cctggcgcgg    1500
```

```
ctgtacgacc acggcaccga cccgcacacg acgcacgtgg tgggcaccat gggctacctg    1560
gcgccggagc tggggcacac cggcaaggcg tccaaggcgt cggacgtgtt cgcgttcggg    1620
gccttcatgc tggaggtggc cgtgcgggcg aagcccgtgg cgcaggacgc gcgcgacaac    1680
cgcgtcgtgc tcgtcgactg ggtgctcgac cggtggcgcg ccggggcgat cacggacacg    1740
gtggacccgc gcctgcacgg cgacttcgtc gagagcgagg cgagcctcgt gctgcggctg    1800
ggcctgctgt gctcgcaccc gctgcccggc gcacggccgg ggacgaggca gcttgtgcag    1860
tacctggaag gcgacgtgcc gctgccggag ctgtcgccga cgtaccagag cttcaacatg    1920
ctggcgctca tgcaggacca ggggttcgac ccctacgtca tgtcctaccc gatgacatcc    1980
accagcgcag gcaccttctc tgacctctct ggaggtagat ga                       2022
```

<210> SEQ ID NO 17
<211> LENGTH: 673
<212> TYPE: PRT
<213> ORGANISM: Oryza sativa

<400> SEQUENCE: 17

```
Met Val Leu Pro Lys Pro Glu Met Pro Phe Phe Val Leu Leu Leu Phe
1               5                   10                  15

Leu Gly Leu Gly Cys Leu Arg Pro Ala Ala Thr Asp Glu Arg Phe
            20                  25                  30

Val Phe Asn Gly Phe Thr Gly Ala Asn Leu Ser Phe Asp Gly Met Ala
        35                  40                  45

Thr Val Thr Ser Asn Gly Leu Leu Met Leu Thr Asn Gly Thr Asn Gln
    50                  55                  60

Leu Lys Gly His Ala Phe Phe Pro Ser Pro Leu Gln Phe Gln Arg Gly
65                  70                  75                  80

Pro Asn Ser Thr Ala Met Gln Ser Phe Ser Thr Ala Phe Val Ile Gly
                85                  90                  95

Ile Ile Gly Ala Phe Glu Asp Leu Ser Ser His Gly Met Ala Phe Ile
            100                 105                 110

Ile Ala Lys Ser Lys Asn Leu Thr Ser Ala Leu Pro Gly Gln Phe Met
        115                 120                 125

Gly Leu Val Asn Ser Ala Asn Asn Gly Asn Ala Thr Asn His Leu Phe
    130                 135                 140

Ala Val Glu Phe Asp Thr Ile Leu Asn Ser Glu Phe Asn Asp Met Ser
145                 150                 155                 160

Gly Asn His Val Gly Ile Asp Val Asn Gly Leu Asn Ser Val Asp Ala
                165                 170                 175

Asp Asn Ala Gly Tyr Tyr Asp Asp Gly Thr Gly Asp Phe Lys Asn Met
            180                 185                 190

Ser Leu Val Ser Arg Arg Pro Met Gln Val Trp Val Asp Phe Asp Gly
        195                 200                 205

Gln Thr Met Gln Val Asn Val Thr Met Ala Pro Leu Glu Val Ala Arg
    210                 215                 220

Pro Lys Lys Pro Leu Leu Ser Lys Ile Val Asn Ile Ser Ser Val Ile
225                 230                 235                 240

Asp Asp Thr Ala Tyr Val Gly Phe Ser Ser Ala Thr Gly Ile Leu Phe
                245                 250                 255

Cys Arg His Tyr Val Leu Gly Trp Ser Phe Lys Met Asn Gly Ala Ala
            260                 265                 270

Pro Ala Leu Asn Ile Ser Ser Leu Pro Ser Leu Pro Val Thr Phe Pro
        275                 280                 285
```

```
Lys Pro Arg Ser Lys Thr Leu Glu Ile Val Leu Pro Ile Ala Ser Ala
        290                 295                 300

Val Leu Val Phe Ala Val Ala Ala Ala Val Phe Val Phe Met Arg Arg
305                 310                 315                 320

Arg Arg Met Phe Ser Glu Leu Lys Glu Glu Trp Glu Val Thr Phe Gly
                325                 330                 335

Pro His Arg Phe Ser Tyr Lys Asp Leu Phe His Ala Thr Asp Gly Phe
                340                 345                 350

Ser Asp Lys Arg Leu Leu Gly Ile Gly Gly Phe Gly Arg Val Tyr Arg
            355                 360                 365

Gly Val Leu Pro Ser Ser Lys Ala Glu Val Ala Val Lys Lys Val Ala
        370                 375                 380

His Gly Ser Arg Gln Gly Met Arg Glu Phe Val Ala Glu Val Val Ser
385                 390                 395                 400

Ile Gly Arg Leu Arg His Arg Asn Leu Val Gln Leu Leu Gly Tyr Cys
                405                 410                 415

Arg Arg Lys Gly Glu Leu Leu Leu Val Tyr Asp Tyr Met Pro Asn Gly
                420                 425                 430

Ser Leu Asp Lys Gln Leu Tyr Asp Gln Gly Lys Ile Thr Leu Arg Trp
            435                 440                 445

Ala Gln Arg Phe Arg Ile Ile Arg Gly Val Ala Ser Gly Leu Leu Tyr
        450                 455                 460

Leu His Glu Asp Trp Glu Gln Val Val His Arg Asp Ile Lys Ala
465                 470                 475                 480

Ser Asn Val Leu Leu Asp Ala Asp Met Asn Gly Arg Leu Gly Asp Phe
                485                 490                 495

Gly Leu Ala Arg Leu Tyr Asp His Gly Thr Asp Pro His Thr Thr His
            500                 505                 510

Val Val Gly Thr Met Gly Tyr Leu Ala Pro Glu Leu Gly His Thr Gly
        515                 520                 525

Lys Ala Ser Lys Ala Ser Asp Val Phe Ala Phe Gly Ala Phe Met Leu
        530                 535                 540

Glu Val Ala Cys Gly Arg Lys Pro Val Ala Gln Asp Ala Arg Asp Asn
545                 550                 555                 560

Arg Val Val Leu Val Asp Trp Val Leu Asp Arg Trp Arg Ala Gly Ala
                565                 570                 575

Ile Thr Asp Thr Val Asp Pro Arg Leu His Gly Asp Phe Val Glu Ser
            580                 585                 590

Glu Ala Ser Leu Val Leu Arg Leu Gly Leu Leu Cys Ser His Pro Leu
        595                 600                 605

Pro Gly Ala Arg Pro Gly Thr Arg Gln Leu Val Gln Tyr Leu Glu Gly
        610                 615                 620

Asp Val Pro Leu Pro Glu Leu Ser Pro Thr Tyr Gln Ser Phe Asn Met
625                 630                 635                 640

Leu Ala Leu Met Gln Asp Gln Gly Phe Asp Pro Tyr Val Met Ser Tyr
                645                 650                 655

Pro Met Thr Ser Thr Ser Ala Gly Thr Phe Ser Asp Leu Ser Gly Gly
                660                 665                 670

Arg

<210> SEQ ID NO 18
<211> LENGTH: 2464
<212> TYPE: DNA
```

<213> ORGANISM: Oryza sativa

<400> SEQUENCE: 18

| | | | | | | |
|---|---|---|---|---|---|---|
| gtagcgagga | gtgtgaacga | tgtgatgcca | ctgccagtat | gccacacaca | accagtaaac | 60 |
| ctgggataat | ggttggtgtc | cggtgttcat | gcattgactc | gaatagcgag | tcttctgttc | 120 |
| agacatttga | tgctatgact | cgaatagcgg | tgactacaca | tcatatgccc | tgtgctaatt | 180 |
| gcaactccca | aacggaagca | aatctcccga | tgggtaatca | ccgcttgctg | ctgctcctcc | 240 |
| tcctcctgct | cgcggtcgtt | ggctctgatc | atggggcgt | gctcgccgcc | gacgagttca | 300 |
| cctacaacgg | cttcggcggt | gccaacctca | cgctcgacgg | catggccgcc | gtggcgccca | 360 |
| acggcctcct | cgtgctcagc | aacggcacga | accagatggc | cgggcacgcg | ttccacccga | 420 |
| cgccgatccg | cctgcgggc | ggcgcggcgg | gcggcgccgt | ccagtccttc | tcggccgcgt | 480 |
| tcgtcttcgc | catcgtgtcc | aacttcaccg | tgctgagcga | caacggcatg | gcgttcgtgg | 540 |
| tcgcgcccag | cacgcggctc | tccaccttca | cgccggcca | gtacctcggc | atcctcaacg | 600 |
| tcaccgacaa | cggcaacgcc | gataacaaca | tcttcgccgt | cgagctcgac | accatgctca | 660 |
| acccggagtt | ccaggacatg | aacagcaacc | acatcggcgt | cgacatcaac | agcatgaagt | 720 |
| ccgtgcagaa | ccacagcgcc | ggctactacg | acgaagccac | gggggccttc | aacaatctga | 780 |
| gcttgatcag | ccgccagccg | atgcaggtgt | gggtggacta | cgacggcgcc | accacggtgc | 840 |
| tcaacgtgac | gatggcgccg | ctcgacgttc | ccaagcccag | taagccctc | atctccgcgc | 900 |
| ccgtcaacct | ctcgtccgtc | gtgaccgaca | cggcgtacgt | cgggttctcg | gcggccacgg | 960 |
| gcgtcatcta | cacgcggcac | tacgttctcg | gctggagctt | ctcccagaac | ggcgccgctc | 1020 |
| cttctctcca | cacctcaagc | ctcccggcgc | tgccgcggtt | cgggccgaag | ccccgttcca | 1080 |
| aggtgctgga | gatcgtgctc | ccgatcgcca | ccgcggcgt | cgtcctcgcg | ctggtcatcg | 1140 |
| ccgccttcct | gttcgtccgg | aggcgggtga | ggtacgccga | ggtgcgggag | gactgggagg | 1200 |
| tggagttcgg | accgcaccgc | ttctcctaca | aggagctcta | ccaggcgaca | aaggggttca | 1260 |
| agaacaagca | gctgctcggc | accggcggat | tcggcagggt | gtacaagggc | gtgctcgcga | 1320 |
| aatccaacct | cgagatcgcc | gtgaagaggg | tgtcgcacga | ctcgaagcaa | gggatgaagg | 1380 |
| agttcatcgc | ggaggtcgtc | agcatcggcc | acctccggca | ccgcaacctc | gtgcagctgc | 1440 |
| tcggctactg | ccgcgcaag | ggcgagctcc | tgctggtgta | cgactacatg | tccaacggca | 1500 |
| gcctcgacaa | gtacttgtac | gacaagacca | agcctgttct | tgattggggg | cagaggtttc | 1560 |
| agatcatcaa | gggcgtcgcc | tccggcctgc | tctacctcca | cgaggactgg | gagcaggtcg | 1620 |
| tcatccaccg | ggacatcaag | gcgagcaacg | tgctcctcga | cggcgagatg | aacggcaggc | 1680 |
| tgggcgactt | cggcctcgcg | aggctgtacg | accacggcgt | tgaccgcag | acgacgcacg | 1740 |
| tcgtcggcac | catgggttac | ctcgcccgg | agctggtgcg | cacgggcaag | gcgacgccgg | 1800 |
| tcaccgacgt | gttcgcgttc | ggcgtgttcg | tgctggaggt | cacctgcggg | cggcggccgc | 1860 |
| tcggctgcat | cgcgcccgac | gaccagaacg | tgctgctgga | ctgggtgcag | gagcacgagc | 1920 |
| gccggcacgc | ggccctcgac | acggtggacg | cgaggctgtg | cggcaagtac | gacgccgacg | 1980 |
| aggcgaggct | ggcgctcaag | ctggggctca | tgtgcgcgca | cccgttgccc | gacgcgcgcc | 2040 |
| ccaccatgcg | ccaggtcacg | cagtacctgg | acggcgacgc | acccatgccg | gaggtggcgc | 2100 |
| cgacgatggt | gagctacacc | atgctggcgc | tgatgcagaa | cgacgggttc | gactcgttcg | 2160 |
| ccatgtcctt | cccttccacc | gtcacgtcga | ccgccagccc | catgtccgcc | gacgtctcgg | 2220 |
| ccgtgtccgg | cctctccggt | ggaaggtgaa | caaacaaaca | aaaaggccgc | cgcaaaataa | 2280 |

```
tggtcacaac aacccgttct cctggtgact tgtcatctat cgtgtaacat agtgtagagc    2340
actagtgact acgtagtagt gaggtcactg ttcactgctg attaccacag tatatcccca    2400
tattagttta ccaatcaagc agtaatacgt atattacagt gagtgtgcaa agcttcgaga    2460
aggc                                                                 2464

<210> SEQ ID NO 19
<211> LENGTH: 2211
<212> TYPE: DNA
<213> ORGANISM: Oryza sativa

<400> SEQUENCE: 19
atgccacaca caaccagtaa acctgggata atggttggtg tccggtgttc atgcattgac      60
tcgaatagcg agtcttctgt tcagacattt gatgctatga ctcgaatagc ggtgactaca     120
catcatatgc cctgtgctaa ttgcaactcc caaacggaag caaatctccc gatgggtaat     180
caccgcttgc tgctgctcct cctcctcctg ctcgcggtc ttggctctga tcatggggc      240 gtgctcgccg ccgacgagtt cacctacaac ggcttcggcg gtgccaacct cacgctcgac     300
ggcatggccg ccgtggcgcc caacggcctc ctcgtgctca gcaacggcac gaaccagatg     360
gccgggcacg cgttccaccc gacgccgatc cgcctgcggg gcggcgcggc gggcggcgcc     420
gtccagtcct tctcggccgc gttcgtcttc gccatcgtgt ccaacttcac cgtgctgagc     480
gacaacggca tggcgttcgt ggtcgcgccc agcacgcggc tctccacctt caacgccggc     540
cagtacctcg gcatcctcaa cgtcaccgac aacggcaacg ccgataacaa catcttcgcc     600
gtcgagctcg acaccatgct caacccggag ttccaggaca tgaacagcaa ccacatcggc     660
gtcgacatca acagcatgaa gtccgtgcag aaccacagcg ccggctacta cgacgaagcc     720
acgggggcct tcaacaatct gagcttgatc agccgccagc cgatgcaggt gtgggtggac     780
tacgacggcg ccaccacggt gctcaacgtg acgatggcgc cgctcgacgt tcccaagccc     840
agtaagcccc tcatctccgc gcccgtcaac ctctcgtccg tcgtgaccga cacggcgtac     900
gtcgggttct cggcgccac gggcgtcatc tacacgcggc actacgttct cggctggagc     960
ttctcccaga acggcgccgc tccttctctc cacacctcaa gcctcccggc gctgccgcgg    1020
ttcgggccga agccccgttc caaggtgctg gagatcgtgc tcccgatcgc caccgcggcg    1080
ttcgtcctcg cgctggtcat cgccgccttc ctgttcgtcc ggaggcgggt gaggtacgcc    1140
gaggtgcggg aggactggga ggtggagttc ggaccgcacc gcttctccta caaggagctc    1200
taccaggcga caagggggtt caagaacaag cagctgctcg gcaccggcgg attcggcagg    1260
gtgtacaagg gcgtgctcgc gaaatccaac ctcgagatcg ccgtgaagag ggtgtcgcac    1320
gactcgaagc aagggatgaa ggagttcatc gcggaggtct cagcatcgg ccacctccgg    1380 caccgcaacc tcgtgcagct gctcggctac tgccggcgca agggcgagct cctgctggtg    1440
tacgactaca tgtccaacgg cagcctcgac aagtacttgt acgacaagac caagcctgtt    1500
cttgattggg ggcagagggtt tcagatcatc aagggcgtcg cctccggcct gctctacctc    1560
cacgaggact gggagcaggt cgtcatccac cgggacatca aggcgagcaa cgtgctcctc    1620
gacggcgaga tgaacggcag gctgggcgac ttcggcctcg cgaggctgta cgaccacggc    1680
gttgacccgc agacgacgca cgtcgtcggc accatggggtt acctcgcccc ggagctggtg    1740
cgcacgggca aggcgacgcc ggtcaccgac gtgttcgcgt tcggcgtgtt cgtgctggag    1800
gtcacctgcg ggcggcggcc gctcggctgc atcgcgcccg acgaccagaa cgtgctgctg    1860
```

-continued

```
gactgggtgc aggagcacga gcgccggcac gcggccctcg acacggtgga cgcgaggctg    1920
tgcggcaagt acgacgccga cgaggcgagg ctggcgctca agctggggct catgtgcgcg    1980
cacccgttgc ccgacgcgcg ccccaccatg cgccaggtca cgcagtacct ggacggcgac    2040
gcacccatgc cggaggtggc gccgacgatg gtgagctaca ccatgctggc gctgatgcag    2100
aacgacgggt cgactcgtt cgccatgtcc ttcccttcca ccgtcacgtc gaccgccagc     2160
cccatgtccg ccgacgtctc ggccgtgtcc ggcctctccg gtggaaggtg a             2211
```

<210> SEQ ID NO 20
<211> LENGTH: 736
<212> TYPE: PRT
<213> ORGANISM: Oryza sativa

<400> SEQUENCE: 20

```
Met Pro His Thr Thr Ser Lys Pro Gly Ile Met Val Gly Val Arg Cys
1               5                   10                  15

Ser Cys Ile Asp Ser Asn Ser Glu Ser Ser Val Gln Thr Phe Asp Ala
            20                  25                  30

Met Thr Arg Ile Ala Val Thr Thr His His Met Pro Cys Ala Asn Cys
        35                  40                  45

Asn Ser Gln Thr Glu Ala Asn Leu Pro Met Gly Asn His Arg Leu Leu
    50                  55                  60

Leu Leu Leu Leu Leu Leu Ala Val Val Gly Ser Asp His Gly Gly
65                  70                  75                  80

Val Leu Ala Ala Asp Glu Phe Thr Tyr Asn Gly Phe Gly Gly Ala Asn
                85                  90                  95

Leu Thr Leu Asp Gly Met Ala Ala Val Ala Pro Asn Gly Leu Leu Val
            100                 105                 110

Leu Ser Asn Gly Thr Asn Gln Met Ala Gly His Ala Phe His Pro Thr
        115                 120                 125

Pro Ile Arg Leu Arg Gly Gly Ala Ala Gly Gly Ala Val Gln Ser Phe
    130                 135                 140

Ser Ala Ala Phe Val Phe Ala Ile Val Ser Asn Phe Thr Val Leu Ser
145                 150                 155                 160

Asp Asn Gly Met Ala Phe Val Val Ala Pro Ser Thr Arg Leu Ser Thr
                165                 170                 175

Phe Asn Ala Gly Gln Tyr Leu Gly Ile Leu Asn Val Thr Asp Asn Gly
            180                 185                 190

Asn Ala Asp Asn Asn Ile Phe Ala Val Glu Leu Asp Thr Met Leu Asn
        195                 200                 205

Pro Glu Phe Gln Asp Met Asn Ser Asn His Ile Gly Val Asp Ile Asn
    210                 215                 220

Ser Met Lys Ser Val Gln Asn His Ser Ala Gly Tyr Tyr Asp Glu Ala
225                 230                 235                 240

Thr Gly Ala Phe Asn Asn Leu Ser Leu Ile Ser Arg Gln Pro Met Gln
                245                 250                 255

Val Trp Val Asp Tyr Asp Gly Ala Thr Thr Val Leu Asn Val Thr Met
            260                 265                 270

Ala Pro Leu Asp Val Pro Lys Pro Ser Lys Pro Leu Ile Ser Ala Pro
        275                 280                 285

Val Asn Leu Ser Ser Val Val Thr Asp Thr Ala Tyr Val Gly Phe Ser
    290                 295                 300

Ala Ala Thr Gly Val Ile Tyr Thr Arg His Tyr Val Leu Gly Trp Ser
305                 310                 315                 320
```

-continued

Phe Ser Gln Asn Gly Ala Ala Pro Ser Leu His Thr Ser Ser Leu Pro
                325                 330                 335

Ala Leu Pro Arg Phe Gly Pro Lys Pro Arg Ser Lys Val Leu Glu Ile
            340                 345                 350

Val Leu Pro Ile Ala Thr Ala Ala Phe Val Leu Ala Leu Val Ile Ala
            355                 360                 365

Ala Phe Leu Phe Val Arg Arg Arg Val Arg Tyr Ala Glu Val Arg Glu
        370                 375                 380

Asp Trp Glu Val Glu Phe Gly Pro His Arg Phe Ser Tyr Lys Glu Leu
385                 390                 395                 400

Tyr Gln Ala Thr Lys Gly Phe Lys Asn Lys Gln Leu Leu Gly Thr Gly
                405                 410                 415

Gly Phe Gly Arg Val Tyr Lys Gly Val Leu Ala Lys Ser Asn Leu Glu
            420                 425                 430

Ile Ala Val Lys Arg Val Ser His Asp Ser Lys Gln Gly Met Lys Glu
            435                 440                 445

Phe Ile Ala Glu Val Val Ser Ile Gly His Leu Arg His Arg Asn Leu
        450                 455                 460

Val Gln Leu Leu Gly Tyr Cys Arg Arg Lys Gly Glu Leu Leu Leu Val
465                 470                 475                 480

Tyr Asp Tyr Met Ser Asn Gly Ser Leu Asp Lys Tyr Leu Tyr Asp Lys
                485                 490                 495

Thr Lys Pro Val Leu Asp Trp Gly Gln Arg Phe Gln Ile Ile Lys Gly
            500                 505                 510

Val Ala Ser Gly Leu Leu Tyr Leu His Glu Asp Trp Glu Gln Val Val
            515                 520                 525

Ile His Arg Asp Ile Lys Ala Ser Asn Val Leu Leu Asp Gly Glu Met
530                 535                 540

Asn Gly Arg Leu Gly Asp Phe Gly Leu Ala Arg Leu Tyr Asp His Gly
545                 550                 555                 560

Val Asp Pro Gln Thr Thr His Val Val Gly Thr Met Gly Tyr Leu Ala
                565                 570                 575

Pro Glu Leu Val Arg Thr Gly Lys Ala Thr Pro Val Thr Asp Val Phe
            580                 585                 590

Ala Phe Gly Val Phe Val Leu Glu Val Thr Cys Gly Arg Arg Pro Leu
        595                 600                 605

Gly Cys Ile Ala Pro Asp Asp Gln Asn Val Leu Leu Asp Trp Val Gln
        610                 615                 620

Glu His Glu Arg Arg His Ala Ala Leu Asp Thr Val Asp Ala Arg Leu
625                 630                 635                 640

Cys Gly Lys Tyr Asp Ala Asp Glu Ala Arg Leu Ala Leu Lys Leu Gly
                645                 650                 655

Leu Met Cys Ala His Pro Leu Pro Asp Ala Arg Pro Thr Met Arg Gln
            660                 665                 670

Val Thr Gln Tyr Leu Asp Gly Asp Ala Pro Met Pro Glu Val Ala Pro
            675                 680                 685

Thr Met Val Ser Tyr Thr Met Leu Ala Leu Met Gln Asn Asp Gly Phe
        690                 695                 700

Asp Ser Phe Ala Met Ser Phe Pro Ser Thr Val Thr Ser Thr Ala Ser
705                 710                 715                 720

Pro Met Ser Ala Asp Val Ser Ala Val Ser Gly Leu Ser Gly Gly Arg
                725                 730                 735

```
<210> SEQ ID NO 21
<211> LENGTH: 26
<212> TYPE: DNA
<213> ORGANISM: Artificial Sequence
<220> FEATURE:
<223> OTHER INFORMATION: Forward primer for cloning cDNA of OsGSTU41
      gene

<400> SEQUENCE: 21
aaatggttaa gctaatcagc gccttc                                      26

<210> SEQ ID NO 22
<211> LENGTH: 27
<212> TYPE: DNA
<213> ORGANISM: Artificial Sequence
<220> FEATURE:
<223> OTHER INFORMATION: Reverse primer for cloning cDNA of OsGSTU41
      gene

<400> SEQUENCE: 22
tacgcatatt ccagcatcga aattcac                                     27

<210> SEQ ID NO 23
<211> LENGTH: 24
<212> TYPE: DNA
<213> ORGANISM: Artificial Sequence
<220> FEATURE:
<223> OTHER INFORMATION: Forward primer for cloning cDNA of OsPPCK4 gene

<400> SEQUENCE: 23
ggagaagaga atcgcggaga tagc                                        24

<210> SEQ ID NO 24
<211> LENGTH: 24
<212> TYPE: DNA
<213> ORGANISM: Artificial Sequence
<220> FEATURE:
<223> OTHER INFORMATION: Reverse primer for cloning cDNA of OsPPCK4 gene

<400> SEQUENCE: 24
tggagttcat catcatcctc gatc                                        24

<210> SEQ ID NO 25
<211> LENGTH: 24
<212> TYPE: DNA
<213> ORGANISM: Artificial Sequence
<220> FEATURE:
<223> OTHER INFORMATION: Forward primer for cloning cDNA of OsCAM2 gene

<400> SEQUENCE: 25
ctcgcggaac cttctcgaag cttc                                        24

<210> SEQ ID NO 26
<211> LENGTH: 22
<212> TYPE: DNA
<213> ORGANISM: Artificial Sequence
<220> FEATURE:
<223> OTHER INFORMATION: Reverse primer for cloning cDNA of OsCAM2 gene

<400> SEQUENCE: 26
cagctttgtt gtaggccctg ac                                          22

<210> SEQ ID NO 27
<211> LENGTH: 26
<212> TYPE: DNA
<213> ORGANISM: Artificial Sequence
```

```
<220> FEATURE:
<223> OTHER INFORMATION: Forward primer for cloning gDNA of OsDN-DTP4
      gene

<400> SEQUENCE: 27
gcggcaaaaa cgatgtcagt ggctag                                    26

<210> SEQ ID NO 28
<211> LENGTH: 29
<212> TYPE: DNA
<213> ORGANISM: Artificial Sequence
<220> FEATURE:
<223> OTHER INFORMATION: Reverse primer for cloning gDNA of OsDN-DTP4
      gene

<400> SEQUENCE: 28
gtcccttaac tatataaaac cggtctccc                                 29

<210> SEQ ID NO 29
<211> LENGTH: 23
<212> TYPE: DNA
<213> ORGANISM: Artificial Sequence
<220> FEATURE:
<223> OTHER INFORMATION: Forward primer for cloning gDNA of OsLecRK4.1
      gene

<400> SEQUENCE: 29
accggggccg tgacttgact gac                                       23

<210> SEQ ID NO 30
<211> LENGTH: 25
<212> TYPE: DNA
<213> ORGANISM: Artificial Sequence
<220> FEATURE:
<223> OTHER INFORMATION: Reverse primer for cloning gDNA of OsLecRK4.1
      gene

<400> SEQUENCE: 30
cgtcgacaat cagatcagag gagaa                                     25

<210> SEQ ID NO 31
<211> LENGTH: 28
<212> TYPE: DNA
<213> ORGANISM: Artificial Sequence
<220> FEATURE:
<223> OTHER INFORMATION: Forward primer for cloning gDNA of OsLecRK4.2
      gene

<400> SEQUENCE: 31
gtagcgagga gtgtgaacga tgtgatgc                                  28

<210> SEQ ID NO 32
<211> LENGTH: 28
<212> TYPE: DNA
<213> ORGANISM: Artificial Sequence
<220> FEATURE:
<223> OTHER INFORMATION: Reverse primer for cloning gDNA of OsLecRK4.2
      gene

<400> SEQUENCE: 32
gccttctcga agctttgcac actcactg                                  28

<210> SEQ ID NO 33
<211> LENGTH: 18
<212> TYPE: DNA
<213> ORGANISM: Artificial Sequence
<220> FEATURE:
```

```
<223> OTHER INFORMATION: Forward primer for real-time RT-PCR analysis of
      OsGSTU41 gene

<400> SEQUENCE: 33
ggctgtcgtt ctggatgg                                                    18

<210> SEQ ID NO 34
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsGSTU41 gene

<400> SEQUENCE: 34
gcagtgaaca aggcgacg                                                    18

<210> SEQ ID NO 35
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsPPCK4 gene

<400> SEQUENCE: 35
gctctacatg atgctctccg                                                  20

<210> SEQ ID NO 36
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsPPCK4 gene

<400> SEQUENCE: 36
gagacgtcct tgcagagc                                                    18

<210> SEQ ID NO 37
<211> LENGTH: 21
<212> TYPE: DNA
<213> ORGANISM: Artificial Sequence
<220> FEATURE:
<223> OTHER INFORMATION: Forward primer for real-time RT-PCR analysis of
      OsDN-DTP4 gene

<400> SEQUENCE: 37
ccagttcaga gtacggtgcc g                                                21

<210> SEQ ID NO 38
<211> LENGTH: 22
<212> TYPE: DNA
<213> ORGANISM: Artificial Sequence
<220> FEATURE:
<223> OTHER INFORMATION: Reverse primer for real-time RT-PCR analysis of
      OsDN-DTP4 gene

<400> SEQUENCE: 38
gtgtccacgt cagcctcctt tc                                               22

<210> SEQ ID NO 39
<211> LENGTH: 18
<212> TYPE: DNA
<213> ORGANISM: Artificial Sequence
<220> FEATURE:
<223> OTHER INFORMATION: Forward primer for real-time RT-PCR analysis of
```

-continued

```
      OsLecRK4.1 gene

<400> SEQUENCE: 39
cgctcaacat ctcatccc                                                 18

<210> SEQ ID NO 40
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsLecRK4.1 gene

<400> SEQUENCE: 40
ccgcatgaac acgaacac                                                 18

<210> SEQ ID NO 41
<211> LENGTH: 18
<212> TYPE: DNA
<213> ORGANISM: Artificial Sequence
<220> FEATURE:
<223> OTHER INFORMATION: Forward primer for real-time RT-PCR analysis of
      OsLecRK4.2 gene

<400> SEQUENCE: 41
ccgacgatgg tgagctac                                                 18

<210> SEQ ID NO 42
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsLecRK4.2 gene

<400> SEQUENCE: 42
gtgacggtgg aagggaag                                                 18
```